United States Patent
O'Donnell et al.

(10) Patent No.: US 12,206,983 B2
(45) Date of Patent: *Jan. 21, 2025

(54) PORTABLE DIGITAL VIDEO CAMERA CONFIGURED FOR REMOTE IMAGE ACQUISITION CONTROL AND VIEWING

(71) Applicant: Contour IP Holding, LLC, Lake Forest, IL (US)

(72) Inventors: Laura O'Donnell, Hermosa Beach, CA (US); Richard Mander, Bainbridge, WA (US); Michael Denton, Christchurch (NZ); Ben Bodley, Christchurch (NZ); Alan Tompkins, Ferny Grove (AU); Keith Gurganus, San Diego, CA (US); Kelvin P. Barnsdale, Christchurch (NZ); Simon Third, Christchurch (NZ); Carm Pierce, Stanwood, WA (US); Carl Perkins, Seattle, WA (US)

(73) Assignee: Contour IP Holding, LLC, Lake Forest, IL (US)

(*) Notice: Subject to any disclaimer, the term of this patent is extended or adjusted under 35 U.S.C. 154(b) by 0 days.

This patent is subject to a terminal disclaimer.

(21) Appl. No.: 17/937,753

(22) Filed: Oct. 3, 2022

(65) Prior Publication Data
US 2023/0027213 A1 Jan. 26, 2023

Related U.S. Application Data

(63) Continuation of application No. 17/356,318, filed on Jun. 23, 2021, which is a continuation of application (Continued)

(51) Int. Cl.
*H04N 23/661* (2023.01)
*G01S 19/19* (2010.01)
(Continued)

(52) U.S. Cl.
CPC .......... *H04N 23/661* (2023.01); *G01S 19/42* (2013.01); *G08B 13/19641* (2013.01);
(Continued)

(58) Field of Classification Search
CPC ... G01S 19/19; G01S 19/42; G08B 13/19641; G08B 13/1966; G08B 13/19682;
(Continued)

(56) References Cited

U.S. PATENT DOCUMENTS 4,034,402 A 7/1977 Brian
D246,528 S 11/1977 Miller
(Continued)

FOREIGN PATENT DOCUMENTS

CA 2463117 A1 8/2004
CN 1425953 A 6/2003
(Continued)

OTHER PUBLICATIONS

Complaint (without Appendices) filed Nov. 25, 2014, *Contour, LLC v. Camp Saver, LLC* (involving U.S. Pat. No. 8,890,954 and U.S. Pat. No. 8,896,694), Case No. 2:14-cv-00864-PMW, 16 pages.
(Continued)

*Primary Examiner* — Dakshesh D Parikh
(74) *Attorney, Agent, or Firm* — Knobbe, Martens, Olson & Bear, LLP

(57) ABSTRACT

A wearable digital video camera (10) is equipped with wireless connection protocol and global navigation and location positioning system technology to provide remote image acquisition control and viewing. The Bluetooth® packet-based open wireless technology standard protocol (400) is preferred for use in providing control signals or streaming data to the digital video camera and for accessing image content stored on or streaming from the digital video camera. The GPS technology (402) is preferred for use in
(Continued)

tracking of the location of the digital video camera as it records image information. A rotating mount (300) with a locking member (330) on the camera housing (22) allows adjustment of the pointing angle of the wearable digital video camera when it is attached to a mounting surface.

24 Claims, 35 Drawing Sheets

Related U.S. Application Data

No. 16/442,391, filed on Jun. 14, 2019, now Pat. No. 11,076,084, which is a continuation of application No. 15/623,070, filed on Jun. 14, 2017, now Pat. No. 10,356,304, which is a continuation of application No. 14/702,024, filed on May 1, 2015, now Pat. No. 9,742,975, which is a continuation of application No. 14/496,915, filed on Sep. 25, 2014, now abandoned, which is a continuation of application No. 13/822,255, filed as application No. PCT/US2011/051418 on Sep. 13, 2011, now Pat. No. 8,890,954.

(60) Provisional application No. 61/382,404, filed on Sep. 13, 2010.

(51) Int. Cl.
| | | |
|---|---|---|
| *G01S 19/42* | (2010.01) | |
| *G08B 13/196* | (2006.01) | |
| *G08C 17/02* | (2006.01) | |
| *G16H 40/67* | (2018.01) | |
| *H04N 5/28* | (2006.01) | |
| *H04N 7/18* | (2006.01) | |
| *H04N 21/218* | (2011.01) | |
| *H04N 21/2343* | (2011.01) | |
| *H04N 21/2365* | (2011.01) | |
| *H04N 21/2385* | (2011.01) | |
| *H04N 21/258* | (2011.01) | |
| *H04N 21/2662* | (2011.01) | |
| *H04N 21/462* | (2011.01) | |
| *H04N 23/50* | (2023.01) | |
| *H04N 23/51* | (2023.01) | |
| *H04N 23/55* | (2023.01) | |
| *H04N 23/617* | (2023.01) | |
| *H04N 23/66* | (2023.01) | |
| *H04W 80/02* | (2009.01) | |

(52) U.S. Cl.
CPC ..... *G08B 13/1966* (2013.01); *G08B 13/19682* (2013.01); *G08B 13/19684* (2013.01); *G08C 17/02* (2013.01); *G16H 40/67* (2018.01); *H04N 5/28* (2013.01); *H04N 7/18* (2013.01); *H04N 7/181* (2013.01); *H04N 7/183* (2013.01); *H04N 7/185* (2013.01); *H04N 21/21805* (2013.01); *H04N 21/234363* (2013.01); *H04N 21/2365* (2013.01); *H04N 21/2385* (2013.01); *H04N 21/25825* (2013.01); *H04N 21/2662* (2013.01); *H04N 21/4621* (2013.01); *H04N 23/50* (2023.01); *H04N 23/55* (2023.01); *H04N 23/617* (2023.01); *H04N 23/66* (2023.01); *G01S 19/19* (2013.01); *G08C 2201/93* (2013.01); *H04N 23/51* (2023.01); *H04W 80/02* (2013.01)

(58) Field of Classification Search
CPC .............. G08B 13/19684; G08C 17/02; G08C 2201/93; G16H 40/67; H04N 21/21805; H04N 21/234363; H04N 21/2365; H04N 21/2385; H04N 21/25825; H04N 21/2662; H04N 21/4621; H04N 23/50; H04N 23/51; H04N 23/55; H04N 23/617; H04N 23/66; H04N 23/661; H04N 5/28; H04N 5/76; H04N 7/18; H04N 7/181; H04N 7/183; H04N 7/185; H04W 80/02
See application file for complete search history.

(56) References Cited

U.S. PATENT DOCUMENTS

| | | |
|---|---|---|
| 4,068,248 A | 1/1978 | Pizzuti et al. |
| 4,516,157 A | 5/1985 | Campbell |
| 4,525,045 A | 6/1985 | Fazekas |
| 4,642,678 A | 2/1987 | Cok |
| D292,982 S | 12/1987 | Nakatani |
| 4,774,574 A | 9/1988 | Daley et al. |
| D301,628 S | 6/1989 | Fuller |
| 5,056,745 A | 10/1991 | Gelbard |
| 5,189,511 A | 2/1993 | Parulski et al. |
| 5,198,849 A | 3/1993 | Hurai |
| 5,218,439 A | 6/1993 | Mizoguchi et al. |
| 5,457,751 A | 10/1995 | Such |
| 5,469,211 A | 11/1995 | Maruichi |
| 5,493,335 A | 2/1996 | Parulski |
| 5,526,037 A | 6/1996 | Cortjens et al. |
| 5,557,329 A | 9/1996 | Lim |
| 5,583,571 A | 12/1996 | Friedland |
| D378,095 S | 2/1997 | Hasegawa |
| 5,649,240 A | 7/1997 | Saegusa |
| 5,652,621 A | 7/1997 | Adams, Jr. et al. |
| 5,666,582 A | 9/1997 | Nakai et al. |
| 5,668,597 A | 9/1997 | Paulski et al. |
| 5,721,989 A | 2/1998 | Kitazawa et al. |
| D392,300 S | 3/1998 | Chow et al. |
| 5,731,870 A | 3/1998 | Bartko et al. |
| 5,799,221 A | 8/1998 | Yamamoto et al. |
| 5,859,666 A | 1/1999 | Manabe |
| D405,815 S | 2/1999 | Takizawa |
| 5,886,735 A | 3/1999 | Bullister et al. |
| 5,933,137 A | 8/1999 | Anderson |
| 5,966,176 A | 10/1999 | Chow et al. |
| 5,983,035 A | 11/1999 | Funaki |
| 6,028,627 A | 2/2000 | Helmsderfer |
| 6,091,831 A | 7/2000 | Cho |
| D430,888 S | 9/2000 | Adachi et al. |
| 6,142,437 A | 11/2000 | Wilkins, Jr. |
| 6,192,162 B1 | 2/2001 | Hamilton, Jr. et al. |
| 6,288,742 B1 | 9/2001 | Ansari et al. |
| 6,292,218 B1 | 9/2001 | Parulski et al. |
| 6,300,976 B1 | 10/2001 | Furuoka |
| 6,335,753 B1 | 1/2002 | McDonald |
| 6,341,201 B1 | 1/2002 | Ishiguro et al. |
| 6,374,229 B1 | 4/2002 | Lowrey et al. |
| 6,377,302 B1 | 4/2002 | Ozaki et al. |
| 6,415,107 B1 | 7/2002 | Ogawa |
| 6,421,088 B1 | 7/2002 | Lee |
| 6,510,325 B1 | 1/2003 | Mack, II et al. |
| 6,518,881 B2 | 2/2003 | Monroe |
| 6,545,587 B1 | 4/2003 | Hatakeyama et al. |
| 6,686,886 B2 | 2/2004 | Flint |
| 6,704,044 B1 | 3/2004 | Foster et al. |
| 6,736,759 B1 | 5/2004 | Stubbs et al. |
| 6,771,304 B1 | 8/2004 | Mancuso et al. |
| 6,819,354 B1 | 11/2004 | Foster et al. |
| 6,825,875 B1 | 11/2004 | Strub et al. |
| 6,830,387 B2 | 12/2004 | Rife |
| 6,834,128 B1 | 12/2004 | Altunbasak et al. |
| D506,489 S | 6/2005 | Owada |
| D510,374 S | 10/2005 | Greenwood |
| 6,955,484 B2 | 10/2005 | Woodman |
| 6,956,599 B2 | 10/2005 | Lim et al. |
| 7,023,478 B2 | 4/2006 | MalloyDesormeaux |
| 7,046,275 B1 | 5/2006 | Yamada |
| D524,282 S | 7/2006 | Beasley et al. |
| 7,090,415 B2 | 8/2006 | Griga |
| 7,136,096 B1 | 11/2006 | Yamagishi et al. |

(56) References Cited

U.S. PATENT DOCUMENTS

| | | |
|---|---|---|
| 7,171,018 B2 | 1/2007 | Rhoads et al. |
| D547,346 S | 7/2007 | Ollila |
| 7,256,944 B2 | 8/2007 | Labaziewicz et al. |
| 7,257,158 B1 | 8/2007 | Figueredo |
| 7,273,321 B2 | 9/2007 | Woodman |
| D558,805 S | 1/2008 | Sadatsuki |
| 7,330,511 B2 | 2/2008 | Maltaaliati et al. |
| 7,353,086 B2 | 4/2008 | Ennis |
| 7,362,352 B2 | 4/2008 | Ueyama |
| 7,404,001 B2 | 7/2008 | Campbell et al. |
| 7,417,670 B1 | 8/2008 | Linzer et al. |
| D576,658 S | 9/2008 | Speggiorin |
| 7,450,835 B2 | 11/2008 | Lackey et al. |
| D581,959 S | 12/2008 | Chan |
| 7,458,736 B2 | 12/2008 | Woodman |
| 7,463,304 B2 | 12/2008 | Murray |
| 7,494,290 B2 | 2/2009 | Kim |
| 7,522,834 B2 | 4/2009 | Heaven et al. |
| 7,526,314 B2 | 4/2009 | Kennedy |
| D592,231 S | 5/2009 | Schnell |
| D592,235 S | 5/2009 | Bryant et al. |
| 7,536,487 B1 | 5/2009 | Kahn et al. |
| 7,542,077 B2 | 6/2009 | Miki |
| D596,658 S | 7/2009 | Dordick |
| 7,561,201 B2 | 7/2009 | Hong |
| 7,593,576 B2 | 9/2009 | Meyer et al. |
| 7,599,608 B2 | 10/2009 | Takemoto et al. |
| D603,442 S | 11/2009 | Dordick |
| 7,614,803 B2 | 11/2009 | Takeuchi |
| 7,646,910 B1 | 1/2010 | Linzer et al. |
| 7,658,556 B2 | 2/2010 | Johnson |
| 7,661,891 B2 | 2/2010 | Heibel |
| 7,675,550 B1 | 3/2010 | Linzer et al. |
| 7,688,203 B2 | 3/2010 | Rockefeller |
| 7,688,360 B2 | 3/2010 | Maeda |
| 7,688,364 B2 | 3/2010 | LeGall et al. |
| 7,725,015 B2 | 5/2010 | Tanoue |
| 7,733,416 B2 | 6/2010 | Gal |
| 7,753,599 B2 | 7/2010 | Segawa et al. |
| 7,764,320 B1 | 7/2010 | Salvato |
| 7,778,237 B2 | 8/2010 | Dowling |
| 7,839,429 B2 | 11/2010 | Williams et al. |
| 7,856,468 B2 | 12/2010 | Yoshimine et al. |
| D630,238 S | 1/2011 | Fukuma et al. |
| 7,880,776 B2 | 2/2011 | LeGall et al. |
| 7,893,967 B1 | 2/2011 | Linzer et al. |
| 7,898,573 B1 | 3/2011 | Linzer et al. |
| 7,907,836 B2 | 3/2011 | Shinohara et al. |
| D640,304 S | 6/2011 | Green et al. |
| D640,722 S | 6/2011 | Green et al. |
| 7,965,888 B2 | 6/2011 | Linzer et al. |
| 7,982,788 B1 | 7/2011 | Linzer et al. |
| D643,057 S | 8/2011 | Mendoza et al. |
| 8,014,656 B2 | 9/2011 | Woodman |
| D646,315 S | 10/2011 | Ort |
| 8,045,850 B2 | 10/2011 | Tanoue |
| 8,079,501 B2 | 12/2011 | Woodman |
| 8,099,289 B2 | 1/2012 | Mozer et al. |
| D653,692 S | 2/2012 | Dordick |
| 8,120,651 B2 | 2/2012 | Ennis |
| 8,131,071 B2 | 3/2012 | Linzer et al. |
| 8,199,251 B2 | 6/2012 | Woodman |
| D663,350 S | 7/2012 | O'Donnell et al. |
| D665,006 S | 8/2012 | Green et al. |
| 8,237,856 B2 | 8/2012 | Boland et al. |
| 8,243,171 B2 | 8/2012 | LeGall et al. |
| 8,265,151 B1 | 9/2012 | Wang et al. |
| D675,242 S | 1/2013 | O'Donnell et al. |
| 8,386,817 B2 | 2/2013 | Yamanaka et al. |
| 8,391,367 B1 | 3/2013 | Kohn et al. |
| 8,427,547 B1 | 4/2013 | Linzer et al. |
| 8,451,822 B2 | 5/2013 | Dowling |
| 8,526,779 B1 | 9/2013 | Simmons et al. |
| 8,538,253 B2 | 9/2013 | Winiarski |
| 8,593,570 B2 | 11/2013 | Boland et al. |
| D697,127 S | 1/2014 | O'Donnell et al. |
| 8,639,110 B2 | 1/2014 | Winiarski |
| 8,675,086 B1 | 3/2014 | Linzer et al. |
| 8,675,101 B1 | 3/2014 | Linzer et al. |
| 8,687,700 B1 | 4/2014 | Kwok et al. |
| 8,718,451 B1 | 5/2014 | Linzer et al. |
| 8,737,803 B2 | 5/2014 | Pereira et al. |
| 8,750,157 B1 | 6/2014 | Jagannath et al. |
| 8,768,142 B1 | 7/2014 | Ju et al. |
| 8,811,206 B2 | 8/2014 | Shukla |
| 8,831,505 B1 | 9/2014 | Seshadri |
| 8,860,844 B2 | 10/2014 | Choi et al. |
| 8,890,954 B2 | 11/2014 | O'Donnell et al. |
| 8,896,694 B2 | 11/2014 | O'Donnell et al. |
| 8,934,045 B2 | 1/2015 | Karn et al. |
| 8,941,747 B2 | 1/2015 | Boland et al. |
| 8,953,929 B2 | 2/2015 | Boland et al. |
| 9,004,783 B1 | 4/2015 | Woodman et al. |
| 9,286,776 B1 | 3/2016 | Morton |
| 9,742,975 B2 | 8/2017 | O'Donnell et al. |
| 10,356,304 B2 | 7/2019 | O'Donnell et al. |
| 11,076,084 B2 | 7/2021 | O'Donnell et al. |
| 11,831,983 B2 | 11/2023 | O'Donnell et al. |
| 2002/0030744 A1 | 3/2002 | Sawachi |
| 2002/0044152 A1 | 4/2002 | Abbott, III et al. |
| 2002/0067920 A1 | 6/2002 | Weng et al. |
| 2002/0097327 A1 | 7/2002 | Yamasaki |
| 2002/0109579 A1 | 8/2002 | Pollard et al. |
| 2002/0170064 A1 | 11/2002 | Monroe et al. |
| 2002/0186307 A1 | 12/2002 | Anderson |
| 2003/0063200 A1 | 4/2003 | Isoyama |
| 2003/0128975 A1 | 7/2003 | Shevick |
| 2003/0147960 A1 | 8/2003 | Lin et al. |
| 2003/0156208 A1 | 8/2003 | Obradovich |
| 2003/0157960 A1 | 8/2003 | Kennedy |
| 2003/0170009 A1 | 9/2003 | Itoh et al. |
| 2004/0004825 A1 | 1/2004 | Malard et al. |
| 2004/0032522 A1 | 2/2004 | Koeda |
| 2004/0051793 A1 | 3/2004 | Tecu et al. |
| 2004/0070536 A1 | 4/2004 | Stotler et al. |
| 2004/0107366 A1 | 6/2004 | Balfanz et al. |
| 2004/0201726 A1 | 10/2004 | Bloom et al. |
| 2004/0215958 A1 | 10/2004 | Eillis et al. |
| 2004/0227825 A1 | 11/2004 | Sakimura et al. |
| 2004/0247161 A1 | 12/2004 | Storm |
| 2004/0257456 A1 | 12/2004 | Goris et al. |
| 2005/0036766 A1 | 2/2005 | Takemoto et al. |
| 2005/0078195 A1* | 4/2005 | VanWagner ..... H04N 21/41407 348/E7.071 |
| 2005/0089244 A1 | 4/2005 | Jin et al. |
| 2005/0200750 A1 | 9/2005 | Ollila |
| 2005/0206736 A1 | 9/2005 | Ng et al. |
| 2005/0229108 A1 | 10/2005 | Sadek |
| 2005/0231599 A1 | 10/2005 | Yamasaki |
| 2005/0278446 A1 | 12/2005 | Bryant |
| 2006/0009257 A1 | 1/2006 | Ku |
| 2006/0023081 A1 | 2/2006 | Sekiguchi et al. |
| 2006/0055786 A1 | 3/2006 | Ollila |
| 2006/0056056 A1 | 3/2006 | Ahiska et al. |
| 2006/0061663 A1 | 3/2006 | Park |
| 2006/0095331 A1 | 5/2006 | O'malley |
| 2006/0182437 A1 | 8/2006 | Williams et al. |
| 2006/0221204 A1 | 10/2006 | Ogawa |
| 2006/0229108 A1 | 10/2006 | Cehelnik |
| 2006/0244727 A1 | 11/2006 | Salman |
| 2006/0263066 A1 | 11/2006 | Matsumoto |
| 2006/0268130 A1 | 11/2006 | Williams et al. |
| 2006/0271251 A1 | 11/2006 | Hopkins |
| 2006/0274171 A1 | 12/2006 | Wang |
| 2007/0024931 A1 | 2/2007 | Compton et al. |
| 2007/0035612 A1 | 2/2007 | Korneluk |
| 2007/0058074 A1 | 3/2007 | Yamagishi |
| 2007/0109417 A1 | 5/2007 | Hyttfors et al. |
| 2007/0111754 A1 | 5/2007 | Marshall et al. |
| 2007/0113261 A1 | 5/2007 | Roman |
| 2007/0126883 A1 | 6/2007 | Ishige et al. |
| 2007/0130599 A1 | 6/2007 | Monroe |
| 2007/0165875 A1 | 7/2007 | Rezvani et al. |
| 2007/0182812 A1 | 8/2007 | Ritchey |

(56) References Cited

U.S. PATENT DOCUMENTS

| | | |
|---|---|---|
| 2007/0206829 A1 | 9/2007 | Weinans et al. |
| 2007/0247515 A1 | 10/2007 | Roman |
| 2007/0255115 A1 | 11/2007 | Anglin et al. |
| 2007/0255496 A1* | 11/2007 | Fong ................. G01S 19/42 |
| | | 701/469 |
| 2007/0260797 A1 | 11/2007 | Chen |
| 2007/0288331 A1 | 12/2007 | Ebrom et al. |
| 2007/0291165 A1 | 12/2007 | Wang |
| 2008/0024594 A1 | 1/2008 | Ritchey |
| 2008/0039072 A1 | 2/2008 | Bloebaum |
| 2008/0046545 A1 | 2/2008 | Koren et al. |
| 2008/0104018 A1 | 5/2008 | Xia |
| 2008/0133227 A1 | 6/2008 | Kong et al. |
| 2008/0170130 A1 | 7/2008 | Ollila et al. |
| 2008/0232780 A1 | 9/2008 | Yamada |
| 2008/0247377 A1 | 10/2008 | Van Horn et al. |
| 2008/0259045 A1 | 10/2008 | Kim et al. |
| 2008/0284899 A1 | 11/2008 | Haubmann et al. |
| 2008/0310405 A1 | 12/2008 | Cox et al. |
| 2009/0028527 A1 | 1/2009 | Jang |
| 2009/0034951 A1 | 2/2009 | Kawasaki |
| 2009/0085740 A1 | 4/2009 | Klein et al. |
| 2009/0086041 A1 | 4/2009 | Choi et al. |
| 2009/0109292 A1 | 4/2009 | Ennis |
| 2009/0122177 A1 | 5/2009 | Murakami |
| 2009/0137274 A1 | 5/2009 | Kim |
| 2009/0189981 A1* | 7/2009 | Siann ................. H04N 23/00 |
| | | 348/143 |
| 2009/0195655 A1 | 8/2009 | Pandey |
| 2009/0213278 A1 | 8/2009 | Tsurumoto et al. |
| 2009/0265748 A1 | 10/2009 | Dotchevski et al. |
| 2009/0290847 A1 | 11/2009 | Sathav |
| 2009/0304197 A1 | 12/2009 | Joiner et al. |
| 2010/0026809 A1 | 2/2010 | Curry |
| 2010/0026816 A1 | 2/2010 | Bergstrom et al. |
| 2010/0060747 A1* | 3/2010 | Woodman ............ H04N 23/663 |
| | | 348/222.1 |
| 2010/0111489 A1 | 5/2010 | Presler |
| 2010/0112939 A1 | 5/2010 | Chang et al. |
| 2010/0118158 A1* | 5/2010 | Boland ................. H04N 23/63 |
| | | 348/376 |
| 2010/0141800 A1 | 6/2010 | Katayama |
| 2010/0231743 A1 | 9/2010 | Choi et al. |
| 2010/0245585 A1 | 9/2010 | Fisher et al. |
| 2010/0246669 A1 | 9/2010 | Harel |
| 2010/0253826 A1 | 10/2010 | Green et al. |
| 2010/0266270 A1 | 10/2010 | Pizzo et al. |
| 2010/0277591 A1 | 11/2010 | Kowalsky |
| 2010/0304783 A1 | 12/2010 | Logan et al. |
| 2010/0306335 A1 | 12/2010 | Rios et al. |
| 2010/0311441 A1 | 12/2010 | Hazlett et al. |
| 2010/0322441 A1 | 12/2010 | Hazlett et al. |
| 2010/0328471 A1 | 12/2010 | Boland |
| 2011/0019079 A1 | 1/2011 | Saiki |
| 2011/0044303 A1 | 2/2011 | Ji et al. |
| 2011/0050926 A1 | 3/2011 | Asano |
| 2011/0058052 A1 | 3/2011 | Bolton et al. |
| 2011/0096168 A1 | 4/2011 | Siann et al. |
| 2011/0279683 A1 | 11/2011 | Yarmchuk et al. |
| 2011/0280540 A1 | 11/2011 | Woodman |
| 2011/0285866 A1 | 11/2011 | Bhrugumalla |
| 2011/0309921 A1 | 12/2011 | Tachibana |
| 2012/0044354 A1 | 2/2012 | Cheng et al. |
| 2012/0063337 A1 | 3/2012 | Shukla |
| 2012/0099572 A1 | 4/2012 | Kato et al. |
| 2012/0110031 A1 | 5/2012 | Lancanski et al. |
| 2012/0120184 A1 | 5/2012 | Fornell et al. |
| 2012/0176470 A1 | 7/2012 | Zhang |
| 2012/0249802 A1 | 10/2012 | Taylor |
| 2012/0322413 A1 | 12/2012 | Haddad et al. |
| 2012/0327225 A1 | 12/2012 | Barley et al. |
| 2013/0063554 A1 | 3/2013 | Green et al. |
| 2013/0093904 A1 | 4/2013 | Wagner et al. |
| 2013/0120592 A1 | 5/2013 | Bednarczyk et al. |
| 2013/0189925 A1 | 7/2013 | Staskawicz et al. |
| 2013/0222583 A1 | 8/2013 | Earnshaw |
| 2013/0223279 A1 | 8/2013 | Tinnakornsrisuphap et al. |
| 2013/0235222 A1 | 9/2013 | Karn |
| 2013/0235226 A1 | 9/2013 | Karn |
| 2013/0337857 A1 | 12/2013 | Hassan et al. |
| 2014/0028435 A1 | 1/2014 | Brockway et al. |
| 2014/0028816 A1 | 1/2014 | Brockway et al. |
| 2014/0028817 A1 | 1/2014 | Brockway et al. |
| 2014/0028818 A1 | 1/2014 | Brockway et al. |
| 2014/0109184 A1 | 4/2014 | Parker |
| 2015/0009347 A1 | 1/2015 | O'Donnell et al. |
| 2021/0392263 A1 | 12/2021 | O'Donnell et al. |

FOREIGN PATENT DOCUMENTS

| | | |
|---|---|---|
| CN | 1470128 | 1/2004 |
| CN | 1628329 A | 6/2005 |
| CN | 1684500 A | 10/2005 |
| CN | 1728777 | 2/2006 |
| CN | 101150668 A | 3/2008 |
| CN | 102148923 A | 8/2011 |
| CN | 102413272 A | 4/2012 |
| CN | 101084817 A | 8/2012 |
| CN | 102082906 A | 4/2013 |
| DE | 19715321 | 10/1998 |
| DE | 10106072 | 8/2002 |
| DE | 202004001608 U1 | 5/2004 |
| EP | 0917359 A1 | 5/1999 |
| EP | 0980181 | 2/2000 |
| EP | 1638326 A1 | 3/2006 |
| EP | 1901553 | 3/2008 |
| EP | 1903782 A2 | 3/2008 |
| EP | 2184632 A2 | 5/2010 |
| EP | 2070322 A2 | 2/2011 |
| EP | 4007270 A1 | 6/2022 |
| FR | 2870365 A3 | 11/2005 |
| JP | 61-118076 | 6/1986 |
| JP | 06141308 | 5/1994 |
| JP | 08-223524 | 8/1996 |
| JP | H10164563 A | 6/1998 |
| JP | 2002-152371 | 5/2002 |
| JP | 2002-300238 | 10/2002 |
| JP | 2004-206707 | 7/2004 |
| JP | 2004-080256 A | 11/2004 |
| JP | 2005-118158 | 5/2005 |
| JP | 2006146542 | 6/2006 |
| JP | 2006-186904 | 7/2006 |
| JP | 2006-332970 | 12/2006 |
| JP | 2006-352540 | 12/2006 |
| JP | 2007-019644 A | 1/2007 |
| JP | 2007-081459 | 3/2007 |
| JP | 2007103091 | 4/2007 |
| JP | 2007-310815 | 11/2007 |
| JP | 2008-099176 | 4/2008 |
| JP | 2008-536443 | 9/2008 |
| JP | 2009-021914 | 1/2009 |
| WO | WO 96/38004 | 11/1996 |
| WO | WO 98/57300 | 2/1998 |
| WO | WO 2002/13522 A2 | 2/2002 |
| WO | WO 2004/023795 | 3/2004 |
| WO | WO 2006/071123 A1 | 7/2006 |
| WO | WO 2006/110109 | 10/2006 |
| WO | WO 2009/018391 | 2/2009 |
| WO | WO 2010/054245 A2 | 5/2010 |

OTHER PUBLICATIONS

Amended Complaint with Jury Demand (with Appendices) against GoPro, Inc. filed Feb. 19, 2016, *Contour IP Holding, LLC v. GoPro, Inc.* (involving U.S. Pat. No. 8,890,954 and U.S. Pat. No. 8,896,694), Case No. 3:17-cv-04738-WHO, 345 pages.

Amended Complaint (without Appendices) filed Jan. 5, 2015, *Contour, LLC v. GoPro, Inc.* (involving U.S. Pat. No. 8,890,954 and U.S. Pat. No. 8,896,694), Case No. 2:14-cv-00864-PMW, 20 pages.

Motion for Leave to Amend and Supplement First Amended Complaint and Supporting Memorandum (with Appendices) filed Feb. 17, 2015, *Contour, LLC v. GoPro, Inc.* (involving U.S. Pat. No.

(56) References Cited

OTHER PUBLICATIONS 8,890,954 and U.S. Pat. No. 8,896,694), Case No. 2:14/cv/00864/PMW, 150 pages.
Petition for Inter Partes Review of U.S. Pat. No. 8,890,954 filed Apr. 20, 2015, *GoPro, Inc.* v. *Contour, LLC*, Case No. IPR2015-01080, 69 pages.
GoPro Pamphlet (undated) and Jones Declaration (alleging GoPro Pamphlet was publicly distributed Jul. 2009) filed Apr. 20, 2015, Case Nos. IPR2015-01078, IPR2015-01080, 26 pages. Applicant requests the Examiner to consider the GoPro Pamphlet as qualifying prior art to the present application, but reserves the right to challenge the reference's prior art status at a later date.
Román, Expert Declaration for U.S. Pat. No. 8,890,954 and Curriculum Vitae filed Apr. 20, 2015, *GoPro, Inc.* v. *Contour, LLC*, Case No. IPR2015-01080, 122 pages.
Petition for Inter Partes Review of U.S. Pat. No. 8,896,694 filed Apr. 20, 2015, *GoPro, Inc.* v. *Contour, LLC*, Case No. IPR2015-01078, 66 pages.
Román, Expert Declaration for U.S. Pat. No. 8,896,694 and Curriculum Vitae filed Apr. 20, 2015, *GoPro, Inc.* v. *Contour, LLC*, Case No. IPR2015-01078, 112 pages.
Patent Owner's Preliminary Response and Exhibits, filed Jul. 30, 2015, *GoPro, Inc.* v. *Contour, LLC*, Case No. IPR2015-01080 (involving U.S. Pat. No. 8,890,954), 54 pages.
Patent Owner's Preliminary Response and Exhibits, filed Jul. 30, 2015, *GoPro, Inc.* v. *Contour, LLC*, Case No. IPR2015-01078 (involving U.S. Pat. No. 8,896,694), 50 pages.
Ex Parte Kennedy, Appeal No. 2008-1131 (BPAI Sep. 18, 2008), 9 pages.
Institution of Inter Partes Review Decision, dated Oct. 28, 2015, *GoPro, Inc.* v. *Contour, LLC*, Case No. IPR2015-01080 (involving U.S. Pat. No. 8,890,954), 29 pages.
Institution of Inter Partes Review Decision, dated Oct. 28, 2015, *GoPro, Inc.* v. *Contour, LLC*, Case No. IPR2015-01078 (involving U.S. Pat. No. 8,896,694), 27 pages.
Complaint (without Appendices) filed Nov. 30, 2015, *Contour IP Holding, LLC et al.* v. *GoPro, Inc.* (involving U.S. Pat. No. 8,890,954 and U.S. Pat. No. 8,896,694), Case No. 1:15-cv-01108-LPS-CJB, 24 pages.
Supplemental Declaration of Damon Jones, filed Dec. 30, 2015, *GoPro, Inc.* v. *Contour IP Holding, LLC*, Case Nos. IPR2015-01078/01080 (involving U.S. Pat. No. 8,896,694, U.S. Pat. No. 8,890,954), 8 pages.
Declaration of Richard Mander, filed Jan. 19, 2016, *GoPro, Inc.* v. *Contour IP Holding, LLC*, Case Nos. IPR2015-01078/01080 (involving U.S. Pat. No. 8,896,694, U.S. Pat. No. 8,890,954), 11 pages.
Patent Owner Response with Exs. 2005, 2007-2011, filed Jan. 19, 2016, *GoPro, Inc.* v. *Contour IP Holding, LLC*, Case No. IPR2015-01080 (involving U.S. Pat. No. 8,890,954), 68 pages.
Declaration of Brent Nelson, filed Jan. 19, 2016, *GoPro, Inc.* v. *Contour IP Holding, LLC*, Case No. IPR2015-01080 (involving U.S. Pat. No. 8,890,954), 68 pages.
Declaration of Brent Nelson, filed Jan. 19, 2016, *GoPro, Inc.* v. *Contour IP Holding, LLC*, Case No. IPR2015-01078 (involving U.S. Pat. No. 8,896,694), 65 pages.
Declaration of Michael P. Duffey, filed Jan. 19, 2016, *GoPro, Inc.* v. *Contour IP Holding, LLC*, Case No. IPR2015-01080 (involving U.S. Pat. No. 8,890,954), 5 pages.
Declaration of Michael P. Duffey, filed Jan. 19, 2016, *GoPro, Inc.* v. *Contour IP Holding, LLC*, Case No. IPR2015-01078 (involving U.S. Pat. No. 8,896,694), 5 pages.
Patent Owner Response with Exs. 2005, 2007-2011, filed Jan. 19, 2016, *GoPro, Inc.* v. *Contour IP Holding, LLC*, Case No. IPR2015-01078 (involving U.S. Pat. No. 8,896,694), 88 pages.
Deposition of Brent Nelson, filed Apr. 4, 2016, *GoPro, Inc.* v. *Contour IP Holding, LLC*, Case Nos. IPR2015-01078/01080 (involving U.S. Pat. No. 8,896,694, U.S. Pat. No. 8,890,954), 120 pages.
Deposition of Richard Mander, filed Apr. 4, 2016, *GoPro, Inc.* v. *Contour IP Holding, LLC*, Case Nos. IPR2015-01078/01080 (involving U.S. Pat. No. 8,896,694, U.S. Pat. No. 8,890,954), 131 pages.

Supplemental Declaration Kendyl A. Roman, filed Apr. 4, 2016, *GoPro, Inc.* v. *Contour IP Holding, LLC*, Case No. IPR2015-01080 (involving U.S. Pat. No. 8,890,954), 27 pages.
Supplemental Declaration of Kendyl A. Roman, filed Apr. 4, 2016, *GoPro, Inc.* v. *Contour IP Holding, LLC*, Case No. IPR2015-01078 (involving U.S. Pat. No. 8,896,694), 25 pages.
Petitioner Reply to Patent Owner's Response, filed Apr. 4, 2016, *GoPro, Inc.* v. *Contour IP Holding, LLC*, Case No. IPR2015-01080 (involving U.S. Pat. No. 8,890,954), 30 pages.
Petitioner Reply to Patent Owner's Response, filed Apr. 4, 2016, *GoPro, Inc.* v. *Contour IP Holding, LLC*, Case No. IPR2015-01078 (involving U.S. Pat. No. 8,896,694), 30 pages.
Petitioner's Trial Hearing Demonstrative Slides, filed Jun. 20, 2016, *GoPro, Inc.* v. *Contour IP Holding, LLC*, Case No. IPR2015-01078 (involving U.S. Pat. No. 8,896,694), 38 pages.
Patent Owner's Demonstratives, filed Jun. 20, 2016, *GoPro, Inc.* v. *Contour IP Holding, LLC*, Case No. IPR2015-01078 (involving U.S. Pat. No. 8,896,694), 39 pages.
GoPro's Answer to Complaint with Jury Demand, Counterclaims for Non-Infringement and Invalidity against Contour IP Holding, LLC, filed Dec. 7, 2017, *Contour IP Holding, LLC* v. *GoPro, Inc.*, Case No. 3:17-cv-04738-WHO, 15 pages.
Joint Claim Construction Chart (including Exhibit 1, Tabs C and D of Exhibit 2) by Contour IP Holding, LLC., filed Jun. 28, 2017, *Contour IP Holding, LLC* v. *GoPro, Inc.*, Case No. 3:17-cv-04738-WHO, 33 pages.
Joint Claim Construction and Prehearing Statement (including Exhibit A) by Contour IP Holding, LLC., filed Mar. 20, 2018, *Contour IP Holding, LLC* v. *GoPro, Inc.*, Case No. 3:17-cv-04738-WHO (involving U.S. Pat No. 8,890,954 and U.S. Pat No. 8,896,694), 17 pages.
Record of Oral Hearing, dated Jun. 22, 2016, *GoPro, Inc.* v. *Contour IP Holding, LLC*, Case No. IPR2015-01078 (involving U.S. Pat. No. 8,896,694), 92 pages.
Final Written Decision, entered Oct. 26, 2016, *GoPro, Inc.* v. *Contour IP Holding, LLC*, Case No. IPR2015-01080 (involving U.S. Pat. No. 8,890,954), 31 pages.
Final Written Decision, entered Oct. 26, 2016, *GoPro, Inc.* v. *Contour IP Holding, LLC*, Case No. IPR2015-01078 (involving U.S. Pat. No. 8,896,694), 32 pages.
Order Regarding Claim Construction issued by Judge William H. Orrick, Granting in Part Administrative Motion to File Under Seal, Jul. 16, 2018, *Contour IP Holding, LLC* v. *GoPro, Inc.*, Case No. 3:17-cv-04738-WHO (involving U.S. Pat No. 8,890,954 and U.S. Pat No. 8,896,694), 22 pages.
Federal Circuit Opinion (involving U.S. Pat No. 8,890,954 and U.S. Pat No. 8,896,694), *GoPro, Inc.* v. *Contour IP Holding LLC*, 898 F.3d 1170 (Fed. Cir.), issued Jul. 27, 2018, opinion modified and superseded, 908 F.3d 690 (Fed. Cir. 2018), and opinion withdrawn on denial of reh'g, 741 F. App'x 799 (Fed. Cir. 2018), 11 pages.
Federal Circuit Modified Opinion (involving U.S. Pat No. 8,890,954 and U.S. Pat No. 8,896,694), *GoPro, Inc.* v. *Contour IP Holding LLC*, 908 F.3d 690 (Fed. Cir. 2018), issued Nov. 1, 2018, opinion modifies and supersedes, 898 F.3d 1170 (Fed. Cir.), 11 pages.
Declaration of Michelle Ann Clark in Support of Defendant GoPro, Inc's Motion to Amend Patent L.R. 3-3 Invalidity Contentions, *Contour IP Holding, LLC* v. *GoPro, Inc.*, Case No. 3:17-cv-04738-WHO, 2019, 5 pages.
Exhibit A, Defendant's First Amended Invalidity Contentions, *Contour IP Holding, LLC* v. *GoPro, Inc.*, Case No. 3:17-cv-04738-WHO, Nov. 19, 2019, 30 pages.
Exhibit B, Chart for U.S. Pat. No. 8,890,954 in view of Smartvue S8/S9, *Contour IP Holding, LLC* v. *GoPro, Inc.*, Case No. 3:17-cv-04738-WHO, Nov. 19, 2019, 89 pages.
Exhibit C, Chart for U.S. Pat. No. 8,890,954 in view of Canon DSLR and Wireless File Transmitter, *Contour IP Holding, LLC* v. *GoPro, Inc.*, Case No. 3:17-cv-04738-WHO, Nov. 19, 2019, 65 pages.
Exhibit D, Chart for U.S. Pat. No. 8,890,954 in view of Axis, *Contour IP Holding, LLC* v. *GoPro, Inc.*, Case No. 3:17-cv-04738-WHO, Nov. 19, 2019, 64 pages.

(56) References Cited

OTHER PUBLICATIONS

Exhibit E, Chart for U.S. Pat. No. 8,890,954 in view of Panasonic, *Contour IP Holding, LLC v. GoPro, Inc.*, Case No. 3:17-cv-04738-WHO, Nov. 19, 2019, 76 pages.
Exhibit F, Chart for U.S. Pat. No. 8,890,954 in view of Sony, *Contour IP Holding, LLC v. GoPro, Inc.*, Case No. 3:17-cv-04738-WHO, Nov. 19, 2019, 71 pages.
Exhibit G, Chart for U.S. Pat. No. 8,896,694 in view of Smartvue S8/S9, *Contour IP Holding, LLC v. GoPro, Inc.*, Case No. 3:17-cv-04738-WHO, Nov. 19, 2019, 120 pages.
Exhibit H, Chart for U.S. Pat. No. 8,896,694 in view of Canon DSLR and Wireless File Transmitter, *Contour IP Holding, LLC v. GoPro, Inc.*, Case No. 3:17-cv-04738-WHO, Nov. 19, 2019, 97 pages.
Exhibit I, Chart for U.S. Pat. No. 8,896,694 in view of Axis Prior Art, *Contour IP Holding, LLC v. GoPro, Inc.*, Case No. 3:17-cv-04738-WHO, Nov. 19, 2019, 82 pages.
Exhibit J, Chart for U.S. Pat. No. 8,896,694 in view of Panasonic System, *Contour IP Holding, LLC v. GoPro, Inc.*, Case No. 3:17-cv-04738-WHO, Nov. 19, 2019, 141 pages.
Exhibit K, Chart for U.S. Pat. No. 8,896,694 in view of Sony, *Contour IP Holding, LLC v. GoPro, Inc.*, Case No. 3:17-cv-04738-WHO, Nov. 19, 2019, 134 pages.
Exhibit O, Before the Patent Trial and Appeal Board: Patent Owner's Submission Regarding Claim Construction, *Contour IP Holding, LLC v. GoPro, Inc.*, Case No. 3:17-cv-04738-WHO, Nov. 19, 2019, 6 pages.
Exhibit X, Chart for U.S. Pat. No. 8,896,694 in view of Vidcie/Looxcie, *Contour IP Holding, LLC v. GoPro, Inc.*, Case No. 3:17-cv-04738-WHO, Nov. 19, 2019, 155 pages.
Exhibit W, Chart for U.S. Pat. No. 8,890,954 in view of Vidcie/Looxcie, *Contour IP Holding, LLC v. GoPro, Inc.*, Case No. 3:17-cv-04738-WHO, Nov. 19, 2019, 85 pages.
Order on Motions for Summary Judgment and to Exclude, *Contour IP Holding, LLC, v. GoPro, Inc.*, Case Nos. 3:17-cv-04738-WHO, 3:21-cv-02143-WHO, Mar. 4, 2022, 15 pages.
Plaintiff Contour IP Holding, LLC's Reply in Support of Its Motion for Summary Judgment, Redacted, *Contour IP Holding, LLC v. GoPro, Inc.*, Case Nos. 17-cv-04738-WHO, 21-cv-02143-WHO, Jan. 18, 2022, 20 pages.
GoPro's Motion for Summary Judgment, *Contour Holding, LLC v. GoPro, Inc.*, Case Nos. 17-cv-04738-WHO, 21-cv-02143-WHO, Dec. 17, 2021, 30 pages.
Plaintiff Contour IP Holding, LLC's Motion for Summary Judgment, Redacted version of document filed under seal, Case Nos. 17-cv-04738-WHO, 21-cv-02143-WHO, Dec. 16, 2021, 32 pages.
GoPro's Response to Plaintiff's Statement Regarding Discovery Dispute Concerning Deposition of Fortress Investment Group, LLC, Case Nos. 17-cv-04738-WHO, 21-cv-02143-WHO, Dec. 7, 2021, 7 pages.
Defendant GoPro, Inc.'s Administrative Motion to File Under Seal Portions of Its Response to Plaintiff's Statement Regarding Discovery Dispute Concerning Deposition of Fortress Investment Group, LLC, Case No. 17-cv-04738-WHO, Dec. 7, 2021, 3 pages.
Joint Statement Regarding Discovery Dispute Concerning Dr. Almeroth's Looxcie Invalidity Theory, Case Nos. 17-cv-04738-WHO, 21-cv-02143-WHO, Nov. 18, 2021, 9 pages.
GoPro's First Amended Answer and Counterclaims to Plaintiff's Complaint, Case Nos. 17-cv-04738-WHO, 21-cv-02143-WHO, Nov. 11, 2021, 22 pages.
Defendant GoPro, Inc.'s Reply in Support of Its Motion for Leave to File an Amended Answer, Case Nos. 17-cv-04738-WHO, 21-cv-02143-WHO, Oct. 25, 2021, 14 pages.
Defendant GoPro, Inc.'s Notice of Motion and Motion for Leave to File an Amended Answer, Case Nos. 17-cv-04738-WHO, 21-cv-02143-WHO, Oct. 4, 2021, 9 pages.
Order on Motion to Strike, Motion for Judgment on the Pleadings, and Claim Construction, Case Nos. 17-cv-04738-WHO, 21-cv-02143-WHO, Sep. 13, 2021, 23 pages.

Plaintiff Contour IP Holding, LLC's Reply Claim Construction Brief, Case Nos. 17-cv-04738-WHO, 21-cv-02143-WHO, Aug. 12, 2021, 18 pages.
Defendant GoPro, Inc.'s Responsive Claim Construction Brief, Case Nos. 17-cv-04738-WHO, 21-cv-02143-WHO, Aug. 5, 2021, 31 pages.
Defendant GoPro, Inc.'s Reply in Support of Its Motion for Judgment on the Pleadings Based on Section 101, Case Nos. 17-cv-04738-WHO, 21-cv-02143-WHO, Jul. 26, 2021, 21 pages.
Plaintiff Contour IP Holding, LLC's Opening Claim Construction Brief, Case Nos. 17-cv-04738-WHO, 21-cv-02143-WHO, Jul. 22, 2021, 28 pages.
Defendant GoPro, Inc.'s Notice of Motion and Motion for Judgment on the Pleadings Based on Section 101, and Memorandum of Points of Authorities in Support Thereof, Case Nos. 17-cv-04738-WHO, 21-cv-02143-WHO, Jun. 30, 2021, 26 pages.
X170 Action Camera and Mounts, http://www.actioncameras.co.uk/X170, accessed Nov. 2, 2009, 4 pages.
Oregon Scientific—ATC 9000, http:/www.helmkameras24.de/Oregon-Scientific-ATC-9000_c25 . . . , accessed Nov. 2, 2009, 2 pages.
96NBL-C230 2.4 GHz Wireless Network Camera User Manual 1 Panasonic downloaded from https://fccid.io/ACJ96NBL-C230/User-Manual/Users-Manual-1-1203640, on Mar. 16, 2021.
Ambarella Product Brief, A5s—1080p30 IP Camera SoC, Santa Clara, No date provided.
Ambarella Product Brief, A7—Hybrid DV/DSC 1080p60 Camera SoC, Santa Clara, No date provided.
Ambarella Product Brief, A7—1050p60 IP Camera SoC, Santa Clara, No date provided.
Ambarella Company Fact Sheet, 2014, Santa Clara, 2014.
Ambarella A5 Hybrid Camera Platform puts High Quality Photos and Video on a Chip, www.ambarella.com. retrieved from the Internet on Jul. 3, 2014: http://www.ambarella.com/news/8/74/Ambarella-A5-Hybrid-Camera-Platform-puts-High-Quality-Photos-and-Video-on-a-Chip, Jan. 5, 2009, Santa Clara.
Ambarella A5s With High-Speed CPU and low-Power 45nm Technology Makes Pocket-Sized Hybrid Cameras a Richer User Experience, www.ambarella.com. retrieved from the Internet on Jul. 3, 2014: http://www.ambarella.com/news/7 17 41 Am barella-A5s-with-High-Speed-CPU-and-low-Power-45n m-Technology-Makes-Pocket-Sized-Hybrid-Cameras-a-Richer-User-Experience, Jan. 7, 2010, Santa Clara.
Ambarella A5s IP Camera Platform Delivers Industry-Changing Combination of Image Quality, HD H.264 Multi-streaming, CPU Flexibility, and low Power Consumption, www.ambarella.com. retrieved from the Internet on Jul. 3, 2014: http://www.ambarella.com/news/6/74/Ambarella-A5s-IP-camera-platform-delivers-industry-changing-combination-of-image-quality-HD-H-264-multi-streaming-CPU-flexibility-and-low-power-consumption, Mar. 16, 2010, Santa Clara.
Ambarella A7 System-On-Chip Sets New Benchmarks for High-Resolution Video and Image Quality in Consumer HD Cameras, www.ambarella.com. retrieved from the Internet on Jul. 3, 2014: http://www.ambarella.com/news/20/741Ambarella-A7-system-on-chip-sets-new-bench marks-for-high-resolution-video-and-image-quality-in-consumer-HD-cameras, Sep. 27, 2010, Santa Clara.
Ambarella A7 IP Camera SoC Brings 1080p60 Performance into the Video Surveillance Mainstream, www.ambarella.com. retrieved from the Internet on Jul. 3, 2014: http://www.ambarella.com/news/24/741Ambarella-A7-IP-Camera-SoC-Brings-1080p60-Performance-into-the-Video-Surveillance-Mainstream, Mar. 31, 2011, Santa Clara.
Ambarella A7l Enables the Next Generation of Digital Still Cameras with 1080p60 Fluid Motion Video, www.ambarella.com. retrieved from the Internet on Jul. 3, 2014: http://www.ambarella.com/news/26/74/Ambarella-A7I-Enables-the-Next-Generation-of-Digital-Still-Cameras-with-1080p60-Fluid-Motion-Video, Sep. 26, 2011, Santa Clara.
Apollo Communication Systems Section Flight Control Operations Branch Flight Control Division, "Lunar Surface Television Operations Plan", Jul. 5, 1971, Manned Spacecraft Center, Houston, Texas, GoPro_201722.
"Apple iPhone 4 review", published Aug. 9, 2010, retrieved Mar. 16, 2021 from https://www.whathifi.com/apple/iphone-4/review.

(56) References Cited

OTHER PUBLICATIONS

Bhat, "Panasonic Ip Camera Setup Par 1.flv", Feb. 16, 2010 available at https://www.youtube.com/watch?v=MjgeiIL5wZA as archived Mar. 16, 2021.
Bhat, "Panasonic Ip Camera Setup Part 2.flv", Feb. 16, 2020 available at https://www.youtube.com/watch?v=aiwqWB72bGY as archived Mar. 16, 2021.
Bhat, "Panasonic Ip Camera Setup Part 3.flv", Feb. 16, 2020 available at https://www.youtube.com/watch?v=I97q9t2olbA, as archived Mar. 16, 2021.
"Bluetooth vs AirPlay: What's the Difference?", retrieved Mar. 16, 2021 from https://www.cambridgeaudio.com/usa/en/blog/difference-between-airplay-bluetooth.
Buchannan, "Canon 7D DSLR First Hands on: 18 Megapixels, 24FPS Full HD Video for $1900", published Sep. 1, 2009, retrieved Mar. 16, 2021 from https://gizmodo.com/canon-7d-dslr-first-hands-on-18-megapixels-24fps-full-5349829.
Canon, EOS 7D, downloaded from https://www.usa.canon.com/internet/portal/us/home/support/details/cameras/eos-dslr-and-mirrorless-cameras/dslr/eos-7d?tab=manuals.
Canon, "Wireless File Transmitter WFT-E5A" downloaded from https://www.usa.canon.com/internet/portal/us/home/products/details/cameras/wireless-file-transmitters-and-adapters/wireless-file-transmitter-wft-e5a.
Canon, Wireless File Transmitter WFT-E5 downloaded from http://gdlp01.c-wss.com/gds/8/0300004158/01/wft-e5-en.pdf, 132 pages.
Cesa, Dante, Contour Brings Viewfinder App to Android, Goes With you Where We Won't, retrieved from the Internet on Jul. 3, 2014: http://www.engadget.com/2011/07/20lcontours-connect-brings-viewfinder-app-to-android-goes-with-yol, Jul. 20, 2011.
Christopherkblog, "Canon EOS 7D—Basic Wireless File Transmitter Capabilities and Possibilities 16/16", Nov. 30, 2009 available at https://www.youtube.com/watch?v=nG5oKcQ0HA8 as archived Mar. 16, 2021.
Christopherkblog, "Canon EOS 7D—Wireless File Transmitter WFT-E5 6/8", Oct. 16, 2009 available at https://www.youtube.com/watch?v=ptrc5eWFP0I as archived Mar. 16, 2021.
Cision PR Newswire, downloaded from https://www.prnewswire.com/news-releases/smartvue-wins-2010-mobility-award-89100277.html, Mar. 25, 2010.
Clough, "First impressions: Hands on with Apple AirPlay", published Nov. 24, 2010, retrieved Mar. 16, 2021 from https://www.whathifi.com/news/first-impressions-hands-apple-airplay.
Coan, Paul P., "Apollo Experience Report—Television System", Nov. 1973, GoPro_201688.
EDN, "Menacingly Beautiful Video Surveillance Server Launched by Smartvue Corporation" downloaded from https://www.edn.com/menacingly-beautiful-video-surveillance-server-launched-by-smartvue-corporation/, Aug. 31, 2010.
"EOS 7D Press Release", published Aug. 31, 2009, retrieved Mar. 16, 2021 from https://www.canonrumors.com/eos-7d-press-release/.
Grabham et al., "History of the iPhone 2007-2017: the journey to iPhone X", published Jan. 10, 2018, retrieved Mar. 16, 2021 from https://www.t3.com/us/features/a-brief-history-of-the-iphone.
Greenwald, Will, "Looxcie HD Explore Review," downloaded from https://www.pcmag.com/reviews/looxcie-hd-explore, Mar. 1, 2013.
Hart, Home Security and the Panasonic BL-C230:, Nov. 19, 2010 available at https://www.youtube.com/watch?v=yYnrXcpV2Tk as archived Mar. 16, 2021.
Holly, Russel, "Review: Looxcie 2 personal video recorder," downloaded from https://web.archive.org/web/20161221022338/https://www.geek.com/gadgets/review-looxcie-2-personal-video-recorder-1436689/, Mar. 11, 2011.
"Interchangeable Lens Digital Cameras" dated Oct. 2009, retrieved Mar. 16, 2021 from https://global.canon/en/c-museum/product/dslr802.html.
Lebar, Stanley, "The Color War Goes to the Moon", Invention & Technology, 1997, pp. 52, 54, GoPro_201604.
Lebar, Stanley and Hoffman, Charles P., "TV Show of the century: A Travelogue with no atmosphere", Westinghouse Technical Information: Reprint 6437, 1976, GoPro_202874.
"Lebar—Final Copy, Lunar TV Camera", Exhibit A: Statement of Work, Aug. 15, 1966, 70 pages, GoPro_203198.
Looxcie, Inc., "Looxcie launches the Looxcie 2 Wearable Camcorder," downloaded from https://www.prnewswire.com/news-releases/looxcie-launches-the-looxcie-2-wearable-camcorder-123341548.html, Jun. 7, 2011.
Looxcie 2 and Looxcie HD Product Overviews downloaded from https://www.adorama.com/alc/0014300/article/Looxcie-2-and-Looxcie-HD-Product-Overviews, downloaded on Mar. 16, 2021.
Looxcie 2 User Manual for Android Model: LX2, downloaded from https://www.bhphotovideo.com/lit_files/45530.pdf, 2011.
MacLeay, Alicia, "Outdoor Retailer: Day One Notes", Trailspace.com, http://www.trailspace.com/blog/2009/07/22/outdoor-retailer-da . . . , Jul. 22, 2009, 2 pages, VERDEPR000777.
Molla, "How Apple's iPhone changed the world: 10 Years in 10 charts", published Jun. 26, 2017, retrieved Mar. 16, 2021 from https://www.vox.com/2017/6/26/15821652/iphone-apple-10-year-anniversarylaunch-mobile-stats-smart-phone-steve-jobs.
Photograph and drawing of a Midland Radio goggle mount for a camera. The photograph was taken at the CES Trade Show, Jan. 2010.
Photograph and drawing of a Midland Radio goggle mount for a camera with a plug mount inserted into the goggle mount and a camera showing in the foreground. The photograph was taken at the CES Trade Show Jan. 2010.
Drawing of subject matter from a print out from an Internet website: https://www.midlandradio.comIResourceJProductI1390/Detail/LargeImage/Goggle%20Mou . . . , Oct. 18, 2010. The website printout was previously submitted as reference CN.
Goodwin, Antuan, App Unlocks Bluetooth Viewfinder on ContourGPS, cnet.com, retrieved from the Internet on Jul. 13, 2014: http://www.cnet.com/news/app-unlocks-bluetooth-viewfinder-on-contourgpsl, Jan. 5, 2011.
GoPro Outdoor Retailer Summer Market 2009 Press Kit, 29 pages, GoPro_12849.
"GoPro HD Hero—A High Def Helmet Cam at 1080P—Sample Videos", http://helmentcameracentral.com/2009/07/22/gopro-hd-high-def-., Jul. 22, 2009, printed on Oct. 6, 2009, 8 pages, VERDEPR000769.
Gorman, Michael, ContourRoam2 Debuts in Red, Blue, Green and Black Garb, Shoots 1080p video for $199 on Oct. 21, retrieved from the Internet on Jul. 3, 2014: http://www.engadget.com/2012/10/16/contour-roam2-action-camera/, Oct. 16, 2012.
H.B.C., Contour GPS HD Video Camera Review, webBikeWorld.com, retrieved from the Internet on Jul. 3, 2014: http://www.webbikeworld.com/r4/contour-gps-hd-video-cameral, Jun. 2011.
Happich, Julien, Ambarella targets pocket-sized hybrid cameras with its A5s SoCs, eetimes.com, retrieved from the Internet on Jul. 17, 2014: http://www.eetimes.com/document.asp?doc_id=1270493. 1/712010, Cambridge, UK.
"History of Apple AirPlay . . . We Mean AirTunes", retrieved Mar. 16, 2021 from https://backtracks.fm/blog/history-of-apple-airplay/.
"How to go wireless—setting up FTP with the WFT-E4" downloaded from http://blog.julianlove.com/2009/02/how-to-go-wireless-setting-up-ftp-with.html, Feb. 23, 2009.
O'Kane, "The Gigtube, Wireless Digital Viewfinder", Sep. 25, 2011 available at https://web.archive.org/web/20210316204535/https://www.youtube.com/watch?v=8IB5snXyhSI as archived Mar. 16, 2021.
"Official EOS 7D press releases from Canon USA", dated Sep. 1, 2009, retrieved Mar. 16, 2021 from https://www.dvinfo.net/forum/canon-eos-crop-sensor-hd/346234-official-eos-7d-press-releasescanon-usa.html.
Ostendorp, Ryan, GoPro Launches First True HD Wearable Sports Camera, Aug. 12, 2009, https://www.snewsnet.com/press-release/gopro-launches-the-first-true-hd-wearable-sports-camera, 6 pages, GoPro_12832.
Outdoor Industry Association, GoPro Launches the First True HD Wearable Sports Camera—The HD Helmet Hero, Jul. 20, 2009,

(56) References Cited

OTHER PUBLICATIONS https://outdoorindustry.org/press-release/gopro-launches-the-first-true-hd-wearable-sports-camera-the-hd-helmet-hero/, 7 pages, GoPro_12825.
Panasonic Setup Guide Network Camera Model No. BL-C210, BL-C230 downloaded from http://pdfstream.manualsonline.com/0/093bd833-9f7e-494e-9bc1-efddc2f955cd.pdf, on Mar. 16, 2021.
Panasonic Setup Guide Network Camera Model No. BL-C210, BL-C230 downloaded from https://usermanual.wiki/Panasonic/BLC230.1115449120/view, on Mar. 16, 2021.
Panasonic BL-230A—Wireless Network Camera Support page downloaded from https://shop.panasonic.com/support-only/BL-C230A.html, on Mar. 16, 2021.
Panasonic BL-C230A Wireless Internet Security Camera downloaded from https://www.amazon.com/Panasonic-BL-C230A-Wireless-Internet-Security/dp/B002JM5JSU, on Mar. 16, 2021.
"Panasonic BL-C230A Installation Manual" available on https://web.archive.org/web/20140311063508/https://www.manualslib.com/manual/403281/Panasonic-BI-C230a.html as archived on Mar. 16, 2021.
"Panasonic introduces pair of low-cost IP network cameras", published Jan. 11, 2010, retrieved Mar. 16, 2021 from https://www.videosurveillance.com/blog/brands/panasonic_introduces_pair_of_lowcost_ip_network_cameras.asp.
Panasonic, Important Information, Model No. BL-C210, BL-C230, 2 pages.
Panasonic, Installation Guide, Model No. BL-C230, 4 pages.
Panasonic, Network Camera Comparison Chart, Oct. 2010, 6 pages.
Rainbow Guitar webpage for Dual Channel Camera mount Wireless Microphone available at http://www.rainbowguitars.com/live-sounds/audio-technical/atw-1823-dual-channel-camera-mount-wireless-system/ATW1823D/AT, date visited May 2, 2013.
Rehn et al., "Canon EOS 7D Review", published Nov. 6, 2009, retrieved Mar. 16, 2021 from https://www.dpreview.com/reviews/canoneos7d.
Roth, Cliff, Video and Still Camera-On-Chip Platform From Ambarella Records Two Resolutions Simultaneously, eetimes.com, retrieved from the Internet on Jul. 3, 2014: http://www.eetimes.com/document.asp?doc id=1311224, Jan. 5, 2009, Santa Clara.
Rowse, Darren, "Canon EOS 7D", downloaded from https://digital-photography-school.com/canon-eos-7d/.
Russ, "Panasonic BL-C230A Wireless IP Camera With Extra Bells & Whistles" downloaded from https://www.gadgetking.com/2010/06/07/panasonic-bl-c230a-wireless-ip-camera-with-extra-bells-whistles/, Jun. 7, 2010.
Russell, Sam, "Shooting the Apollo Moonwalks, A recollection of how it was done", GoPro_201606.
Smarthome webpage for Remote Control Camera Pan Base Surveillance Camera Accessory available Mar. 23, 2009 at http://web.archive.org/web/20090323032932/http://www.smarthome.com/76006/Remote-Control-Camera-Pan-Base-Surveillance-Camera-Accessory/p.aspx, date visited May 2, 2013.
Smartvue S8 User Guide, 2009, available online from www.Manualslib.com, 96 pages, GoPro_13472.
Smartvue S9C1/S9C2 HD Network Camera User's Manuel, available online from www.smartvue.com, 119 pages, GoPro_14475.
Smartvue S9 User Guide, 2010, available online from www.Manualslib.com, 65 pages, GoPro_14599.
Smartvue, "Smartvue Launches S9 Surveillance" downloaded from https://www.prnewswire.com/news-releases/smartvue-launches-s9-surveillance-88895252.html, Mar. 23, 2010.
"SmartVue S8 Surveillance System lets you watch from anywhere" downloaded from https://www.gadgetmeter.com/2009/04/27/smartvue-s8-surveillance-system-lets-you-watch-from-anywhere/, Apr. 27, 2009.
Sony Handycam Handbook HDR XR520VE (copyright year shown as 2009, but no publication date provided), 136 pages. Applicant requests the Examiner to consider this reference as qualifying prior art to the present application, but reserves the right to challenge the reference's prior art status at a later date.
Sony SNC-RX Series, "Intelligent and Feature Rich—Sony High-Performance Multi-Code Network Cameras Deliver Efficient 24/7 Monitoring", Feb. 2010, 8 pages, GoPro_17138.
Sony SNC-RX550N, "The High-Performance Network Camera With 360-Degree Endless Rotation Delivers Efficient 24/7 Monitoring Operation—Anytime, Anywhere, Anyplace", Dec. 2005, 8 pages, GoPro_17212.
Sony SNC-RZ50N, "With its Feature Rich and Compact Design, the SNC-RZ50N PTZ Camera Is Ideal for a Wide Range of Monitoring Applications", Dec. 2005, 8 pages, GoPro_17220.
Sony SNZ-RZ50P, Intelligent All-in-one IP network camera with integrated pan/tilt/zoom, www.pro.sony.eu/videosecurity, 3 pages, GoPro_17228.
Sony SNC-CS50N/CS50P Network Camera User's Guide, Software Version 1.0, 2005, 87 pages, GoPro_17253.
Sony SNC-RX Series SNC-RZ50N/RZ50P SNC-CS50N/CS50P, Nov. 2009, 8 pages, GoPro_17388.
Sony, Quick Reference "IP Rapid Dome and PTZ Cameras", May 2010, GoPro_17396.
Sony SNC RZ50N/RZ50P Network Camera User's Guide, Software Version 2.2, 2005, 120 pages, GoPro_17432.
Software: Firmware for SNC-RZ50N/RZ50P (Ver.2.43), Jul. 8, 2010, https://pro.sony/en_CG/product-resources/software-firmware/1237493467419, printed on Nov. 4, 2019, 2 pages, GoPro_17572.
"Sony SNCRZ50P Network Security Camera", https://www.sovereigncctv.com/sony-sncrz50p-network-ptz-security-camera-clearance-3608.html, printed on Nov. 5, 2019, 3 pages, GoPro_17673.
"Sony SNC-RZ50N 640×480 MAX Resolution RJ45 Surveillance Camera", https://www.newegg.com/sony-snc-rz50n-ptz-camera/p/N82E16826159069, printed on Nov. 4, 2019, 3 pages, GoPro_17689.
"Sony, SNC-RZ50N.b Sony Day/Night Network Camera—Refurbished" https://www.surveillance-video.com/snc-rz50n-r.html, printed on Nov. 4, 2019, 6 pages, GoPro_17716.
Sony, Sony_Network_Security_Cameras_Technical_information_Video_for_the_SNC-RX550_SNC-RZ50_SNC-CS50 .wmv, Nov. 17, 2010 as available at https://web.archive.org/web/20210316215312/https://www.youtube.com/watch?v=KYLoTOeOAIU as archived on Mar. 16, 2021.
Sony SNC-RX550N/B Multi Codec PTZ Network Camera-Black (SNCRX550N/B) downloaded from https://smile.amazon.com/Sony-SNC-RX550N-Multi-Network-Camera/dp/B006G26BCW/ref=sr_1_1?crid=3SST4WCPZ64FD&keywords=sncrx550n&qid=1582141203&sprefix=snc-rx%2Caps%2C149&sr=8-1; on Mar. 16, 2021.
Sony Network Camera, SNC-RX series, Connect Your Vision IPELA brochure downloaded from https://www.useip.co.uk/datasheets/datasheet_732.pdf, on Mar. 16, 2021.
Sony SNC-RZ50N 640×480 Max Resolution RJ45 Surveillance Camera Overs from Newegg.com downloaded from https://www.newegg.com/sony-snc-rz50nptz-camera/p/N82E16826159069 on Mar. 16, 2021.
Specifications—Sony SNC-RX SNC RZ50 User Manual, www.manualsdir.com/manuals/138563/sony-snc-rx-snc-rz50-snc-cs50.html?page=8, printed Nov. 4, 2019, 4 pages, GoPro_17788.
"Comparison photographs of the Apollo 11 Lunar Television as seen at Goldstone, Honeysuckle Creek, Parkes and Houston", 20 pages, GoPro_201582.
"Severe Tire Damage, The Internet's First Live Band", published 2013, retrieved Mar. 16, 2021 from https://vimeo.com/56349011.
"Severe Tire Damage Played the First Live Music Performance on the Internet", retrieved Mar. 16, 2021 from https://www.std.org/text/live.html.
Sparkfun web page for Reed Switch available Aug. 30, 2009 at http://web.archive.org/web/20090831142518/http://www.sparkfun.com/commerce/product_info.php?products_id=8642, date visited May 2, 2013.
Srinivasan, "Blue-tooth enabled phone can act as wireless web cam", IBN Live. retrieved online on Mar. 25, 2010 from: http://ibnlive.in.com/news/bluetooth-enabledphone-can-act-as-wireless-web-cam/45790-11. html, Jul. 28, 2007, pp. 1-3.

(56) References Cited

OTHER PUBLICATIONS

Stevens, Tim, Contour Adds Live Viewfinder to its ContourGPS Helmet Cam, Real-Time Streaming to Smartphones, retrieved from the Internet on Jul. 3, 2014: http://www.engadget.com/2011101105/contour-adds-live-viewfinder-to-its-contourgps-helmet-cam-reali, Jan. 5, 2011.
Stevens, Tim, Contour Announces 1080p ContourGPS helmetcam, Lets Friends Locate Your Extreme Exploits (video), retrieved from the Internet on Jul. 3, 2014: http://www.engadget.com/2010109/13/contour-announces-1080p-contourgps-helmetcam-lets-friends-locat/, 2011.
System Produced for Inspection—Canon EOS 7D Camera, GoPro_207226.
System Produced for Inspection—Looxcie and Samsung Phone, GoPro_207219.
System Produced for Inspection—Looxcie HD Video Cam, GoPro_207216.
System Produced for Inspection—Looxcie Wearable Camcorder, GoPro_207214.
System Produced for Inspection—Looxcie Wearable Camcorder, GoPro_207215.
System Produced for Inspection—Looxcie, GoPro_207213.
System Produced for Inspection—Panasonic BL C2301A, GoPro_207212.
System Produced for Inspection—Smartvue S9C1, GoPro_207211.
"The First Live Stream is 20 Years Old", last updated Nov. 24, 2017, retrieved Mar. 16, 2021 from https://www.monitis.com/blog/the-first-live-stream-is-20-years-old/.
Toshiba Network Camera Model: IK-WB16A/IK-WB16A-W User's Manual, available online from www.toshiba.com, 120 pages, GoPro_13869.
Video Surveillance Blog downloaded from https://www.videosurveillance.com/blog/brands/smartvue-1/smartvue_s8_network_camera_system_set_for_january_release.asp, Sep. 26, 2008.
Twenty20 VHoldR Helmet Camera—Press Release, retrieved from the Internet on Jul. 15, 2014: http://helmetcameracentral.com/2007/08/08/twenty20-kills-the-helmet-cam-with-vholdr-%E2%80%93-the-next-gen-wearable-camcorder/, Aug. 8, 2007, Seattle, WA.
Viewer, "Sony SNC-P1—Cam Viewer for Sony cameras", Nov. 22, 2012 available at https://www.youtube.com/watch?v=j1CV7psTAol as archived Mar. 16, 2021.
Viewer, "Sony SNC-RX550P—Cam Viewer for Sony cameras", Nov. 22, 2012 available at https://www.youtube.com/watch?v=CcoE4y1nRMo archived Mar. 16, 2021.
Viewer, "Sony SNC-CS50—Cam Viewer for Sony cameras", Jan. 13, 2014 available at https://www.youtube.com/watch?v=5ZQfA023K0E archived on Mar. 16, 2021.
Webpage for Canon RC 5 Wireless Controller, available Aug. 5, 2010 at http://web.archive.org/web/20111210052722/http://www.amazon.com/Canon-RC-5-Wireless-Controller-Digital/dp/B00004WCCO, date visited May 2, 2013.
Webpage for E-Benk automatic pan tilt tripod with remote control, available May 22, 2009 at http:/web.archive.org/web/20121006050738/http://www.amazon.com/eBenk-Automatic-Tripod-Remote-Control/dp/B000KNMGR2, date visited May 2, 2013.
Webpage for Eye.fi, available May 9, 2009 at http://web.archive.org/web/20090509001848/http://www.eye.fi/cards/, date visited May 2, 2013.
Webpage for Mobile Air Mouse available Mar. 23, 2009 at http://web.archive.org/web/20090323060354/http://www.mobileairmouse.com/, date visited May 2, 2013.
Westinghouse, "Westinghouse TV Cameras Bring Apollo Video From Liftoff to Lunar Landscape", 14 pages, GoPro_202527.
Wetmore, Warren C. "Docking Transmitted Live in First Color TV from Space", Aviation Week & Space Technology, May 26, 1969, pp. 18, 20, GoPro_202765.
Wikipedia, "History of the iPhone", page last edited Mar. 8, 2021, retrieved Mar. 16, 2021 from https://en.wikipedia.org/wiki/History_of_iPhone.
Wikipedia, "AirPlay", page last edited Mar. 16, 2021, retrieved Mar. 16, 2021 from https://en.wikipedia.org/wiki/AirPlay.
"WFT Utility 3.5 for Windows", dated Dec. 17, 2009, retrieved Mar. 16, 2021 from https://asia.canon/en/support/0200099502/1.
Wowza Community, Using a Sony SNC-RZ50 internet camera downloaded from https://www.wowza.com/community/questions/475/using-a-sony-snc-rz50-internetcamera.html, on Mar. 16, 2021.
ZoneMinder Forums for Sony SNC-RZ50 working control script downloaded from https://forums.zoneminder.com/viewtopic.php?t=10995, on Mar. 16, 2021.
Xegis Electronic Group, Inc., Sony SNC-RZ50N (SNCRZ50N)—APTZ Camera that Accessorizes, Mar. 16, 2021, 5 pages.
Video Surveillance, "Smartvue S8 IP camera system to be showcased at ISC West" Mar. 6, 2008, available at https://web.archive.org/web/20080311102118/http://www.videosurveillance.com/blog/products/smartvue/smartvue_s8_ip_camera_system_to_be_showcased_at_isc_west.html (archived Mar. 11, 2008) ("Smartvue S8 Showcase").
CR80news, "ISC West 2008," available at https://www.cr80news.com/news-item/isc-west-2008/ ("ISC West 2008").
Smartvue, "Smartvue Technical Support Smartvue for iPhone," available at https://web.archive.org/web/20090125074410/http://smartvue.com/html/iphone_support.htm (archived Jan. 25, 2009) ("Smartvue for iPhone").
Smartvue, "InsightServer—Peer to Peer Network Video Surveillance Platform," available at https://web.archive.org/web/20090403073243/http://www.smartvue.com/html/insightserver_peer_to_peer_n.html (archived Apr. 3, 2009) ("InsightServer").
Smartvue, "Smartvue for iPhone," available at https://web.archive.org/web/20090126180823/http://smartvue.com:80/html/iphone.htm (archived Jan. 26, 2009) ("Smartvue for iPhone").
Smartvue, "Smartvue S8 Camera Technical Specifications," available at https://web.archive.org/web/20090702061934/http://smartvue.com/html/smartvue_s8_camera_technical_s.html (archived Jul. 2, 2009) ("S8 Camera Technical Specifications").
Smartvue, "Smartvue S8 Dome Camera Technical Specifications," available at https://web.archive.org/web/20090428105529/http://www.smartvue.com/html/smartvue_s8_dome_camera_techni.html (archived Apr. 28, 2009) ("S8 Dome Camera Technical Specifications").
Smartvue, "Smartvue HD Video Surveillance Solutions," available at https://slideplayer.com/slide/5837198/ ("Smartvue Slides").
Smartvue, "Store Buy online now at SmartvueDirect or through an Authorized Dealer," available at https://web.archive.org/web/20100826085414/http://www.smartvue.com/store.html (archived Aug. 26, 2010) ("Smartvue Store").
Smartvue, "Mobile Surveillance," available at https://web.archive.org/web/20100409115825/http://www.smartvue.com/mobile.html (archived Apr. 9, 2010) ("Mobile Surveillance").
Smartvue, "Smartvue Mobile Surveillance APP Third Party Cameras," available at https://web.archive.org/web/20100410213636/http://www.smartvue.com/third_party_cameras.html (archived Apr. 10, 2010) ("Third Party Cameras").
Smartvue, "On Demand Surveillance," available at https://web.archive.org/web/20100410184007/http://www.smartvue.com/on_demand_surveillance.html (archived Apr. 10, 2010) ("On Demand Surveillance").
Toshiba, "IK-WB16A/IK-WB16A-W Data Sheet," 2010, available at https://web.archive.org/web/20110409081741/http://www.toshibasecurity.com/pdf/_datasheets/IKWB16A_ds.pdf (archived Apr. 9, 2011) ("IK-WB16A/IK-WB16A-W Data Sheet").
Toshiba, "IP Camera Accessories," 2010, available at https://web.archive.org/web/20101105060607/http://www.toshibasecurity.com/pdf/AccessoriesMatrix.pdf (archived Nov. 5, 2010) ("Toshiba Accessories").
Toshiba, "Surveillance and IP Video Products," available at https://web.archive.org/web/20101123030533/http://www.toshibasecurity.com/ (archived Nov. 23, 2010) ("Toshiba Surveillance Products").
Toshiba, "IK-WB16A/IK-WB16A-W, Wired or wireless Pan/Tilt Network Camera," available at https://web.archive.org/web/20101107015618/http://www.toshibasecurity.com:80/products/prod_camera_detail_ikwb16a.jsp (archived Nov. 7, 2010) ("IK-WB16A/IK-WB16A-W Camera").
Toshiba, "REC-WB16A-1 Recording Software," available at https://web.archive.org/web/20101107015613/http://www.toshibasecurity.

(56) References Cited

OTHER PUBLICATIONS com/products/ikwb16a_recording_sw.jsp (archived Nov. 7, 2010) ("REC-WB16A-1 Recording Software").
Toshiba, "REC-WB16A-1 Data Sheet," 2010, available at https://web.archive.org/web/20110322033145/http://www.toshibasecurity.com/pdf/_datasheets/REC-WB16A-1_ds.pdf (archived Mar. 22, 2011) ("REC-WB16A-1 Data Sheet").
Retail It, "IK-WB16A-W Is Toshiba's First Wireless 2MP IP Video Surveillance Camera," Sep. 6, 2010, available at https://www.retailitinsights.com/doc/ik-wb16a-w-is-toshibas-first-wireless-2mp-ip-0001 ("Retail It").
Surveillance-Video.com, "Toshiba Ik-WB16A IP PTZ Security Camera Product Review from Surveillance-Video.com," Oct. 6, 2010, available at https://www.youtube.com/watch?v=k2WWVhftEEo ("IK-WB16A/IK-WB16A-W Video").
Canon, "EOS 7D DSLR product information page," retrieved on Mar. 17, 2021, available at https://www.usa.canon.com/internet/portal/us/home/products/details/cameras/eos-dslr-and-mirrorless-cameras/dslr/eos-7d.
The-Digital-Picture.com, "Canon TOS 7D Review," retrieved on Mar. 17, 2021, available at https://www.the-digital-picture.com/Reviews/Canon-EOS-7D-Digital-SLR-Camera-Review.aspx#WFT.
Canon EOS 7D Product Brochure, 2009 available at https://cinequipt.com/cms-files/eos-7d-brochure.pdf.
Barnett, Shawn et al., "Imaging Resource Canon 7D Review" published on Jan. 15, 2010, retrieved on Mar. 17, 2021, available at https://www.imaging-resource.com/PRODS/E7D/E7DA.HTM.
Laing, Gordon, "Canon EOS 7D—Canon EOS 7D lenses, focusing, sensor and drive," published on Aug. 10, 2011, retrieved on Mar. 17, 2021, available at https://www.cameralabs.com/canon_eos_7d/3/.
Phottix, "Canon announces 7D, as expected," published on Sep. 1, 2009, retrieved on Mar. 17, 2021, available at http://journal.phottix.com/camera-news/canon-announces-7d/.
Carnathan, Bryan, "Canon EOS 7D review," published Nov. 16, 2009, retrieved on Mar. 17, 2021, available at https://www.the-digital-picture.com/Reviews/Canon-EOS-7D-Digital-SLR-Camera-Review.aspx#WFT.
Backscatter, "Canon 5D Mark II Underwater Video Review," retrieved on Mar. 17, 2021, available at https://www.backscatter.com/reviews/post/Canon-5D-Mark-II-Camera-Underwater-Video-Review.
Wireless File Transmitter, 2012, https://web.archive.org/web/20100211114514/http://web.canon.jp/imaging/wft/wft-e2/index.html (archived Feb. 11, 2008).
Wireless File Transmitter, 2007 https://web.archive.org/web/20090303142515/http://web.canon.jp/imaging/wft/wft-e2/index.html (archived Mar. 3, 2009).
Canon, "Wireless File Transmitter WFT-E4 II an overview," retrieved on Mar. 17, 2021, available at https://www.usa.canon.com/internet/portal/us/home/products/details/cameras/wireless-file-transmitters-and-adapters/wirelessfile-transmitter-wft-e4-ii-a.
Canon, "Wireless File Transmitter WFT-E4 II Instruction Manual" 2009 available at http://gdlp01.c-wss.com/gds/7/0300004177/01/wft-e4ii-en.pdf.
B&H Photo Video, Canon WFT-E4 IIA Wireless File Transmitter (WFT) retrieved on Mar. 17, 2021, available at https://www.bhphotovideo.com/c/product/664918-REG/Canon_4263B001_WFT_E4_IIA_Wireless_File.html.
KEH Camera, "Canon WFT-E4 IIA Wireless File Transmitter (5D Mark II product page," retrieved on Mar. 17, 2021, available at https://www.keh.com/shop/canon-wft-e4-ii-a-wireless-file-transmitter-220282.html.
CVP, "Canon WFT-E4 II Transmitter product page," retrieved on Mar. 17, 2021, available at https://cvp.com/product/canon_wfte4ii.
Ffordes Photographic, "Canon WFT-E4 Wireless File Transmitter product page," retrieved on Mar. 17, 2021, available at https://www.ffordes.com/p/COM-IV47BQ31188/releases/wft-e4-wireless-file-transmitter.

Castleberry, Kim, "Get a Wireless Grip," published Apr. 11, 2010, available at https://www.dpmag.com/cameras/slrs/get-a-wireless-grip/.
Aquadog, "Canon WFT-E2 II A, WFT-E4 II A and WFT-E5A Wireless File Transmitters," retrieved on Mar. 17, 2021, available at http://www.photographyreview.com/reviews/canon-wft-e2-ii-a-wft-e4-ii-a-and-wft-e5a-wireless-file-transmitters.
Canon Philippines, "WFT-E4/E4A, Firmware Version 1.0.1 (Wireless File Transmitter for the EOS 5D Mark II) [Windows]" updated Aug. 12, 2011, retrieved on, available at https://ph.canon/en/support/0400043003/1.
Canon Hong Kong, "WFT-E4/E4A, Firmware Version 1.0.1 (Wireless File Transmitter for the EOS 5D Mark II) [Mac OS X]" updated Aug. 12, 2011, retrieved on, available at https://hk.canon/en/support/0400043103/1.
Canon, "Wireless File Transmitter WFT E4 II Support page retrieved on Mar. 17, 2021, available at," https://www.canon.co.nz/cameras/wireless-file-transmitter-wft-e4-ii/support.
Canon, "Wireless File Transmitter WFT-E4 II," 2009, available at http://gdlp01.c-wss.com/gds/7/0300004177/01/wft-e4ii-en.pdf.
Photography on the net, "Forum for Canon Accessories," retrieved on Mar. 17, 2021, available at https://photography-on-the.net/forum/showthread.php?t=948256.
Arva-Toth, Zoltan, "Canon WFT-E2 II & WFT E4 II," Oct. 20, 2009, available at https://www.photographyblog.com/news/canon_wft-e2_ii_wft-e4_ii.
Love, Julian, "The WFT-E4 wireless transmitter," published on Feb. 17, 2009, available at http://blog.julianlove.com/2009/02/wft-e4-wireless-transmitter.html.
Akerman, Richard, "Canon EOS 5D Mark II and WFT-E4 GPS Adapter," published on Sep. 18, 2008, available at https://scilib.typepad.com/techreviews/2008/09/canon-eos-5d-ma.html.
Lewis, Gordon, "Technology Overload," published on Jul. 1, 2011, available at https://shutterfinger.typepad.com/shutterfinger/2011/07/technology-overload.html.
"ShutterSnitch Canon Eos5Dmark2 WFT-E4 iPad Wireless Transport and Apple TV" Jun. 7, 2012, available at https://www.youtube.com/watch?v=fNw0SqhWQwM.
EPhotozine, "Canon brings enhanced wireless control to the EOS-1 Series and EOS 5D Mark II," published on Oct. 20, 2009, available at https://www.ephotozine.com/article/canon-wft-e2-ii---wft-e4-ii-wireless-file-transmitters-12360.
Currys PCWorld Business, "Canon WFT-E4 II B Wireless File Transmitter-Wireless network adapter product page," retrieved on Mar. 17, 2021, available at https://business.currys.co.uk/catalogue/item/Canon+WFT-E4+II+B+Wireless+File+Transmitter/P139049P?.
Canon Indonesia, "WFT-E4 II model page," retrieved on Mar. 17, 2021, available at https://id.canon/en/support/WFT-E4%20II/model.
Canon Thailand, WFT Utility 3.5 for Windows, last updated Dec. 17, 2009, retrieved on Mar. 17, 2021, available at https://th.canon/en/support/0200099502/1.
Jones, Gareth, How to WFT-E4 II—Windows 7—Jun. 16, 2012, published Jun. 15, 2012 available at https://www.garethiwanjones.com/bristol-photography-blog/index.php/how-to-wft-e4-ii-windows-7-160612.
"Live View Shooting" Section from "Canon EOS 5D Mark II" by Michael Guncheon (Sterling Publishing Company, Inc., 2009), 18 pages.
Axis, "Milestones," available at https://www.axis.com/files/market_backgrounders/Axis_Milestones.pdf ("Milestones").
Axis, "Datasheet Axis 207/207W/207MW Network Cameras," Apr. 2009, available at https://web.archive.org/web/20100105092250/http://www.axis.com/files/datasheet/ds_207_combo_32848_en_0904_lo.pdf (archived Jun. 11, 2009) ("207/207W/207MW Datasheet").
Axis, "Axis 207/207W/207MW Installation Guide," Sep. 2006, available at https://web.archive.org/web/20070127021304/http://www.axis.com/files/manuals/27192.pdf (archived Jan. 27, 2007) ("207/207W/207MW Installation Guide").

(56) References Cited

OTHER PUBLICATIONS

Axis, "Axis 207W—How to set up a working wireless connection," available at https://web.archive.org/web/20070114185434/http://www2.axis.com/files/manuals/207W_wireless_setup.pdf (archived Jan. 14, 2007) ("207W Setup").

Axis, "Axis 207W/207MW—User's Manual," Jan. 2007, available at https://web.archive.org/web/20090219220441/http://www.axis.com:80/files/manuals/um_207w_mw_33158_en_1208.pdf (archived Feb. 19, 2009) ("207W/207MW User Manual").

Axis, "Axis Introduces World's Smallest Wireless MPEG-4 Network Camera," Sep. 27, 2005, available at https://www.axis.com/files/press_releases/pr_207w_us_050921.pdf ("207W U.S. Press Release").

Axis, "Axis Introduces World's Smallest Wireless MPEG-4 Network Camera," Sep. 27, 2005, available at https://web.archive.org/web/20090206000316/https://www.axis.com/files/press_releases/pr_207w_intl_en_050921.pdf ("207W International Press Release").

Axis, "Axis 207 Network Camera User's Manual," Aug. 2006, available at https://web.archive.org/web/20061026115341/http://www2.axis.com/files/sales/25384r6.pdf (Archived Oct. 26, 2006) ("207 User Manual").

Axis, "15 Years of network cameras: Axis product history," Apr. 13, 2011, available at https://www.youtube.com/watch?v=oR3YotmN7tl ("Axis Product History").

Egeniq, "CameraControl for Axis Video Tutorial #1: Managing Your Camera," Jan. 3, 2011, available at https://www.youtube.com/watch?v=quLgvNEkF0k ("Managing Your Camera").

Egeniq, "CameraControl for Axis Video Tutorial #2: Controlling Your Camera," Jan. 3, 2011, available at https://www.youtube.com/watch?v=ZFyMVKLYQbk ("Controlling Your Camera").

Egeniq, "CameraControl for Axis Video Tutorial #3: Setting Up Notifications," Jan. 6, 2011, available at https://www.youtube.com/watch?v=rgA9V1Guo5E ("Setting Up Notifications").

Egeniq, "CameraControl for Axis Video Tutorial #4: Using Connection Profiles," Jan. 4, 2011, available at https://www.youtube.com/watch?v=vmYEN1IRxDQ ("Using Connection Profiles").

Gotomycamera, "How to Setup an Axis Camera for Motion Detection," Aug. 28, 2008, available at https://www.youtube.com/watch?v=WZ3UFENKOSA ("Setup for Motion Detection").

Gotomycamera, "How to Setup an Axis Camera for Access from the Internet," Aug. 26, 2008, available at https://www.youtube.com/watch?v=z4ZY5tCoFC8 ("Setup for Internet Access").

Panasonic i-PRO-Quick Reference Guide for BL-C230 (Installation Guide & Setup Guide) 2019-2021 Panasonic i-PRO Sensing Solutions Co., Ltd. available at https://security.panasonic.com/training_support/support/technical_information/qr_guide_c230/.

Panasonic i-PRO-BL-C230_Home Network Products—Key Feature—2019-2021 Panasonic i-PRO Sensing Solutions Co., Ltd., available at https://security.panasonic.com/products_technology/products/bl-c230/.

Panasonic BL-VT164W Camera Unboxing, available at https://www.youtube.com/watch?v=VPerYpaRSGg.

Panasonic BL-C230A Network Camera: Videoture, available at https://www.youtube.com/watch?v=zZSxGiNlMEo.

Panasonic Ip Camera Setup Part 2, available at https://www.youtube.com/watch?v=aiwqWB72bGY.

Panasonic IP Cameras, available at https://www.networkwebcams.com/panasonic-bl-c230-wireless-pan-tilt-security-camera.

Panasonic BL-C230A Wireless Internet Security Camera, available at https://www.bhphotovideo.com/c/product/681345-REG/Panasonic_BL_C230A_BL_C230A_Wireless_Internet_Security.html.

Panasonic BL-C230 IP Camera With H.264/MPEG-4/JPEG Monitoring With Wireless Capability, available at https://www.securityinformed.com/panasonic-bl-c230-ip-camera-technical-details.html.

Panasonic BLC230 H.264/MPEG4 Wireless Network Camera, Quick Overview, available at https://www.sovereigncctv.com/panasonic-bl-c230-h-264-mpeg4-wireless-network-camera.html.

Panasonic IP camera URL, Connecting to your Panasonic IP camera, available at http://www.ispyconnect.com/man.aspx?n=panasonic&page=3.

Panasonic BL-C230 wireless indoor, compact, pan/tilt IP security camera with built-in motion detection, H.264, available at https://www.networkwebcams.co.uk/product_info.php?products_id=1072.

Panasonic Status Information Description, Wireless Status of Camera (BL-C230) available at https://eww.cnw.panasonic.co.jp/security/g/netwkcam/technic/cam_status_wireless.html.

Panasonic BL-C230A and Control4—Driver?, c4forums | The Control4 Community, available at https://www.c4forums.com/topic/9393-panasonic-bl-c230a-and-control4-driver/.

Vera Smarter Home Control, Topic: Panasonic BL-C230A Setup, available at http://forum.micasaverde.com/index.php?topic=5658.0.

Panasonic BL-C230A Network Camera on Sensr.net, Jan. 25, 2011, available at https://blog.sensr.net/2011/01/24/panasonic-bl-c230a-on-sensr/.

BL-C230 (/56-panasonic/homebusiness-use-cameras/323-bl-c230.html) available at http://www.tsf.lv/56-panasonic/homebusiness-use-cameras/323-bl-c230.html.

Dehal website(non-English) available at http://www.idehal.org/uploads/catalog/security-web/BL-C230%20FEATURE%20GUIDE.pdf.

Manuals Online, Panasonic BLC230 Security Camera User Manual, available at http://camera.manualsonline.com/manuals/mfg/panasonic/blc230.html.

BL-C230 Software Download—Panasonic, Help Owl Web Site Search, available at https://www.helpowl.com/p/Panasonic/BL-C230/Research/142344?search=bl-c230%20software%20download.

Panasonic Installation Guide, Model No. BL-C230 (Wireless/Wired Type) downloadable form available at https://www.scribd.com/document/93278022/BL-C230A-CE-IG-en.

Panasonic Setup Guide Network Camera Model No. BL-C210 (Wired Type) and BL-C230 (Wireless/Wired Type), ManualShelf available at https://www.manualshelf.com/manual/panasonic/blc230/user-guide-english.html.

Home Security and the Panasonic BL-C230, vimeo, available at https://vimeo.com/40372451.

Panasonic BL-C131A Network Camera Wireless 801.11, available at https://www.amazon.com/Panasonic-BL-C131A-Network-Camera-Wireless/dp/B000NVR9SM.

Panasonic i-PRO, BL-C131 Home Network Products, Key Feature, available at https://security.panasonic.com/products_technology/products/bl-c131/.

Panasonic Wireless Pan/Tilt MPEG-4 Network Camera Features, available at https://shop.panasonic.com/support-only/BL-C131A.html.

Panasonic i-PRO, BL-C131 Home Network Products, Key Feature, available at https://security.panasonic.com/products_technology/products/bl-c131/spec/.

Panasonic Network Camera Manual, available at https://jcms.panasonic.com/pcc/cgi-bin/products/netwkcam/download_us/tbookmarka.cgi?g=C131.

Panasonic Setup Guide Network Camera, Model No. BL-C111A and BL-C131A, available at https://www.psn-web.net/ssbu-t/netwkcam_net/download/us/manual/blcam/BL-C111A_BL-C131A_SG.pdf.

Panasonic Important Information Network Camera, Model No. BL-C111A and BL-C131A, available at https://www.psn-web.net/ssbu-t/netwkcam_net/download/us/manual/blcam/BL-C111A_BL-C131A_II.pdf.

Panasonic Installation Guide Network Camera, Model No. BL-C111A and BL-C131A, available at https://www.psn-web.net/ssbu-t/netwkcam_net/download/us/manual/blcam/BL-C111A_BL-C131A_IG.pdf.

B&H Photo Video Pro Audio "Panasonic BL-C131A 802.11g Wireless Network Camera with Remote Pan & Tilt, Microphone and Simultaneous MPEG-4/JPEG Streaming" available at https://www.bhphotovideo.com/c/product/488295-REG/Panasonic_BL_C131A_BL_C131A_802_11g_Wireless_Network.html.

(56) References Cited

OTHER PUBLICATIONS

Network Webcams blog "How to set up your Panasonic IP Camera on your Wireless Network" available at https://www.networkwebcams.co.uk/blog/2008/07/03/howto-set-up-your-panasonic-ip-camera-on-your-wireless-network/.
Cam Viewer, "Panasonic BL-C131—Cam Viewer for Panasonic cameras" Nov. 12, 2013 available at https://web.archive.org/web/20210317194412/https://www.youtube.com/watch?v=b1QS7zm7ato as retrieved on Mar. 17, 2021.
Sehat, Langsing "Panasonic BL-C131A Network Camera Wireless 802.11 Review" May 27, 2012 available at https://web.archive.org/web/20210317195215/https://www.youtube.com/watch?v=3_rWhofepWM as retrieved on Mar. 17, 2021.
Panasonic "Panasonic Setup Guide Network Camera, Model No. BL-C111 (Wired Type), BL-C131 (Wireless/Wired Type)" available at https://www.psn-web.net/ssbu-t/netwkcam_net/download/other/manual/blcam/BL-C111CE_BL-C131CE_SG_en.pdf.
Dang, Hugie, "Panasonic BL-C131 Sample Recording", Jul. 12, 2009 available at https://web.archive.org/web/20210317195738/https://www.youtube.com/watch?v=Up4FkFrZzsg as retrieved on Mar. 17, 2021.
EvilSpeeder, "Night Motion", Jul. 2, 2009 available at https://web.archive.org/web/20210317200143/https://www.youtube.com/watch?v=IuM7nijIG1s as retrieved on Mar. 17, 2021.
VoiceSonic "Panasonic BL-C131A Camera" available at https://www.voicesonic.com/customer/Panasonic_system-25094-Panasonic_BLC131A_Camera_BLC131A.html.
Panasonic "Panasonic ideas for life, Home Network Cameras, Wired Type BL-C111, Wireless Type, BL-C131" available at http://pdfstream.manualsonline.com/3/3684a021-cb4f-442f-b618-9fa1b00654fc.pdf.
"Panasonic BL-C131A Network Camera Wireless 802.11" 2015: DailyMotion, available at https://www.dailymotion.com/video/x2g1kzd.
CocoonTech.com "Panasonic BL-C131A vs BL-C30A" available at http://cocoontech.com/forums/topic/10754-panasonic-bl-c131a-vs-bl-c30a/.
ISpyConnect "Connecting to your Panasonic IP camera*" available at http://www.ispyconnect.com/man.aspx?n=panasonic&page=2.
CleanCSS.com "Panasonic BL-C131A Default Router Login and Password" available at https://www.cleancss.com/router-default/Panasonic/BL-C131A.
ManualsBase.com "Panasonic BL-C131 user manual" available at http://www.manualsbase.com/manual/410030/security_camera/panasonic/bl-c131/.
The VideoLAN Forums "Audio/Video playback for BL-C131A Panasonic Network Camera" available at https://forum.videolan.org/viewtopic.php?t=46896.
ManualZZ the universal manuals library "User manual | MPEG-4 Video resolution 640×480, 320×240 (default), 192×144" available at https://manualzz.com/doc/25823493/mpeg-4-video-resolution-640-x-480--320-x-240--default---1 . . . .
ManualZZ the universal manuals library "Panasonic | BLC-131 | Datasheet | Panasonic BLC-131 Datasheet" available at https://manualzz.com/doc/2672275/panasonic-blc-131-surveillance-camera.
ManualZZ the universal manuals library "User manual | Video resolution 640×480, 320×240(default) BL-C1" available at https://manualzz.com/doc/44501223/video-resolution-640-x-480--320-x-240-default-.
ManualZZ the universal manuals library "User manual | Panasonic BL-C131 Security Camera User Manual" available at https://manualzz.com/doc/2081685/panasonic-bl-c131-security-camera-user-manual.
Murphy Mac—Screencasts and Tutorials "King of Wireless Webcams—Panasonic BL-C131A" available at http://murphymac.com/king-of-wireless-webcams-panasonic-bl-c131a/.
NetworkCameraReviews.com "Panasonic BL-C131 network software" available at http://www.networkcamerareviews.com/forums/about3185.html.
Vimeo, "Panasonic BL-C131" 2014, available on https://vimeo.com/87163065.
B&H Photo Video Pro Audio "Sony SNC-RZ50N 1/4-Inch CCD Network PTZ Security Camera with 3.5-91mm f/1.6 Lens, 26x Optical Zoom Lens, Day/Night, Image Flip and Motion Detector Features" available at https://www.bhphotovideo.com/c/product/423163-REG/Sony_SNCRZ50N_SNCRZ50N_1_4_Inch_CCD_Network.html.
"Sony SNC-P5—Cam Viewer for Sony cameras" Nov. 22, 2013 available at https://www.youtube.com/watch?v=c40yXUIIzOM.
Yanicelli, Jorge "Sony IPELA", Jul. 10, 2008 available at https://www.youtube.com/watch?v=IkglcDqKypl.
Aegis Electronic Group, Inc "Sony SNC-RZ50N (SNCRZ50N)—A PTZ Camera That Accessorizes!" available at https://www.aegis-elec.com/blogs/sony-snc-rz50n-sncrz50n-a-ptz-camera-that-is-filled-with-features/.
123SecurityProducts "Sony SNC-RZ50N.b Network PTZ Camera with 340 degree Pan, Day/Night, H.264 and JPEG/MPEG-4 Dual Streaming, Factory Certified Refurbished" available at https://www.123securityproducts.com/snsomucodane1.html.
CNET "Sony IPELA SNC-RZ50N—network surveillance camera Specs" available at https://www.cnet.com/products/sony-ipela-snc-rz50n-network-surveillance-camera/.
Newegg "Sony SNC-RZ50N 640×480 MAX Resolution RJ45 Surveillance Camera" available at https://www.newegg.com/sony-snc-rz50n-ptz-camera/p/N82E16826159069.
A1 Security Cameras "Sony SNC-RZ50N H.264 18× zoom Day/Night PTZ IP Security Camera" available at https://www.a1securitycameras.com/sony-snc-rz50n-mpeg4-ptz.html.
Ebay "Sony SNC-RZ50N Multi Codec PTZ Network Camera—Color, Black & White—CCD—Cable" available at https://www.ebay.com/itm/Sony-SNC-RZ50N-Network-Camera-SNC-RZ50N-/172145527547.
JenCam GmbH "SNC-RZ50/Outdoor" available at https://www.jencam.de/SNC-RZ50/OUTDOOR/en.
Surveillance-Video "Sony, SNC-RZ50N.b Sony Day/Night Network Camera—Refurbished" available at https://www.surveillance-video.com/snc-rz50n-r.html#additional_tabbed.
Surveillance-Video "Sony, Network Camera, Application Guide 1.5" available at https://www.surveillance-video.com/media/lanot/attachments/customimport/SNC-RZ50N-R-Manual.pdf, 32 pages.
Surveillance-Video "Sony, Network Camera, User's Guide, Software Version 2.2, IPELA SNC-RZ50N/RZ50P" available at https://www.surveillance-video.com/media/lanot/attachments/customimport/SNC-RZ50N-R-Quick-User-Guide.pdf, 120 pages.
Sony Make.Believe Comparison Chart for IP Rapid Dome and PTZ Cameras; IP Mini Dome Cameras; and IP Fixed Cameras, Spring 2010, Sony Electronics Inc. https://www.surveillance-video.com/media/lanot/attachments/customimport/SNC-RZ50N-R-Comparison.pdf.
Product for sale webpage for Sony, SNC-RZ50N.b Sony Day/Night Network Camera—Refurbished, https://www.surveillance-video.com/snc-rz50n-r.html.
Product for sale webpage for Sony SNCRZ0P Network PTZ Security Camera, https://www.sovereigncctv.com/sony-sncrz50p-network-ptz-security-camera-clearance-3608.html.
Sony SNC-RX Series Datasheet for Network Cameras SNC-RX Series SNC-RZ50N/RX50P, SNC—CS50N/CS50P, 2009, Sony, https://www.use-ip.co.uk/datasheets/datasheet_732.pdf.
Sony IP Camera URL, Connecting to your Sony IP camera, 2020, iSpy Connect.com, ihttp://www.ispyconnect.com/man.aspx?n=sony&page=4.
Sony SNC-RZ50N Network Cameras, Puget Sound Instrument Tacoma WA 2013, https://www.psicompany.com/sony-snc-rz50n-network-camera/.
https://www.networkwebcams.co.uk/downloads/sony/nwl_sony_sncrx570p_ds.pdf.
Sony Professional Products Support and Services, 2004-2021 Sony Electronics Inc., https://pro.sony/ue_US/product-resources/software-firmware/1237493460713.

(56) References Cited

OTHER PUBLICATIONS

Sony SNC-RX530P PTZ network camera—outdoor bundle, Network Webcams Specialist IP Camera Store, 2004-2021 NW Security Group, https://www.networkwebcams.co.uk/product_info.php?products_id=905.
Sony Product Information, SNC-RX530P, Intelligent Network Camera with 216× zoom—Black, https://www.networkwebcams.co.uk/downloads/sony/nwl_sony_sncrx530p_ds.pdf.
DBH18 Dome Camera Adapter for Sony SNC-RX530, SNC-RX-550, SNC-RX-570, w/fan-assisted heater 100-240VAC, Camera power supply 12VDC, 3A, Winncom Products, 1998-2020, https://www.winncom.com/en/products/ODBH18H114.
Sony IP cameras, Network Webcams, Specialist IP Camera Store, https://www.networkwebcams.com/sony-snc-rx550n-endless-pan-tilt-zoom-ip-camera-26x.
Sony Network Camera, IPELA, SNC-RX550P, http://www.networkwebcams.co.uk/downloads/sony/nwl_sony_sncrx550p_ds.pdf.
Look, Antony, "Sony PTZ Camera Guide", Published Nov. 21, 2010, IPVM, https://ipvm.com/reports/sony-ip-ptz-camera-guide.
Sony Make.Believe, SNC-RX Series, Network Cameras, IPELA, http://pdfstream.manualsonline.com/0/031c89cc-399e-4d8f-8704-31e9ae4b3d3e.pdf.
Network Webcams Website, available at https://www.networkwebcams.com/downloads/sony/nwlus_sony_snc-rx550n_ds.pdf.
Amazon, "Sony SNC-RX550N/B Multi Codec PTZ Network Camera—Black (SNCRX550N/B)" available on https://www.amazon.com/Sony-SNC-RX550N-Multi-Network-Camera/dp/B006G26BCW.
Sony SNC-RX550N/B Multi-Codec PTZ Day/Night Network Dome Camera with 26× Optical Zoom Lens, JPEG/MPEG4/H.264 Compression Selectable, Black Housing https://www.bhphotovideo.com/c/product/423161-REG/Sony_SNCRX550N_B_SNC_RX550N_B_Multi_Codec_PTZ_Day_Night.html.
Sony, SNC-RX550-B, PTZ Network IP Camera with 470 TVL—Refurbished https://www.surveillance-video.com/snc-rx550-r.html.
Sony IELA SNC-RX550N—network camera Series Specs, CNET, 2021 https://www.cnet.com/products/sony-ipela-snc-rx550n-network-camera-series/.
SonySNC-RX550CGI command manual, Version 1.0, Nov. 10, 2005, Sony Corporation, http://www.aegis-elec.com/pdf/product/Sony-SNC-RX550-CGI-Manual.pdf.
"Results for 'sncrx550'", TWACOMM, available at http://www.twacomm.com/catalog/model_SNCRX550.htm?pid=1000&utm_source=fgl&utm_medium=prodlist&utm_term=SNC-RX550.
Ebay, Sony SNC-RX550N PTZ Network IP Security Surveillance Camera. https://www.ebay.com/itm/Sony-IPELA-Network-Camera-SNC-RX550N-w-Power-Supply-/383032590776.
"Sony SNC-RZ25N Camera Demo from Surveillance-Video.com", Dec. 14, 2010, available at https://www.youtube.com/watch?v=Ps_BWB0NzA.
Model: SNC-RX550N—Discontinued, Puget Sound Instrument, Tacoma, WA, 2013-20121, https://www.psicompany.com/sony-snc-rx550n-network-camera/.
Sony Make.Believe, SNC-RX Series, Network Cameras, IPELA, Intelligent and Feature Rich—Sony High-Performance Multi-Codec Network Cameras Deliver Efficient 24/7 Monitoring, http://pdfstream.manualsonline.com/0/031c89cc-399e-4d8f-8704-31e9ae4b3d3e.pdf.
Sony SNC-RX550 RTSP URL, Security World, https://security.world/rtsp/view/sony/SNC-RX550/.
Sony SNC-RX550P PTZ network camera—outdoor bundle https://www.networkwebcams.co.uk/product_info.php?products_id=906.
Sony, Network Cameras, SNC-RX550N SNC-RX550P, Connect Your Vision IPELA, https://www.zerone.com.tw/support/Sony/SNC-RX550%E5%9E%8B%E9%8C%84.pdf.
Sony Make.Believe, SNC-RX570P, Intelligent Network Camera with DynaView and 432× zoom—Black http://www.elviacctv.cz/content/files/prospekty/original/SNC-RX570P.pdf.
Mounts and Housings, https://buy.eescodist.com/static/catalog/products/images/Catalog/CSC2014/CSC_2014_Page_409.pdf.

"Connecting to your ipela IP camera*" 2020, downloaded from https://www.ispyconnect.com/man.aspx?n=ipela.
SNC-RX530P, "Informacion del product" available at http://www.cctvcentersl.es/upload/Catalogos/SNC-RX530P_eng.pdf, 3 pages.
Expandore, "Sony SNC-RX550P/WCE" available at https://www.expandore.com/product/Sony/CCTV/SNC-RX550PWCE.htm.
Docplayer, "SNC-RX550N High Resolution Day/Night Pan/Tilt Zoom Camera with 10/100 Base T Ethernet", 2021 available at https://docplayer.net/30231691-Snc-rx550n-high-resolution-day-night-pan-tilt-zoom-camera-with-10-100-base-t-ethernet.html.
A1 Security Cameras, "Sony SNC-CS50N H.264 Day/Night IP Security Camera" 2021, available at https://www.a1securitycameras.com/sony-snc-cs50n.html.
Network Webcams, "Sony IP Cameras" 2021, available at https://www.networkwebcams.com/sony-snc-cs50n-compact-static-intelligent-network-camera.
Sony, "Professional Product Support" available at https://pro.sony/en_NI/product-resources/software-firmware/1237493455913.
Surveillance-Video.com "Sony IPELA SNC-CS50N & SNC-CS11 Camera Demos From Surveillance-video.com", Apr. 5, 2012 available at https://www.youtube.com/watch?v=IKTmcSialHA.
Wholesale Distributor of Security, AV & Low Voltage Products "Best Selling Categories" downloaded from https://www.en.adiglobaldistribution.ca/Product/SH-SNCCS50N.
Amazon, "Viewer for Sony IP cameras" 2014, downloaded from https://www.amazon.com/Viewer-for-Sony-IP-cameras/dp/B00HQUFZ2K.
Manualslib, "Sony IPELA SNC-CS50N Brochure & Specs" available at https://www.manualslib.com/manual/747190/Sony-Ipela-Snc-Cs50n.html, 8 pages.
Sony, "The Sony SNC-CS50P Network Camera—An Easy to Operate, High-Performance Colour IP Network Camera that Takes Remote Monitoring to the Next Level" 2006, downloaded from https://www.networkwebcams.co.uk/downloads/sony/nwl_sony_snccs50p_ds.pdf, 6 pages.
Manuals Dump, "Sony SNC-CS50, SNC-RZ50 manual" 2010, available at https://manualsdump.com/en/manuals/sony-snc-cs50-snc-rz50/31319/1, 8 pages.
Security World, "Sony SNC-CS50 RTSP URL" 2010, available at https://security.world/rtsp/view/sony/SNC-CS50/.
Expandore, "Sony SNC-CS50P" available at https://www.expandore.com/product/Sony/CCTV/SNC-CS50P.htm.
http://content.usatoday.com/communities/technologylive/post/2010/09/for-the-person-who-has-everything--a-telephoneheadset-with-built-in-video-camera/1#.T4y11NkdzAk.
Looxcie, "Buy Looxcie" 2021, available at https://web.archive.org/web/20100918093345/http://looxcie.com/buy-looxcie.html.
Looxcie, "Download the Looxcie App" 2021, available at https://web.archive.org/web/20100918094433/http://looxcie.com/looxcie-app.html.
Looxcie, "How Looxcie Works" 2021, available at https://web.archive.org/web/20100918093350/http://looxcie.com/share.html.
Zach, Best Live Streaming Cameras [year] [Complete Guide], Nov. 1, 2019 downloaded from http://www.looxcie.com/how-looxcie-works.html.
Looxcie, "User Manual Model LX1", 2010, downloaded from https://web.archive.org/web/20100923010550/http://looxcie.com/docs/Looxcie_User_Manual.pdf, 31 pages.
Looxcie, "Get Started Guide", 2010, downloaded from https://web.archive.org/web/20100920194308/http://www.looxcie.com/docs/Looxcie_Get_Started_Guide.pdf, 10 pages.
Gadget Shooter, "Looxcie hands-on, Wearable camcorder and bluetooth headset" Nov. 10, 2010 available at https://www.youtube.com/watch?v=CVMAjJ11Kww.
Fairlie, Rik "Would You Wear a Camcorder on Your Ear?" Oct. 1, 2010: Gadgetwise the New York Times Blog, available at https://gadgetwise.blogs.nytimes.com/2010/10/01/would-you-wear-a-camcorder-on-your-ear/.
Burns, Chris "Looxcie Bluetooth Video Camera Review" Apr. 11, 2011: Slas Gear, available at https://www.slashgear.com/looxcie-bluetooth-video-camera-review-with-an-htc-thunderbolt-11145337/.

(56) References Cited

OTHER PUBLICATIONS

Wireless File Transmitter WFT-E4 II Instruction Manual, downloaded from http://www.manualsdir.com/manuals/379634/canon-wireless-file-transmitter-wft-e4-ii-a.html on Mar. 17, 2021, copyright symbol 2009, 128 pages.
Panasonic, "Network Camera Comparison Chart," downloaded from https://www.manualslib.com/manual/561805/Panasonic-BI-C230.html?page=6#manual on Mar. 17, 2021, dated Oct. 2010, 6 pages.
Panasonic, BL-C111A BL-C131A Operating Instructions, downloaded from https://www.manualslib.com/manual/377830/Panasonic-BI-C111a-Network-Camera-Pan.html on Mar. 17, 2021, undated, 154 pages.
Panasonic, BL-C111A BL-C131A Service Instructions, downloaded from https://www.manualslib.com/download/454276/Panasonic-BI-C111a-Network-Camera-Pan.html on Mar. 17, 2021, copyright symbol 2007, 83 pages.
Panasonic, BL-C111A BL-C131A Specification Sheet, downloaded from https://www.manualslib.com/manual/119408/Panasonic-BI-C131.html on Mar. 17, 2021, undated, 2 pages.
Sony SNC-RZ50N Install Manual, downloaded from https://www.manualslib.com/manual/321527/Sony-Ipela-Snc-Rz50n.html?page=41#manual on Mar. 17, 2021, copyright symbol 2005, 139 pages.
Sony SNC-RZ50N User's Guide, downloaded from https://www.manualslib.com/manual/160065/Sony-Ipela-Snc-Rz50n.html?page=4#manual, copyright symbol 2005, 94 pages.
Sony SNC-RZ50N Features & Specifications, downloaded from https://www.manualslib.com/manual/703947/Sony-Ipela-Snc-Rz50n.html on Mar. 17, 2021, copyright symbol 2005, 8 pages.
Sony SNC-RX530 Installation and Operation Instructions Manual, downloaded from https://www.manualslib.com/products/Sony-Snc-Rx530-3735319.html on Mar. 17, 2021, dated Oct. 14, 2009, 19 pages.
Security Informed, "Sony Introduces Two New Intelligent 360 Degree Speed Dome Cameras—The SNC-RX530 and SNC-RX570," downloaded from https://www.sourcesecurity.com/sony-snc-rx530p-technical-details.html on Mar. 17, 2021, undated, 5 pages.
Sony, SNC-RX550N Manual downloaded from https://www.manualslib.com/manual/1263397/Sony-Snc-Rx550n.html on Mar. 17, 2021, copyright symbol 2005, 8 pages.
Sony, SNC-RX550N Manual downloaded from https://www.manualslib.com/manual/160057/Sony-Ipela-Snc-Rx550n.html on Mar. 17, 2021, copyright symbol 2005, 94 pages.
Wireless File Transmitter WFT-E4 WFT-E4A Instruction Manual, downloaded from https://www.manualslib.com/manual/824048/Canon-Wft-E4.html on Mar. 17, 2021, copyright symbol 2008, 108 pages.
First Office Action dated Mar. 17, 2015, issued in Chinese Patent Application No. 201180054541.7, 17 pages.
Second Office Action dated Nov. 30, 2015, issued in Chinese Patent Application No. 201180054541.7, 5 pages.
Third Office Action dated Jan. 20, 2016, issued in Chinese Patent Application No. 201180054541.7, 7 pages.
Fourth Office Action dated Feb. 6, 2017, issued in Chinese Patent Application No. 201180054541.7, 3 pages.
Re-examination Decision dated Jul. 2, 2018 in Chinese Patent Application No. 201180054541.7, 15 pages. English Translation Not yet Received.
Office Action in Chinese Patent Application No. 201180054541.7, dated Aug. 14, 2018, 8 pages.
Office Action in Chinese Patent Application No. 201910297135.1, dated Jun. 18, 2019,1 page.
Office Action in Chinese Patent Application No. 201910297135.1, dated Dec. 10, 2020, 2 pages.
Office Action in Chinese Patent Application No. 201910297135.1, dated May 8, 2021, 2021, 11 pages.
Ex-Parte Kennedy, Appeal No. 2008-1131 (U.S. Appl. No. 10/080,999, BPAI Sep. 18, 2008), 9 pages.
International Search Report and Written Opinion re: PCT Application No. PCT/US2011/051418, mailing dated Apr. 10, 2012.
International Preliminary Report on Patentability in PCT Application No. PCT/US2011/051418, mailing dated Mar. 28, 2013 (which corresponds to U.S. Appl. No. 13/822,255).
Supplementary Partial European Search Report dated Apr. 30, 2015, issued in European Patent Application No. 11825800.3, 8 pages.
Extended European Search Report dated Aug. 21, 2015, issued in European Patent Application No. 11825800.3, 11 pages.
Office Action in European Application No. 11825800.3 dated Jun. 21, 2017.
Office Action in European Application No. 11825800.3 dated Apr. 6, 2018.
Office Action in European Application No. 11825800.3 dated Jun. 18, 2019.
Office Action in European Application No. 11825800.3 dated Feb. 24, 2021.
Extended European Search Report in European Application No. 21206052.9 dated May 3, 2022 in 12 pages.
EPO Reminder Concerning Payment of the Designation Fee in European Application No. 21206052.9 dated Jun. 7, 2022 in 2 pages.
Contour IP Holding, LLC's Motion to File Under Seal (including Proposed Order, Redacted Version of Opening Claim Construction Brief, Exhibit 7, Exhibit 8, Exhibit 13, Exhibit 14, Exhibit 18, Appendix A, Appendix B) by Contour IP Holding, LLC., filed May 4, 2018, *Contour IP Holding, LLC v. GoPro, Inc.*, Case No. 3:17-cv-04738-WHO (involving U.S. Pat No. 8,890,954 and U.S. Pat. No. 8,896,694), 94 pages.
GoPro's Responsive Claim Construction Brief (including Appendix A, Appendix B, Exhibit A, Exhibit B, Exhibit C, Exhibit I, Exhibit J, Exhibit K, Exhibit M, Exhibit N, Exhibit Q, Exhibit R), filed May 18, 2018, *Contour IP Holding, LLC v. GoPro, Inc.*, Case No. 3:17-cv-04738-WHO (involving U.S. Pat No. 8,890,954 and U.S. Pat. No. 8,896,694), 81 pages.
Contour IP Holding, LLC's Reply Claim Construction Brief (including Exhibit 22, Exhibit 23, Exhibit 24, Exhibit 25, Exhibit 26, Exhibit 27, Exhibit 28) by Contour IP Holding, LLC., filed May 25, 2018, *Contour IP Holding, LLC v. GoPro, Inc.*, Case No. 3:17-cv-04738-WHO (involving U.S. Pat No. 8,890,954 and U.S. Pat. No. 8,896,694), 75 pages.
Tentative Claim Construction issued by Judge William H. Orrick, Jun. 14, 2018, *Contour IP Holding, LLC v. GoPro, Inc.*, Case No. 3:17-cv-04738-WHO (involving U.S. Pat No. 8,890,954 and U.S. Pat. No. 8,896,694), 7 pages.
Decision on Remand, dated Jul. 31, 2019, *GoPro, Inc., v. Contour IP Holding LLC*, Case No. IPR2015-01078 (involving U.S. Pat. No. 8,896,694), 49 pages.
Decision on Remand, dated Jul. 31, 2019, *GoPro, Inc., v. Contour IP Holding LLC*, Case No. IPR2015-01080 (involving U.S. Pat. No. 8,890,954), 47 pages.
European Examination Report for EP Application No. 11 825 800.3, dated Feb. 24, 2021, 5 pages.
Non-Confidential Brief for Plaintiff-Appellant, *Contour IP Holding LLC, v. GoPro, Inc.*, Case No. 22-1654, Aug. 16, 2022, 223 pages.
Nonconfidential Brief for Defendant-Appellee, *Contour IP Holding LLC v. GoPro, Inc.*, Case No. 22-1654, Nov. 10, 2022, 65 pages.
Non-Confidential Reply Brief for Plaintiff-Appellant, *Contour IP Holding LLC, v. GoPro, Inc.*, Case No. 22-1654, Dec. 12, 2022, 44 pages.
Judgment, *Contour IP Holding, LLC v. GoPro, Inc.*, Case Nos. 3:17-cv-04738-WHO, 3:21-cv-02143-WHO, Mar. 15, 2022, 1 page.
Citation of Supplemental Authority, *Contour IP Holding LLC v. GoPro, Inc.*, Case No. 22-1654, Feb. 23, 2023, 23 pages.
Response of Appellant, *Contour IP Holding LLC v. GoPro, Inc.*, Case No. 22-1654, Mar. 2, 2023, 2 pages.
Ambarella A5s—Hybrid DV Camera SoC Data Sheet Product Brief, Santa Clara, in 2 pages.
TV-IP512WN Wireless Internet Camera Server with 2-way Audio, User's Manual, Trendnet, retrieved from https://www.manualslib.com, in 82 pages (no date provided).
Federal Circuit Opinion, *Contour IP Holding LLC v. GoPro, Inc.*, Case No. 22-1654, Sep. 9, 2024, 13 pages.

(56) References Cited

OTHER PUBLICATIONS

Office Action in Chinese Patent Application No. 201910297135.1, dated Jan. 29, 2022, 8 pages.
Office Action in Chinese Patent Application No. 201910297135.1, dated Jul. 11, 2022, 7 pages.
Re-Examination Notice in Chinese Patent Application No. 201910297135.1, dated Jun. 5, 2023, 52 pages.
Office Action in Chinese Patent Application No. 202311201458.9 dated Apr. 29, 2024, 6 pages.

* cited by examiner

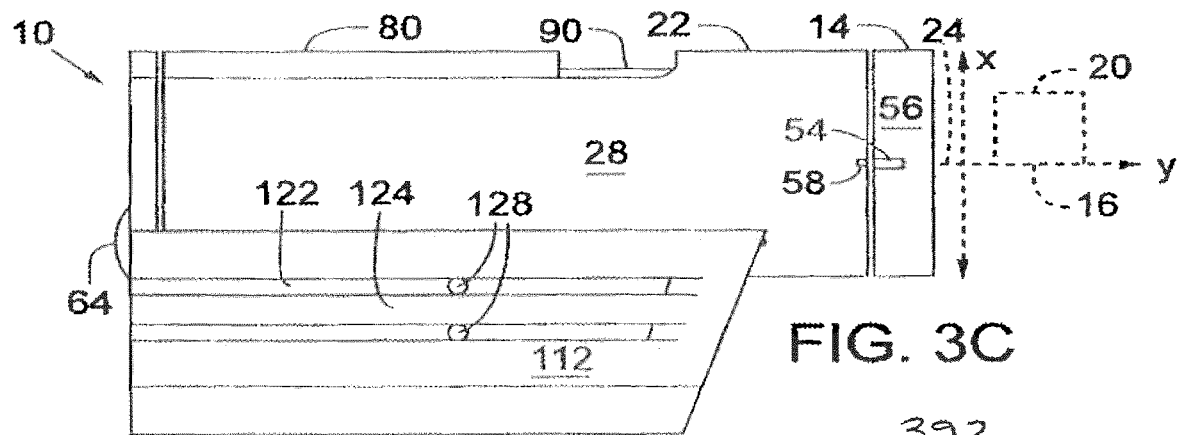
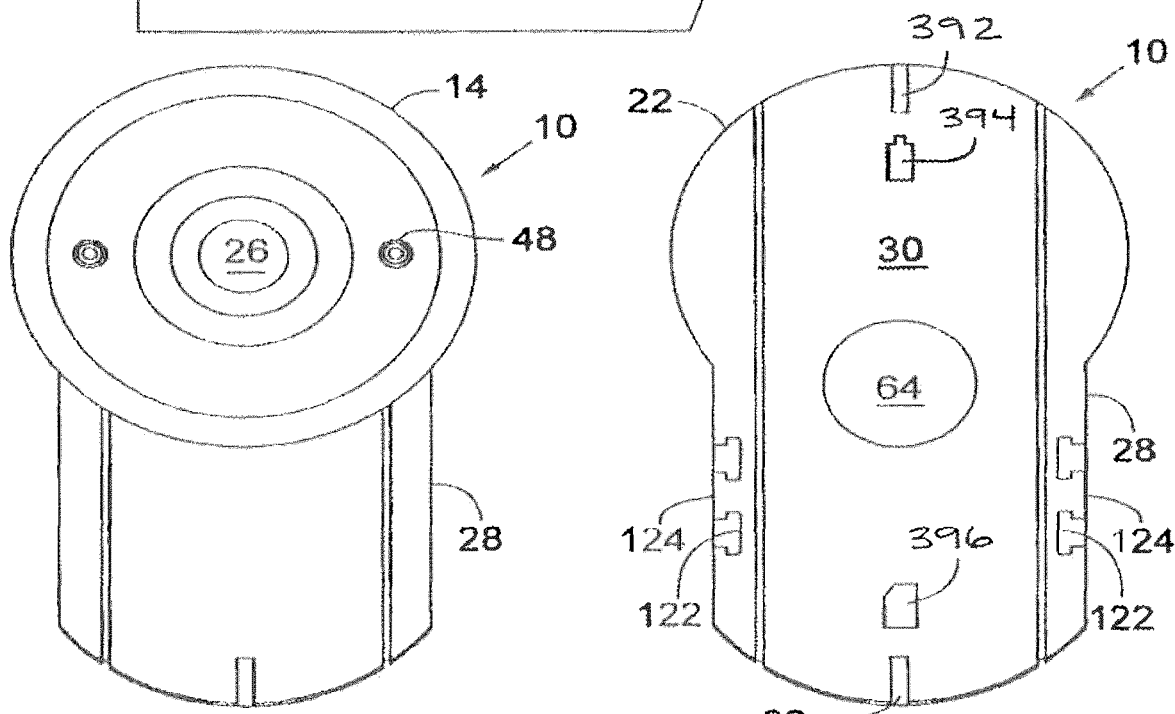
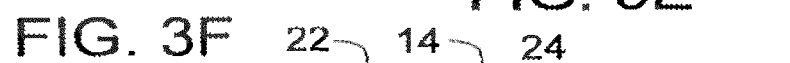
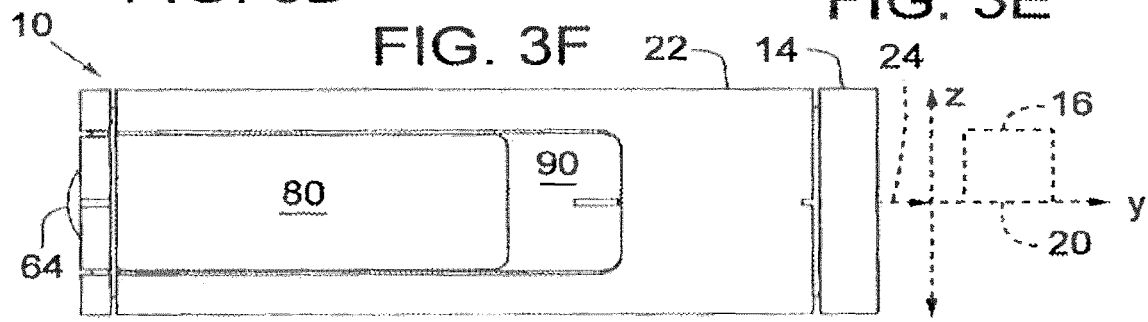

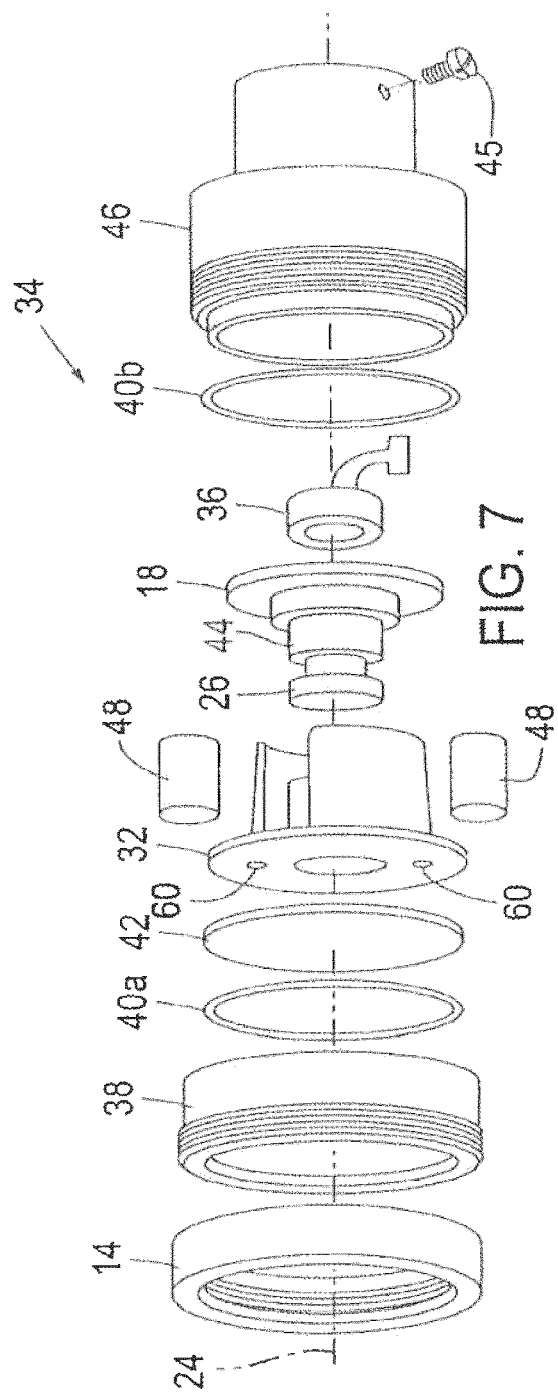
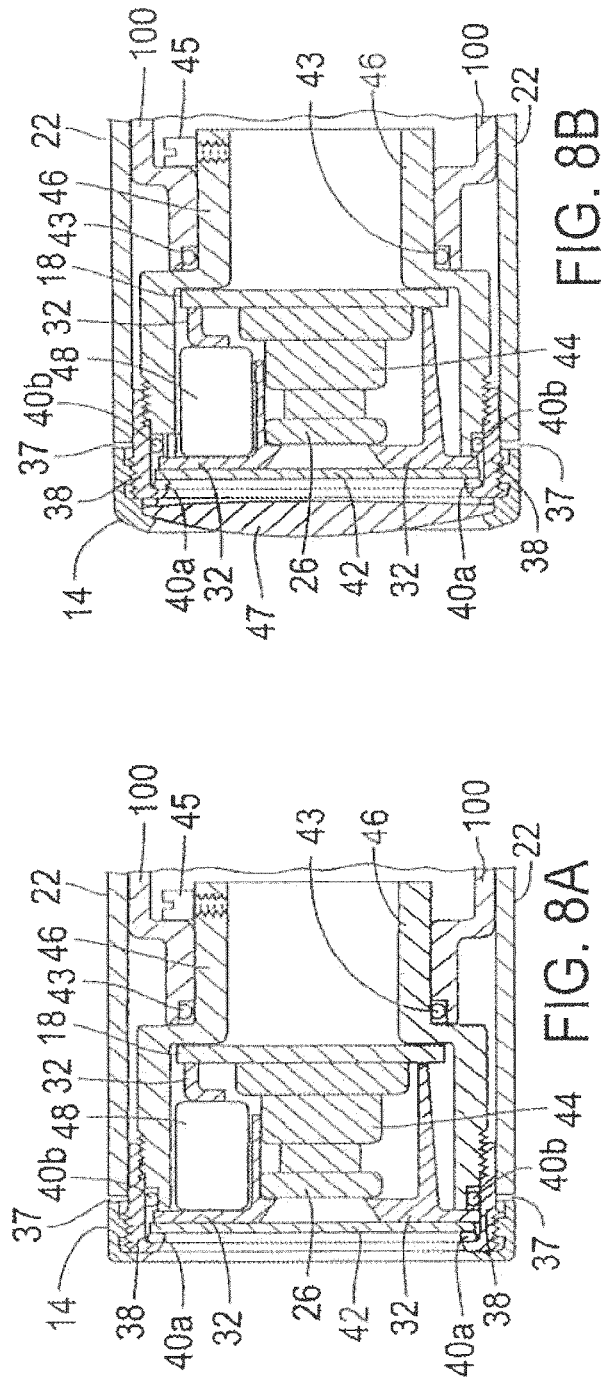

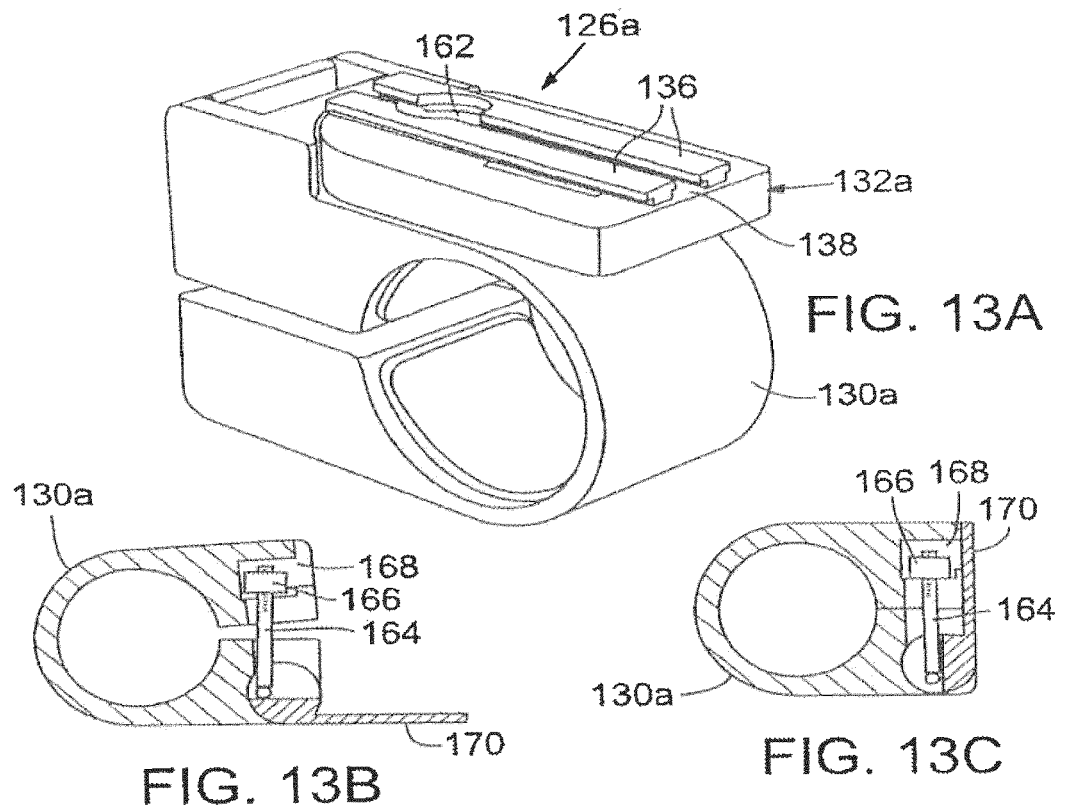
FIG. 13A
FIG. 13B
FIG. 13C
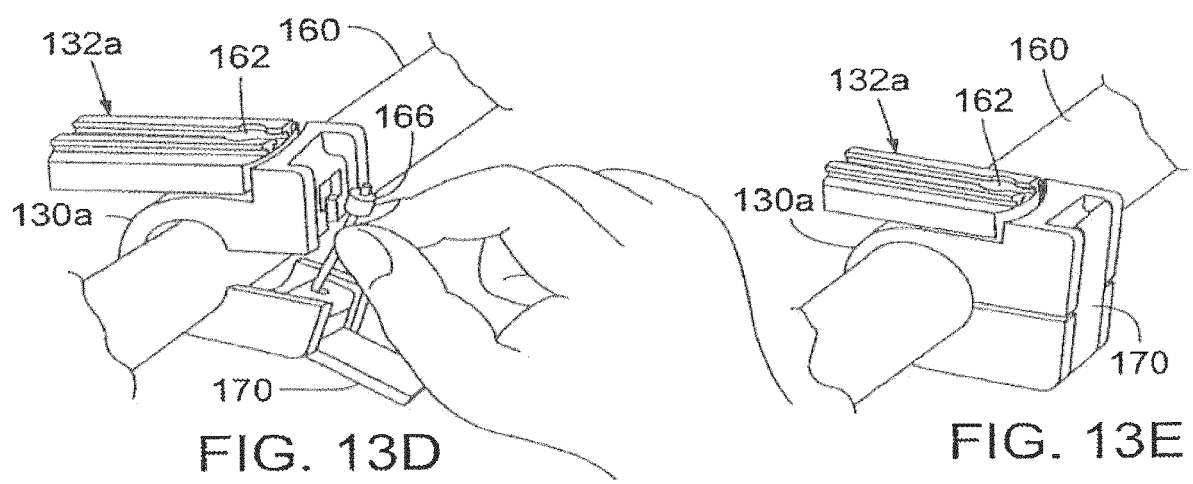
FIG. 13D
FIG. 13E

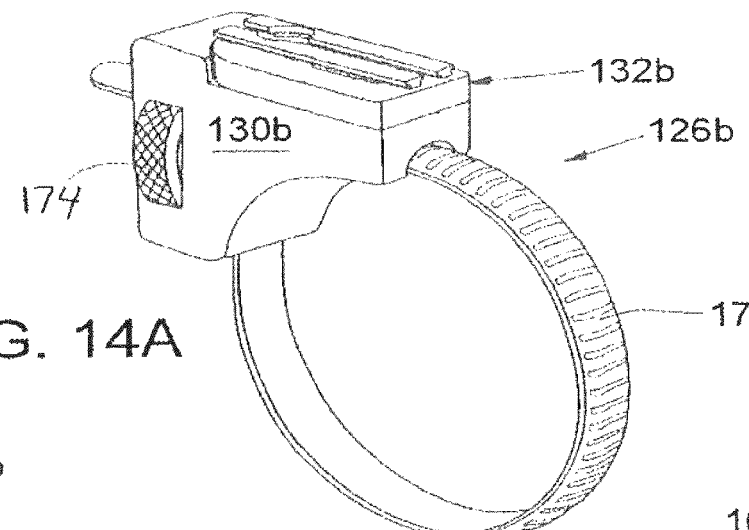
FIG. 14A
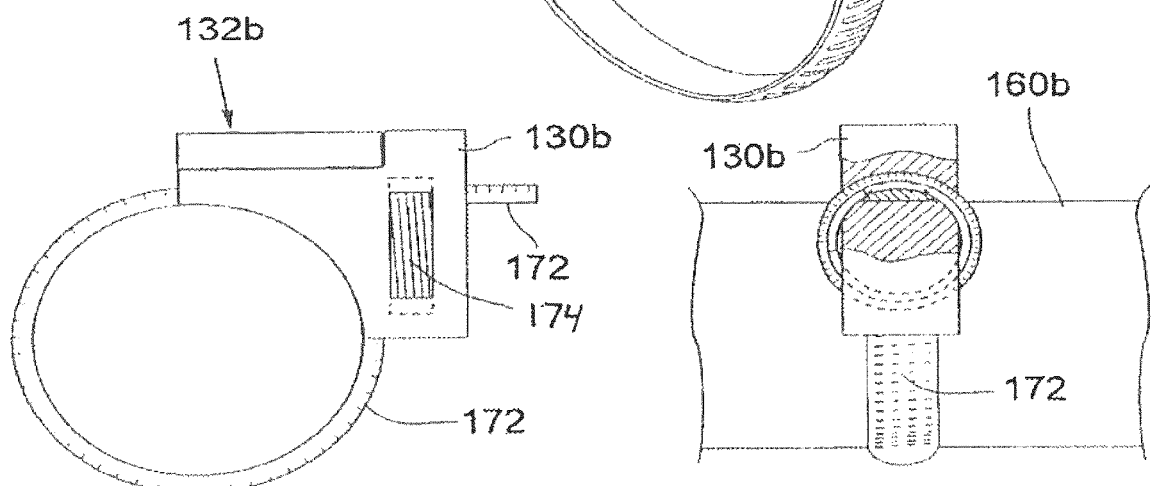
FIG. 14B
FIG. 14C
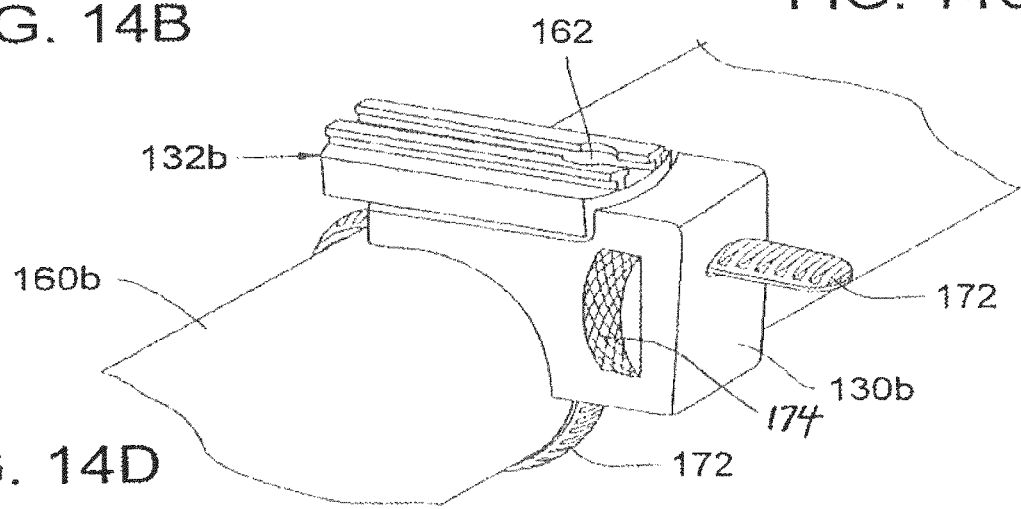
FIG. 14D

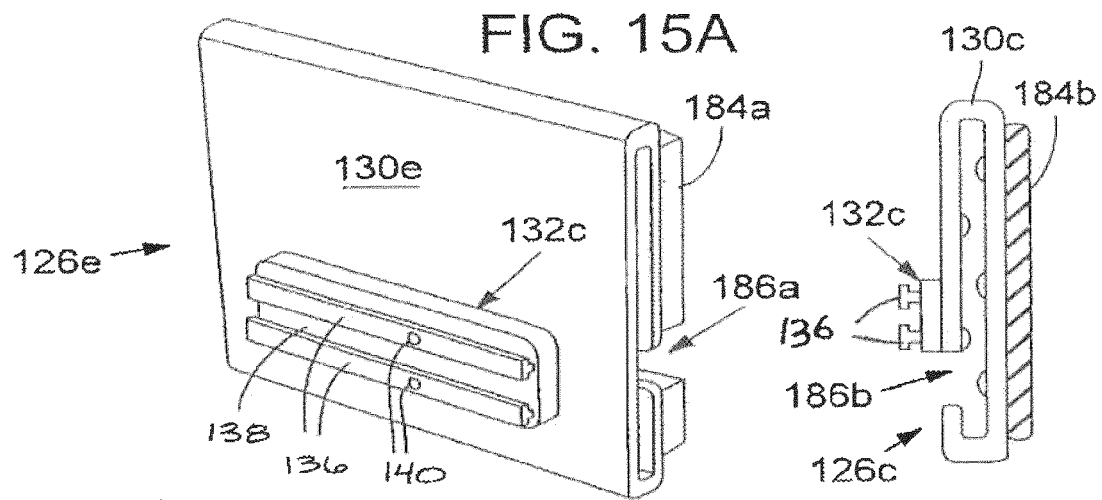
FIG. 15A
FIG. 15B
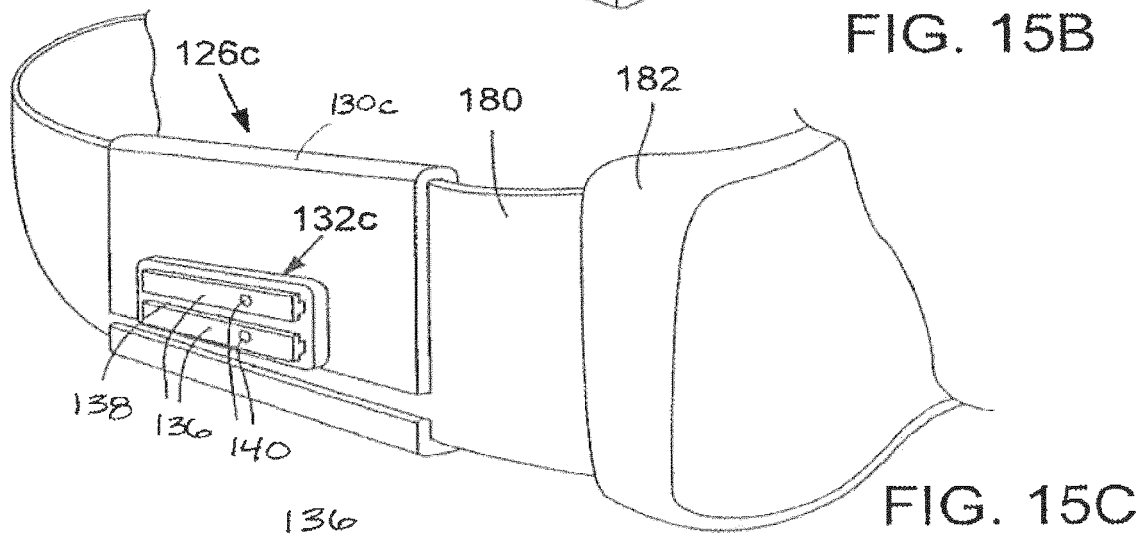
FIG. 15C
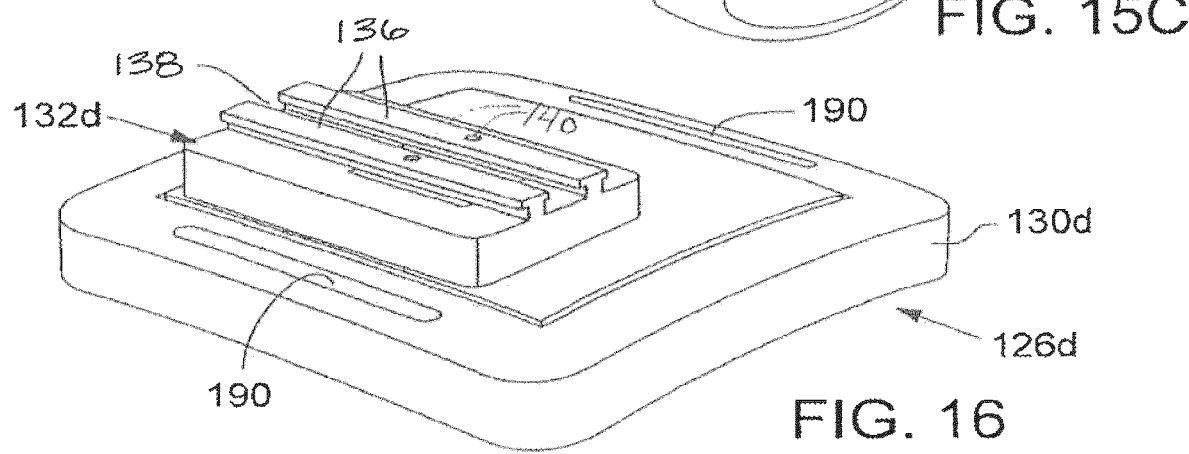
FIG. 16

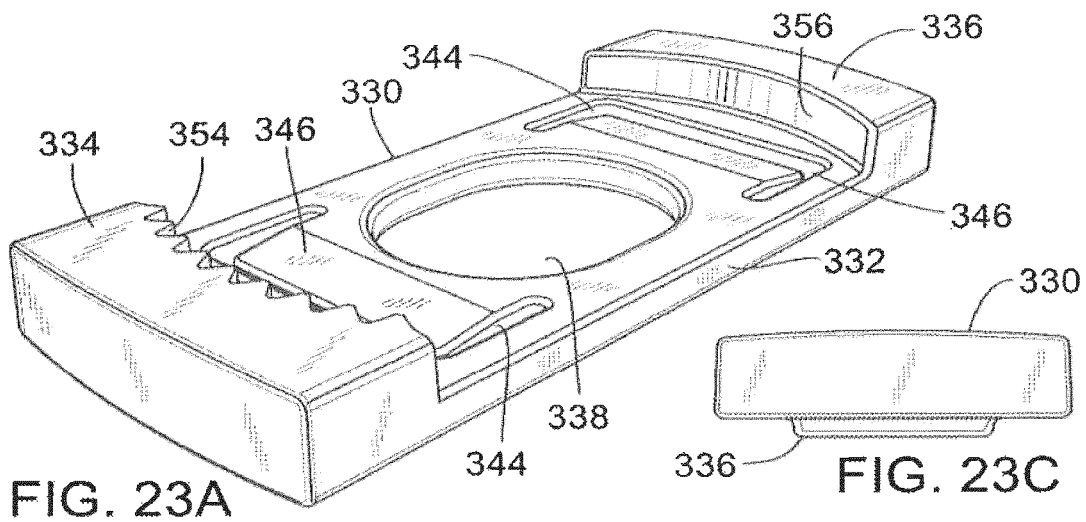
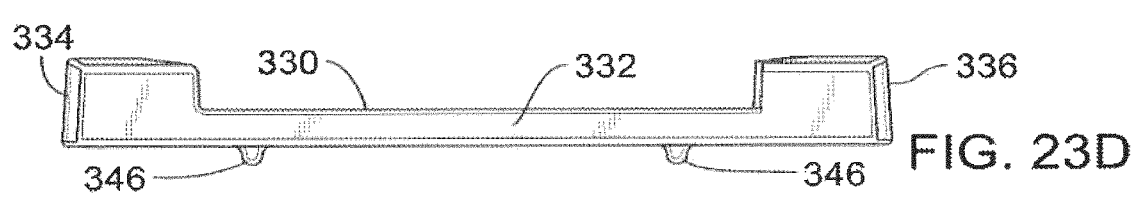
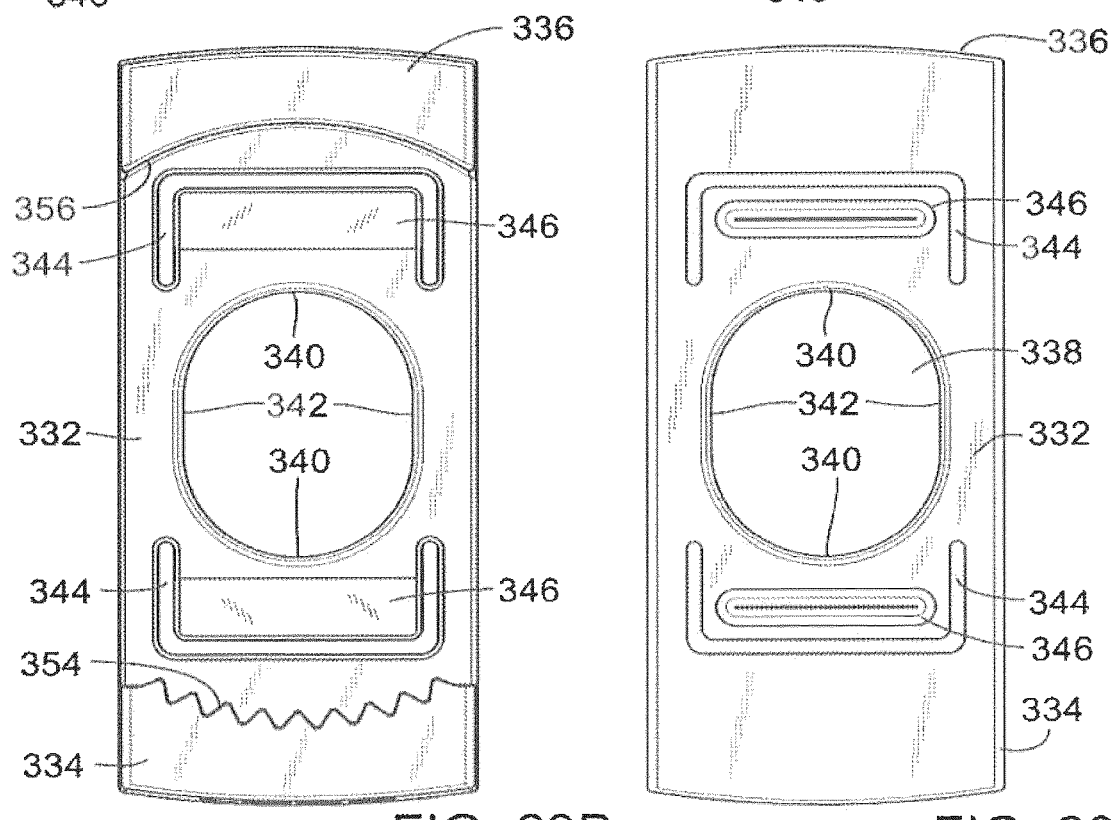

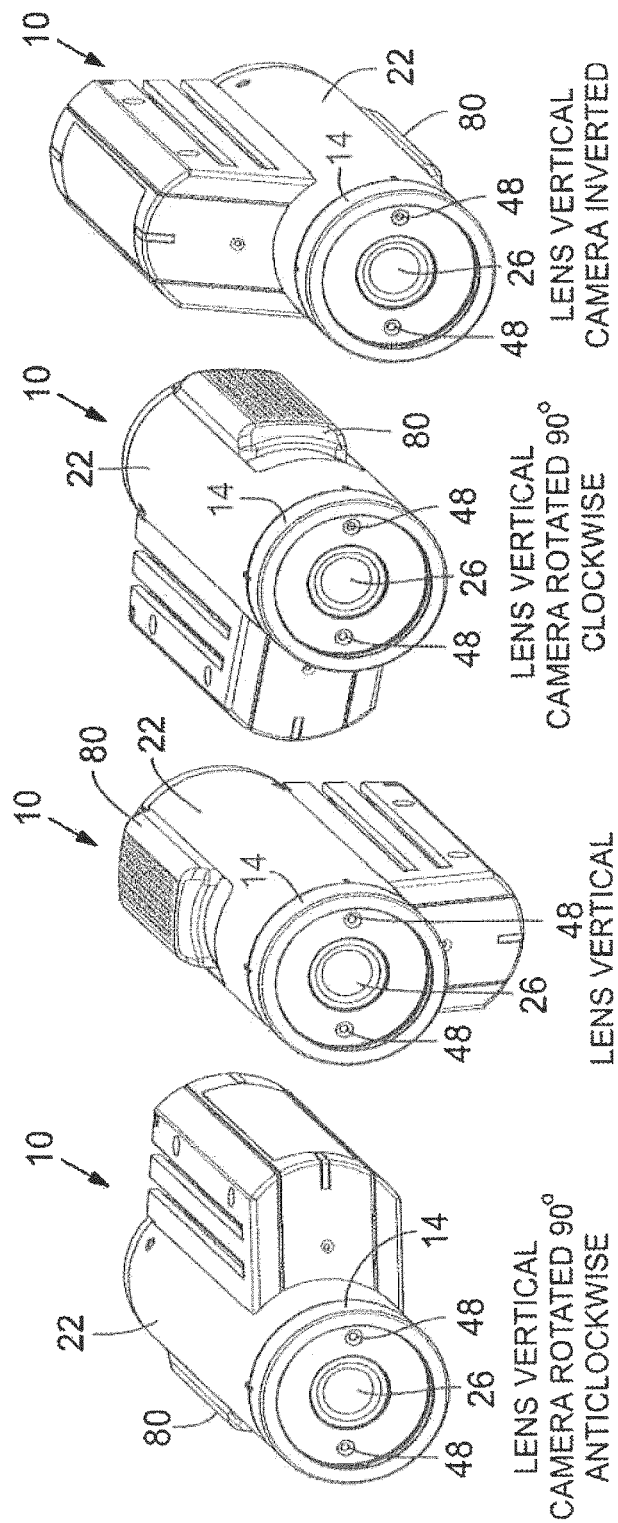
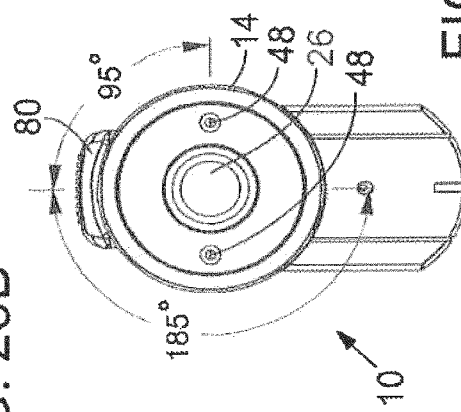

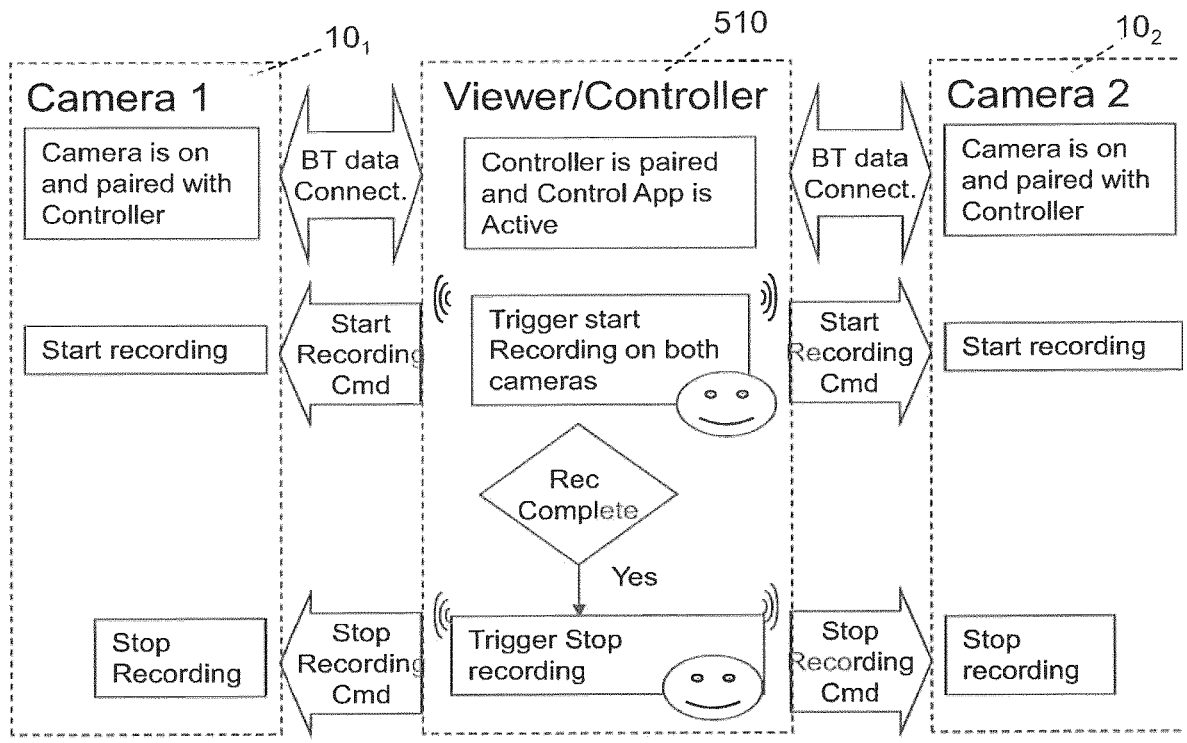
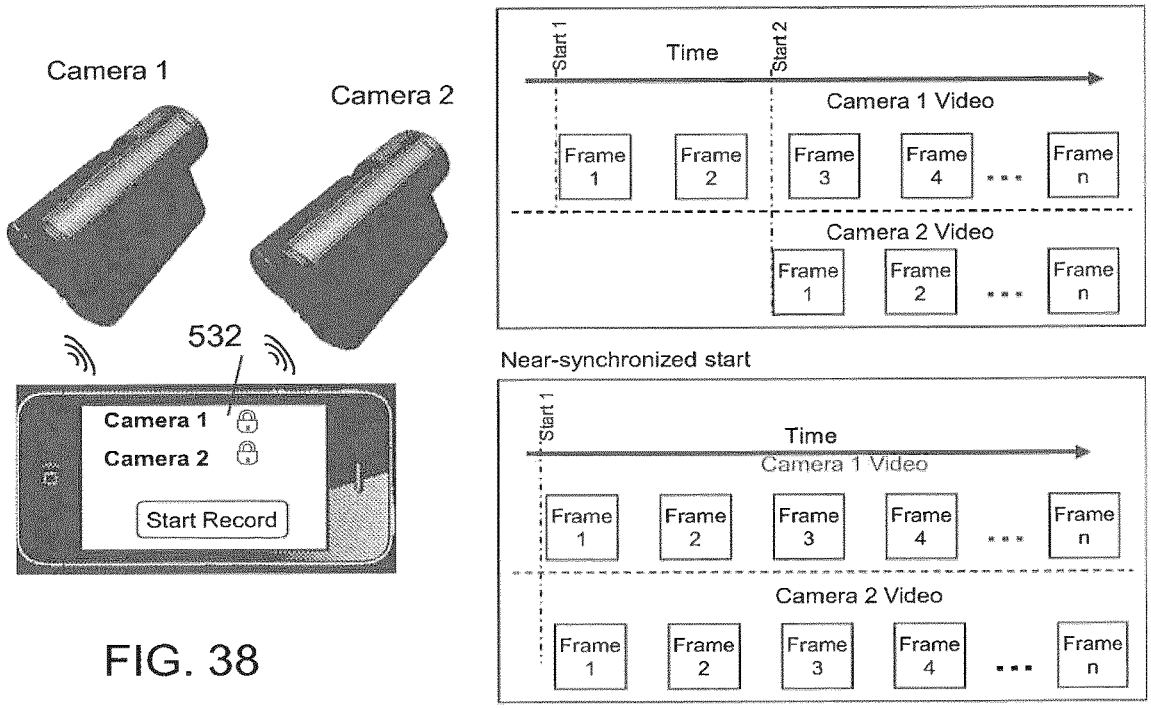
FIG. 38

PORTABLE DIGITAL VIDEO CAMERA CONFIGURED FOR REMOTE IMAGE ACQUISITION CONTROL AND VIEWING

TECHNICAL FIELD

This disclosure relates to point-of-view (POV) video cameras or camcorders and, in particular, to an integrated hands-free, POV action sports video camera or camcorder that is configured for remote image acquisition control and viewing.

BACKGROUND INFORMATION

First-person video cameras are a relatively new product category that have been adapted to capture POV video by action sports enthusiasts in a hands-free manner. Conventional first-person video cameras primarily comprise a lens that must be tethered to a separate digital video recorder or camcorder. FIGS. 1A and 1B present pictorial views of prior art first-person video cameras requiring a tethered lens approach to capturing first-person video recording. FIG. 1A presents a Twenty20™ device, and FIG. 1B presents a Viosport™ device. FIGS. 1C and 1D present pictorial views of prior art video cameras tethered to camcorders for implementing the tethered lens approach to capturing first-person video recording. FIG. 1C and FIG. 1D present Samsung™ devices.

These products are not generally hands-free products, and consumers have been employing their own unique mounting techniques to permit "hands-free" video recording of action sports activities. FIG. 1E presents a pictorial view of a tethered camera attempting to facilitate hands-free POV video recording. FIG. 1E presents a Blackeye™ device. These recent devices attempt to convey image data from "tethered" cameras to separate camcorders through IR signals to eliminate the tethering cables.

More recently, integrated hands-free, POV action sports video cameras have become available. FIGS. 2A and 2B present pictorial views of two prior art products implementing integrated solutions to first-person video recording. These products are still in their infancy and may be difficult to use well.

SUMMARY OF THE DISCLOSURE

Preferred embodiments of a portable digital video camera or camcorder (hereinafter collectively, "video camera") are equipped with global positioning system (GPS) technology for data acquisition and wireless connection protocol to provide remote image acquisition control and viewing. A wireless connection protocol, such as the Bluetooth® packet-based open wireless technology standard protocol, is used to provide control signals or stream data to a wearable video camera and to access image content stored on or streaming from a wearable video camera. Performing intelligent frame analysis of the image content enables picture setup optimization on one or more cameras simultaneously to enable multi-angle and three-dimensional video. A GPS receiver integrated in the video camera enables tracking of the location of the video camera as it acquires image information. The GPS receiver enables periodic capture of location once every few seconds with near pinpoint accuracy to bring together video and mapping. The inclusion of GPS technology introduces a new level of context to any video, making location, speed, time, and outside world conditions as important as the scene recorded. GPS capability makes it relatively easy to capture video within the action and share it online in seconds. For example, a user can watch an epic run down any mountain while tracking progress, speed, and elevation on a map. The GPS data, together with high definition video images, can be readily edited to organize video content, configure the video camera, and post stories online.

GPS ground plane customization and electrical coupling to the housing or other metal components of the video camera improves reception and performance. The ground plane is maximized by coupling it with an aluminum case that houses the video camera. The result is higher antenna gain and consequent enhanced signal reception when the video camera is mounted in multiple positions.

The video camera is configured with a signal path that allows for provision of a separate signal security module for use with only those applications that require the separate security module. An iPhone™ security module is packaged separately in a small subscriber identity module (SIM) card form factor.

Simplified mounting of the wearable video camera is accomplished by rotating the horizon 180° so that the video camera can be mounted fully upside down as the picture remains in the proper orientation. Rotation of the horizon may be accomplished electrically or mechanically. A rotating mount with a locking feature that allows adjustment of the angle of the video camera when it is attached to a mounting surface uses an adhesive, a strap, or another connection option. The video camera housing is equipped with a scissor spring to assist in moving a slide switch actuator over a long travel range. A user wearing the video camera uses the slide switch actuator to initiate video image recording.

The portable digital video camera includes a camera housing and a lens.

Some embodiments of the portable digital video camera comprise an integrated hands-free, POV action sports digital video camera.

Some embodiments of the portable digital video camera or the integrated hands-free, POV action sports digital video camera include an image sensor for capturing image data.

Some embodiments of the portable digital video camera or the integrated hands-free, POV action sports digital video camera include a manual horizon adjustment control for adjusting an orientation of a horizontal image plane recorded by the image sensor with respect to a housing plane of the camera housing.

Some embodiments of the portable digital video camera or the integrated hands-free, POV action sports digital video camera include a laser alignment system with one or more laser sources capable of projecting light emissions to define a horizontal projection axis that is coordinated with orientation of the horizontal image plane.

Some embodiments of the portable digital video camera or the integrated hands-free, POV action sports digital video camera include a microphone and a manually operable switch for controlling one or both of audio and video data capturing operations, the switch having an activator that may cover the microphone whenever the switch is in the OFF position.

Some embodiments of the portable digital video camera or the integrated hands-free, POV action sports digital video camera include a "quick-release" mounting system that can be used in conjunction with the laser alignment system to adjust the image capture orientation for pitch, yaw, and roll.

Additional aspects and advantages will be apparent from the following detailed description of preferred embodiments, which proceeds with reference to the accompanying drawings.

BRIEF DESCRIPTION OF THE DRAWINGS

FIGS. 3A, 3B, 3C, 3D, 3E, and 3F are, respectively, front perspective, back perspective, side elevation, front elevation, back elevation, and top plan views of an embodiment of an integrated hands-free, POV action sports digital video camera.

FIG. 7 is an exploded view of optical and mechanical components of an integrated hands-free, POV action sports digital video camera.

FIGS. 8A and 8B are fragmentary cross-sectional views of the lens system of the camera of FIG. 7, showing, respectively, a standard lens and the standard lens fitted with a lens filter.

FIG. 13A is a front perspective view of a pole mount system, employing the mount of FIG. 12.

FIGS. 13B and 13C are cross-sectional side views of a pole mount system showing, respectively, unlocked and locked configurations.

FIGS. 13D and 13E are front perspective views of a pole mount system showing, respectively, unlocked and locked configurations about a handle bar.

FIG. 14A is a front perspective view of an alternative pole mount system, employing the mount of FIG. 12 and a strap.

FIGS. 14B and 14C are respective side and front views of the alternative pole mount of FIG. 14A.

FIG. 14D is a front perspective view of the alternative pole mount of FIG. 14A locked about a pole.

FIG. 15A is a front perspective view of a goggle mount, employing a strap entrance facing in the opposite direction of the mounting rails.

FIG. 15B is a side elevation view of an alternative goggle mount, employing a strap entrance facing in the same direction of the mounting rails.

FIG. 15C is a fragmentary front perspective view of the alternative goggle mount of FIG. 15B mounted upon a goggle strap.

FIG. 16 is a front perspective view of a vented helmet mount, adapted for employing a strap for attachment to a vented helmet.

FIGS. 23A, 23B, 23C, 23D, and 23E, are, respectively, perspective, top plan, end elevation, side elevation, and bottom plan views of a slidable lockable member installed in the base mount of FIGS. 21 and 22.

FIGS. 25A, 25B, 25C, and 25D are front perspective views of the digital video camera of FIGS. 4A and 4B, showing its lens set in a vertical position, with the camera housing rotated 90° counter-clockwise, not rotated, rotated 90° clockwise, and rotated 180° to an inverted position, respectively, relative to the vertical position. FIG. 25E is a front elevation view of the digital video camera in the orientation of FIG. 25B annotated with dimension lines indicating ranges of angular displacement of a horizontal image plane achievable by manual rotation of the rotary horizontal adjustment controller.

FIG. 38 is a hybrid flow diagram and pictorial illustration of a mobile controller device paired by Bluetooth® wireless data and control command connection to two digital video cameras of FIGS. 26A, 26B, 27A, and 27B to implement a remote Start/Stop capability for multiple cameras.

DETAILED DESCRIPTION OF PREFERRED EMBODIMENTS

Figure 1A:
FIGS. 1A, 1B, 1C, 1D, and 1E constitute a set of pictorial views of five prior art products implementing a tethered lens approach to capturing first-person video recording.
Figure 1B:
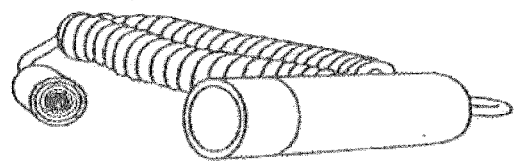
Figure 1C:
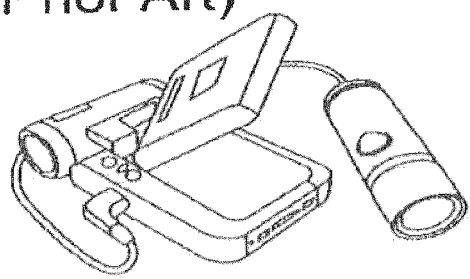
Figure 1D:
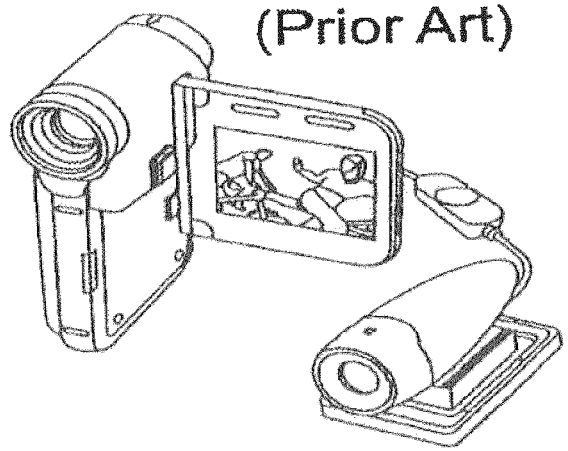
Figure 1E:
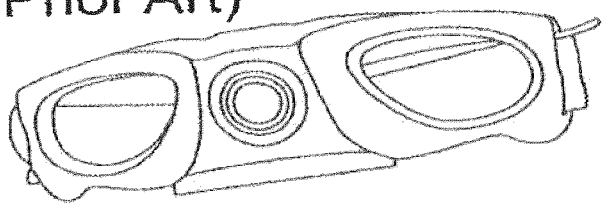
Figure 2A:
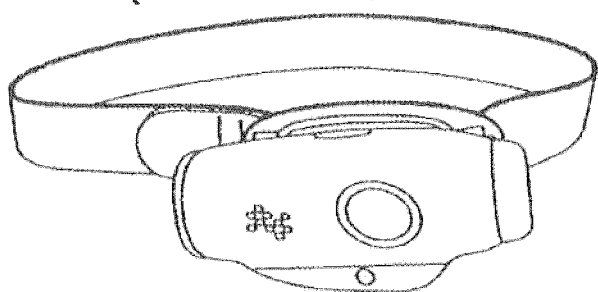
FIGS. 2A and 2B constitute a set of pictorial views of two prior art products implementing integrated solutions to first-person video recording.
Figure 2B:
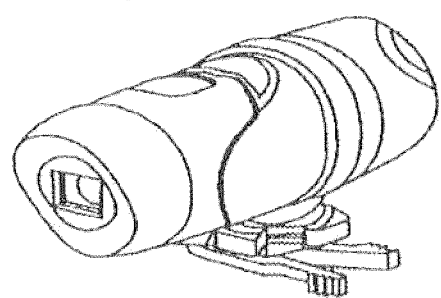
Figure 3A:
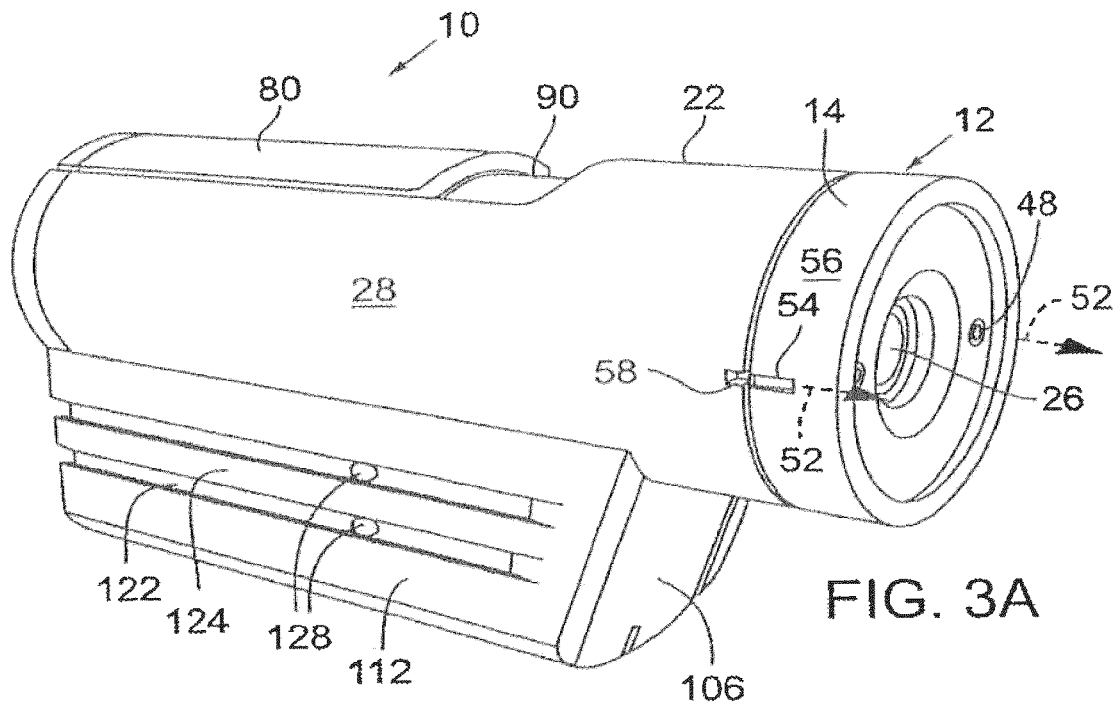
Figure 3B:
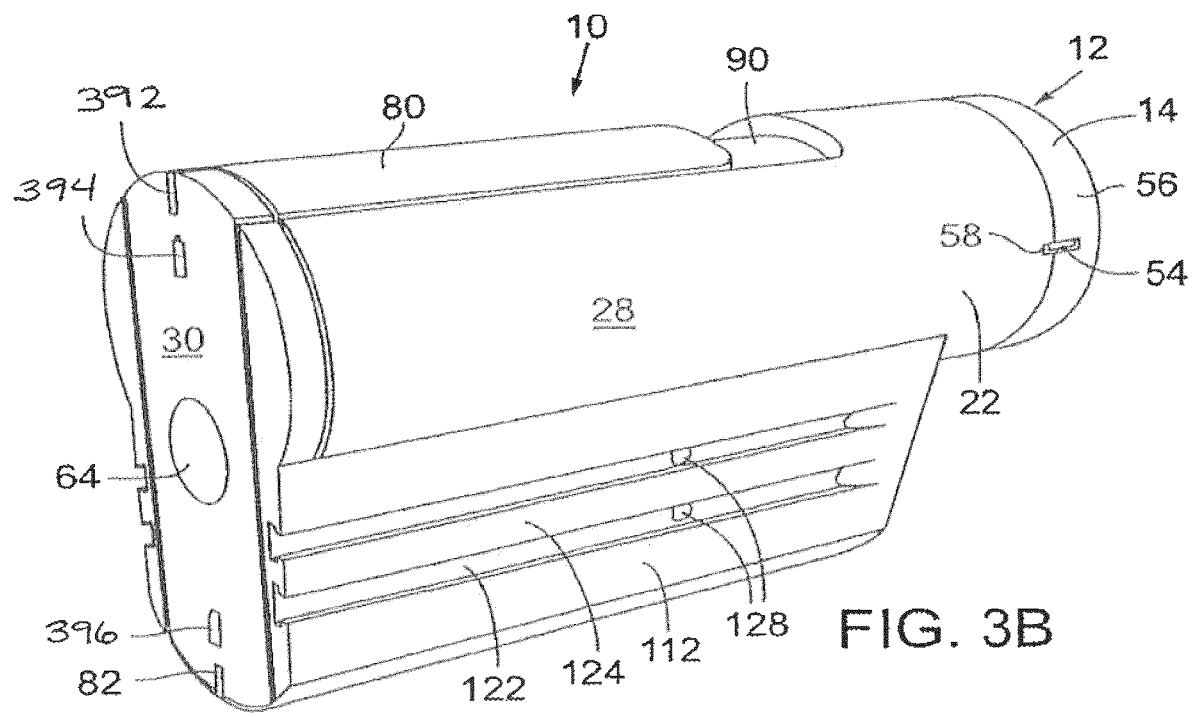
Figure 4A:
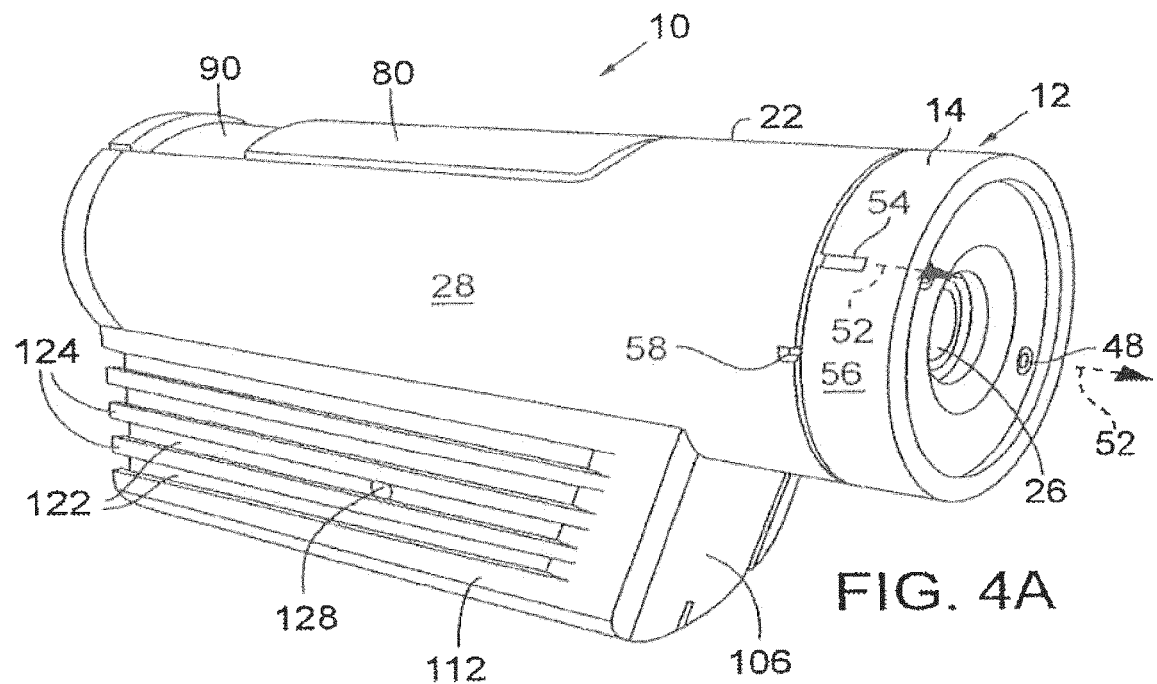
FIG. 4A is a front perspective view of an embodiment of an integrated hands-free, POV action sports digital video camera, showing alternative positioning of a switch and representative alternative rotation of a rotary horizontal adjustment controller.
Figure 4B:
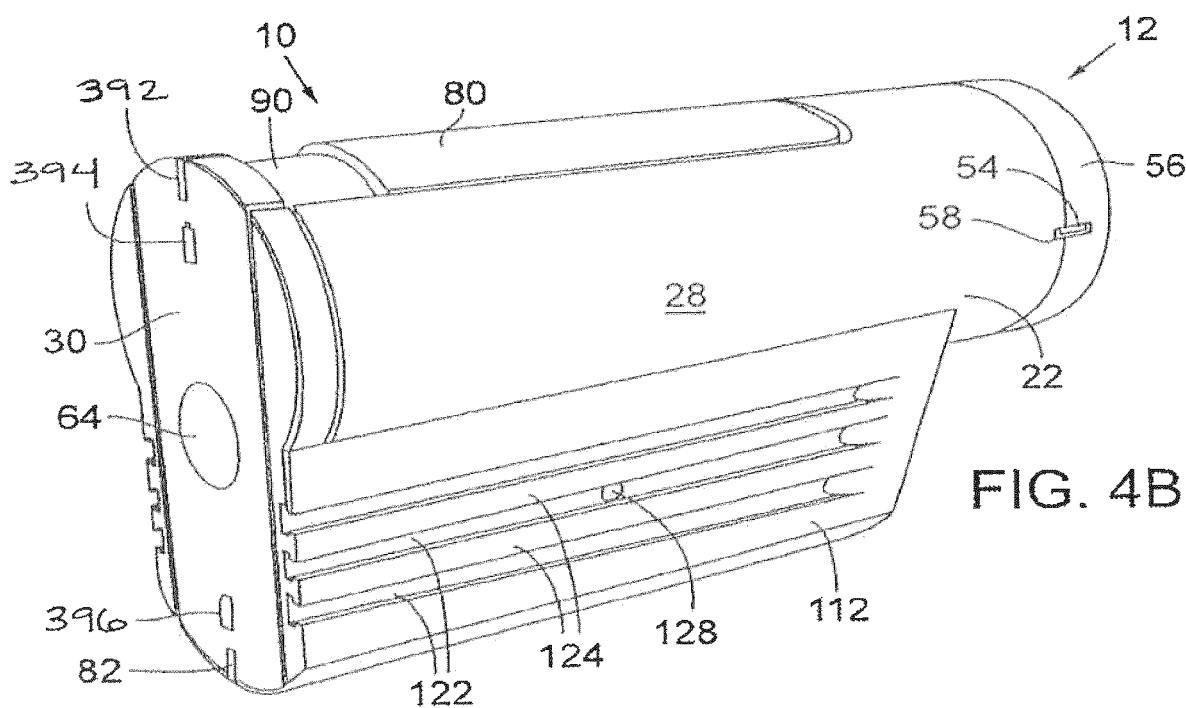
FIG. 4B is a back perspective view of an embodiment of an integrated hands-free, POV action sports digital video camera, showing a representative alternative number of rail cavities and an optional detent within a rail cavity.

FIGS. 3A, 3B, 3C, 3D, 3E, and 3F are, respectively, front perspective, back perspective, side elevation, front elevation, back elevation, and top plan views of an embodiment of an integrated hands-free, POV action sports digital video camera 10, and FIGS. 4A and 4B are front and back perspective views of, respectively, an alternative configuration and an alternative embodiment of digital video camera 10. For purposes of this description, the term "camera" is intended to cover camcorder(s) as well as camera(s). An example of such a digital video camera 10 is included in the Contour 1080P™ system, marketed by Contour, Inc., of Seattle, Washington.

FIGS. 5, 6, 7, 8A, and 8B show optical and mechanical components of digital video camera 10. With reference to FIGS. 3A-3F, 4A, 4B, 5, 6, 7, 8A, and 8B, some embodiments of digital video camera 10 include a manual horizon adjustment control system 12 including a manual horizon adjustment control for adjusting an orientation of a horizontal image plane 16 of an image recorded by an image sensor 18 with respect to a housing plane 20 (along a vertical cross-section) of a camera housing 22. An exemplary image sensor 18 may be a CMOS image capture card that provides for minimum illumination of 0.04 Lux @ f/1.2 and offers high sensitivity for low-light operation, low fixed pattern noise, anti-blooming, zero smearing, and low power consumption.

With reference to FIGS. 3A, 3C, 3F, 4A, 6, and 7, in some embodiments, the manual horizon adjustment control is a rotary controller 14 that rotates about a control axis 24 such that manual rotation of rotary controller 14 changes the orientation of horizontal image plane 16 with respect to housing plane 20. The manual horizon adjustment control can be used to offset horizontal image plane 16 with respect to the pitch, yaw, and roll of the mounting position of camera housing 22.

In some preferred embodiments, rotary controller 14 is positioned about a lens 26 and cooperates with a lens shroud 32 to support lens 26 within camera housing 22 such that manual rotation of rotary controller 14 rotates lens 26 with respect to camera housing 22. In other embodiments, lens 26 may remain fixed with respect to camera housing 22 even though rotary controller 14 rotates around lens 26. In some embodiments, lens 26 is a 3.6 mm focal length, four-element glass lens with a 135° viewing angle and a focal length covering a large range, such as from arm's length (e.g., 500 mm) to infinity, which focuses visual information onto image sensor 18 at a resolution such as at 1920×1080. Skilled persons will appreciate that a variety of types and sizes of suitable lenses are commercially available.

In some preferred embodiments, image sensor 18 is supported in rotational congruence with the orientation of rotary controller 14 such that manual rotation of rotary controller 14 rotates image sensor 18 with respect to housing plane 20 of camera housing 22. When image sensor 18 has a fixed relationship with the orientation of rotary controller 14, the image data captured by image sensor 18 do not require any post-capture horizon adjustment processing to obtain play back of the image data with a desired horizontal image plane 16. In particular, rotary controller 14 can be set to a desired horizontal image plane 16, and image sensor 18 will capture the image data with respect to the orientation of horizontal image plane 16. In some embodiments, image sensor 18 may remain fixed with respect to camera housing 22 even though rotary controller 14 rotates around image sensor 18.

With reference to FIGS. 6, 7, 8A, and 8B, in some embodiments, an exemplary optical assembly 34 shows how image sensor 18 and lens 26 may be supported in rotational congruence by the cooperation of lens shroud 32, an internal rotation controller 36, and rotary controller 14. In some preferred embodiments, rotary controller 14 may be separated from camera housing 22 by a gap 37 to facilitate the rotation of rotary controller 14 with respect to camera housing 22.

A lens cap holder 38 may be secured to rotary controller 14 by screw threads and cooperates with an O-ring 40a and to provide support for a lens cover 42 (such as a piece of glass). A lens holder 44 and a lens assembly holder 46 may also be employed to support lens 26 in a desired position with respect to the other components in optical assembly 34. Lens assembly holder 46 may be secured to lens cap holder 38 by screw threads and an O-ring 40b. An O-ring or bearings 43 may be employed between lens assembly holder 46 and a main housing 100 to facilitate the rotation of lens assembly holder 46 about control axis 24 with respect to main housing 100. A set screw 45 may be employed to secure lens assembly holder 46 of optical assembly 34 to main housing 100 without impeding the rotation of lens assembly holder 46 or the components within it. In some embodiments, rotary controller 14, lens cap holder 38, O-ring 40a, lens cover 42, lens shroud 32, laser sources 48, lens 26, lens holder 44, image sensor 18, internal rotation controller 36, O-ring 40b, and lens assembly holder 46 of optical assembly 34 may rotate together. Skilled persons will appreciate that several of these components may be fixed with respect to camera housing 22 or their synchronized rotation may be relaxed. For example, lens cover 42, lens 26, and lens holder 44 need not rotate.

With reference to FIG. 8B, rotary controller 14 may support a lens filter or other lens component, or rotary controller 14 may include screw threads or other means to enable attachment of additional or alternative lens components.

In some embodiments, rotary controller 14 cooperates with an encoder to orient image sensor 18 to a desired horizontal image plane 16. Alternatively, the encoder could guide post-capture horizon adjustment processing to adjust horizontal image plane 16 of the captured image so that it is transformed to play back the image data with the encoded horizontal image plane 16.

In some embodiments, rotary controller 14 is positioned in one or both of an arbitrary location away from lens 26 and an arbitrary relationship with the position of image sensor 18. For example, rotary controller 14 may be positioned on a side 28 of camera housing 22 or on a back door 30, and rotary controller 14 may remotely control the orientation of image sensor 18 or may control an encoder. Skilled persons will appreciate that an arbitrarily located manual horizon adjustment control need not be of a rotary type and may be of an electronic instead of a mechanical type.

In some embodiments, rotary controller 14 provides greater than or equal to 180° rotation of horizontal image plane 16 with respect to housing plane 20 of camera housing 22 in each of the clockwise and counterclockwise directions. In one example, rotary controller 14 provides 180° plus greater than or equal to 6° of additional rotation in each direction, providing a 360° rotation of horizontal image plane 16 with respect to housing plane 20. This adjustability includes embodiments in which the orientation of rotary controller 14 is in congruence with the orientation of image sensor 18, as well as embodiments employing an encoder. Preferably, both lens 26 and image sensor 18 rotate together 360° within a pivoting hermetically sealed capsule. This means that, no matter how an operator mounts digital video camera 10, image sensor 18 can be rotated to capture a level world.

With reference to FIGS. 4A and 4B, in some embodiments, a rotation indicator 54 is provided on an exterior surface 56 of rotary controller 14. Rotation indicator 54 may take the form of a horizontal notch or raised bar that may be of a different color from the color of camera housing 22. Camera housing 22 may have set in a fixed position a notch or raised bar 58 that is similar to or smaller than rotation indicator 54. Rotation indicator 54 and notch or raised bar 58 may be of the same color or of different colors. The angular extent of dislocation between rotation indicator 54 and notch 58 provides a physical indication of the amount that rotary controller 14 is displaced from its "home" position with respect to camera housing 22.

In some preferred embodiments, rotation indicator 54 and horizontal notch 58 are in a collinear alignment (in the "home" position) when horizontal image plane 16 is perpendicular to housing plane 20. Thus, if digital video camera 10 were set on a level horizontal surface and the two notches were collinear, horizontal image plane 16 would be horizontal.

With reference to FIGS. 3A, 3C, 3D, 3F, 4A, 7, and 8 in preferred embodiments, one or more laser sources 48 are fitted within rotary controller 14, are oriented with horizontal image plane 16, and are capable of projecting light emission(s) to define a horizontal projection axis or plane 52 that is parallel to or coplanar with horizontal image plane 16. Thus, manual rotation of rotary controller 14 changes the orientation of horizontal projection axis 52 with respect to housing plane 20 as the orientation of horizontal image plane 16 is changed with respect to horizontal projection axis 52. The beam(s) of light forming horizontal projection axis 52 can be used as a guide by an operator to facilitate adjustment of horizontal image plane 16 by simple rotation of rotary controller 14 after camera housing 22 has been mounted.

In some embodiments, a single laser source 48 may employ beam shaping optics and or a beam shaping aperture, filter, or film to provide a desired beam shape such as a line, lines of decreasing or increasing size, or a smiley face. In some embodiments, only a single beam shape is provided. In some embodiments, multiple beam shapes are provided and can be exchanged such as through manual or electronic rotation of a laser filter. Skilled persons will appreciate that two or more laser sources 48 may be outfitted with beam shaping capabilities that cooperate with each other to provide horizontal projection axis 52 or an image that provides horizontal projection axis 52 or other guidance tool.

In some embodiments, two laser sources 48 (or two groups of laser sources) are employed to project two beams of light that determine horizontal projection axis 52. Two laser sources 48 may be mounted on opposite sides of lens 26 such that their positions determine a laser mounting axis that bisects lens 26. In some embodiments, lens shroud 32 provides support for laser sources 48 such that they are positioned to emit light through apertures 60 in lens shroud 32 (FIG. 7). In some embodiments, an alternative or additional optical support barrel 32a may support laser source 48 and the other optical components.

Laser sources 48 may be diode lasers that are similar to those used in laser pointers. Laser sources 48 preferably project the same wavelength(s) of light. In some embodiments, an operator may select between a few different wavelengths, such as for red or green, depending on contrast with the background colors. In some embodiments, two wavelengths may be projected simultaneously or alternately. For example, four laser sources may be employed with red and green laser sources 48 positioned on each side of lens 26 such that red and green horizontal projection axes 52 are projected simultaneously or alternately in the event that one of the colors does not contrast with the background.

In some embodiments, laser sources 48 may be responsive to a power switch or button 64, which in some examples may be located on back door 30 of camera housing 22. A rotation of horizon adjustment control system 12 or rotary controller 14 may provide laser sources 48 with an ON condition responsive to a timer, which may be preset such as for five seconds or may be a user selectable time period. Alternatively, a single press of button 64 may provide laser sources 48 with an ON condition with a second press of button 64 providing an OFF condition. Alternatively, a single press of button 64 may provide an ON condition responsive to a timer, which may be preset such as for five seconds or may be a user selectable time period. Alternatively, button 64 may require continuous pressure to maintain laser sources 48 in an ON condition. Button 64 may also control other functions such as standby mode. Skilled persons will appreciate that many variations are possible and are well within the domain of skilled practitioners.

Skilled persons will also appreciate that any type of video screen, such as those common to conventional camcorders, may be connected to or be a part of camera housing 22. Such video screen and any associated touch display may also be used as feedback for orientation in conjunction with or separately from laser sources 48. Skilled persons will appreciate that the video screen may take the form of a microdisplay mounted internally to camera housing 22 with a viewing window to the screen through camera housing 22 or may take the form of an external LCD screen.

With reference to FIGS. 3A, 3B, 3C, 3F, 4A, 4B, 5, and 6, in preferred embodiments, digital video camera 10 has a manually operable switch activator 80 that controls one or both of the recording condition of image sensor 18 and conveyance of the acquired image data to a data storage medium, such as on a two-gigabyte MicroSD card. In some embodiments, digital video camera 10 is designed to use pulse power to conserve battery life while monitoring switch activator 80. When switch activator 80 is positioned to the ON position, the pulse power system is instructed to provide full power to the electronics and begin recording immediately; similarly, when switch activator 80 is positioned to the OFF position, the pulse power system is instructed to cut power to the electronics and stop recording immediately.

In some preferred embodiments, when switch activator 80 is slid or toggled, it moves a magnetic reed that is recognized from an impulse power sensor. Once the sensor recognizes the magnetic reed has been toggled to the ON position, the pulse power system is then triggered to power up most or all of the electronics of digital video camera 10, including all of the electronics required for recording as well as selected other electronics or simply all the electronics. Once full power is provided to the system electronics, a feed from image sensor 18 begins encoding and writing to the data storage medium. As soon as the first frames are written to the data storage medium, a signal is sent to an LED 82 to indicate via a light pipe 84 that digital video camera 10 is recording. Thus, activation of switch activator 80 initiates recording nearly instantaneously.

In some embodiments, switch activator 80 powers up the electronics and initiates recording from a standby mode such as after button 64 has been pushed to activate the pulse power mode. In other embodiments, switch activator 80 powers up the electronics and initiates recording directly without any pre-activation. In some embodiments, a video encoder that cooperates with image sensor 18 and a microprocessor provides instructions to the video encoder. In some embodiments, switch activator 80 is adapted to substantially simultaneously control supply of power to the microprocessor, image sensor 18, and the video encoder, such that when switch activator 80 is placed in the ON position the microprocessor, image sensor 18, and the video encoder all receive power substantially concurrently and thereby substantially instantaneously initiate a video data capturing operation.

In some embodiments, an audio encoder cooperates with a microphone 90, and the microprocessor provides instructions to the audio encoder. In some embodiments, switch activator 80 is adapted to substantially simultaneously control the supply of power to microphone 90 and the audio encoder such that when switch activator 80 is placed in the ON position, the microprocessor, microphone 90, and the audio encoder all receive power substantially concurrently and thereby substantially instantaneously initiate an audio data capturing operation.

In some embodiments, when switch activator 80 is placed in the OFF position, the microprocessor, image sensor 18, and the video encoder all cease to receive power substantially concurrently and thereby substantially instantaneously cease the video data capturing operation. In some embodiments, when switch activator 80 is placed in the OFF position, the microprocessor, microphone 90, and the audio encoder all cease to receive power substantially concurrently and thereby substantially instantaneously cease the audio data capturing operation.

In some embodiments, the microprocessor, image sensor 18, the video encoder, microphone 90, and the audio encoder all receive power substantially concurrently and thereby substantially instantaneously initiate the video data and audio data capturing operations. In some embodiments, the microprocessor, image sensor 18, the video encoder, microphone 90, and the audio encoder all cease to receive power substantially concurrently and thereby substantially instantaneously cease the video data and audio data capturing operations.

In some embodiments, switch activator 80 controls supply of power to additional electronics such that the additional electronics are deactivated when switch activator 80 is in the OFF position and such that the additional electronics are activated when switch activator 80 is in the ON position.

Skilled persons will appreciate that switch activator 80 may be designed to have more than two slide settings. For example, in addition to ON and OFF settings for recording, switch activator 80 may provide an intermediate setting to activate laser sources 48, to activate one or more status indicators, or initiate other functions in digital video camera 10.

The use of a magnetic reed switch as an embodiment for switch activator 80 prevents water or other fluids from entering through the camera housing 22. Skilled persons will appreciate that other waterproof ON/OFF switch designs are possible. In preferred embodiments, digital video camera 10 also employs a waterproof microphone 90, such as an omni-directional microphone with a sensitivity (0 dB=1V/Pa, 1 KHz) of −44±2 dB and a frequency range of 100-10,000 Hz, for capturing audio data and providing them to the data storage medium or to a second data storage medium. Alternatively, camera housing 22 may include breathable, watertight materials (such as GoreTex™) to prevent the egress of water without requiring a waterproof microphone 90. Skilled persons will appreciate microphones with a large variety of operational parameters that are suitable for microphone 90 are commercially available or can be manufactured to suit desired criteria.

In some embodiments, microphone 90 is positioned beneath switch activator 80 such that switch activator 80 covers microphone 90 whenever switch activator 80 is in the OFF position and such that switch activator 80 exposes microphone 90 whenever switch activator 80 is in the ON position. The audio data capturing operation is preferably deactivated when switch activator 80 is in the OFF position and that the audio data capturing operation is preferably activated when switch activator 80 is in the ON position. The ON and OFF conditions of the audio data capturing operation may be controlled by switch activator 80 in conjunction with the ON and OFF conditions of the video capturing operation.

Figure 5:
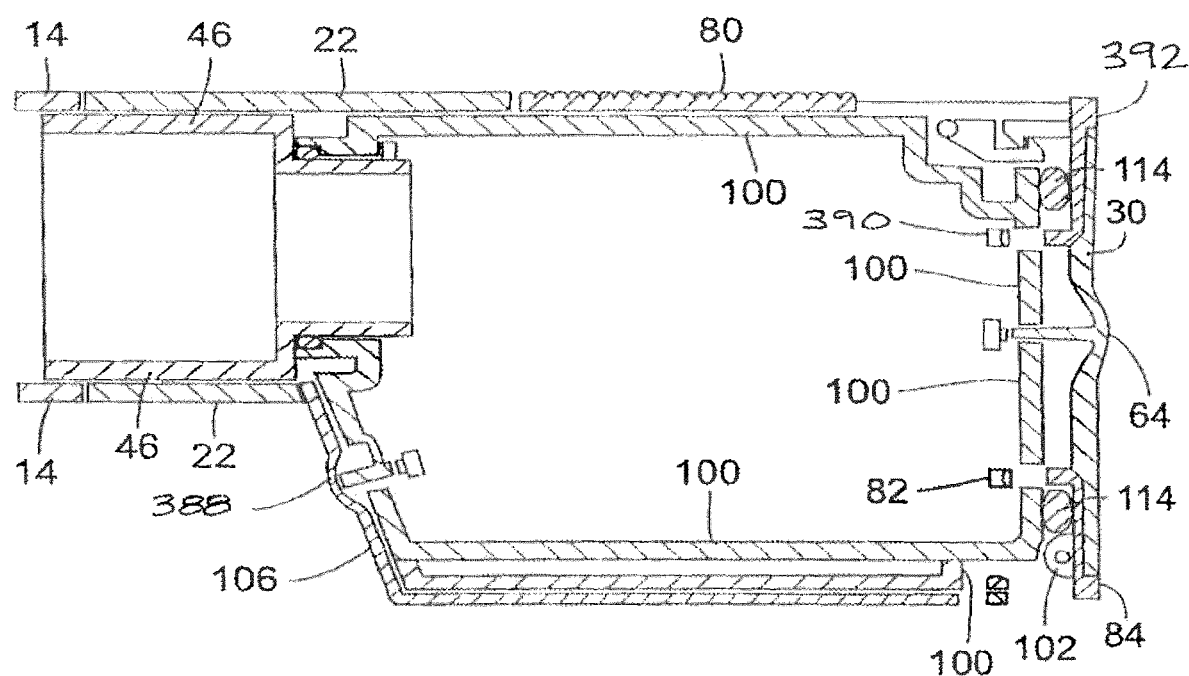
FIG. 5 is a cross-sectional side view of an embodiment of an integrated hands-free, POV action sports digital video camera.
Figure 6:
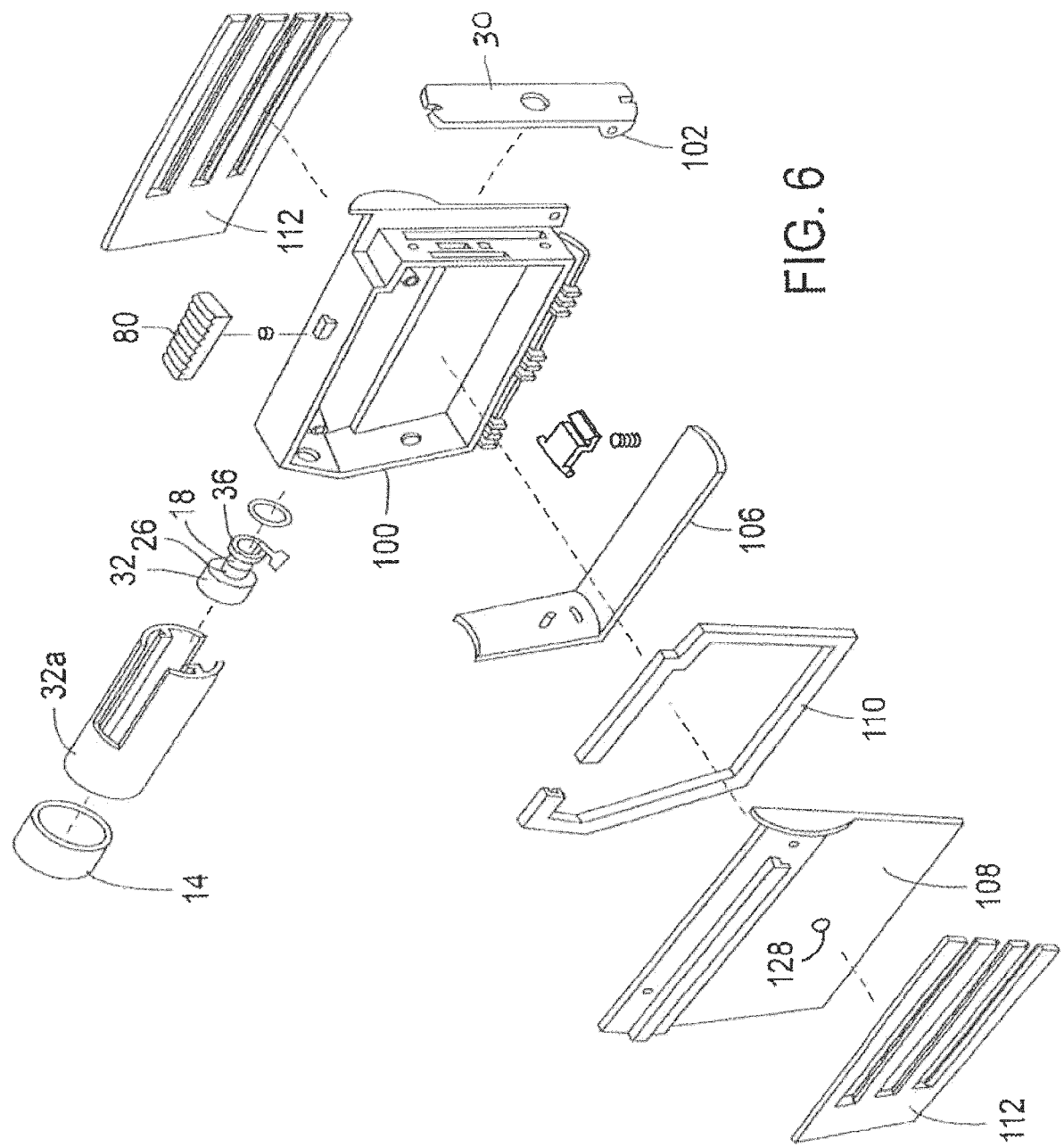
FIG. 6 is an exploded view of mechanical components of an embodiment of an integrated hands-free, POV action sports digital video camera.

With reference to FIGS. 5 and 6, in some embodiments, camera housing 22 includes main housing 100 that supports switch activator 80, a front and bottom trim piece 106, and back door 30 which is connected to main housing 100 through a hinge 102. In some embodiments, back door 30 may be removable through its hinge 102 to allow connection of accessories to main housing 100 for extended functionality. Back door 30 may provide an area of thinner material to permit compression of button 64. Gaskets 114 may be seated between main housing 100 and back door 30 to provide waterproofing. A housing cover 108 may be connected to main housing 100 through a rubber gasket 110 that also enhances the waterproof characteristics of camera housing 22.

Side caps 112 may be ultrasonically welded to the exterior surfaces of housing cover 108 and the lower portion of main housing 100, which form the lower portions of sides 28 of camera housing 22. In some embodiments camera housing 22 is made from brushed aluminum, baked fiberglass, and rubber. In particular, main housing 100, housing cover 108, and side caps 112 may be made from aluminum. Front and bottom trim piece 106 may also be ultrasonically welded to main housing 100.

With reference to FIGS. 3A, 3B, 4A, 4B, 6, and 9, in preferred embodiments, digital video camera 10 includes part of a mounting system 120 that has two or more housing rail cavities 122 and two or more interleaved housing rails 124 on each side 28 of camera housing 22 for engaging a versatile mount 126. An example of such a mounting system 120 is the TRail™ mounting system, marketed by Contour, Inc. of Seattle, Washington.

Housing rail cavities 122 and housing rails 124 may be formed by cut outs in side caps 112 that are mounted to main housing 100. In some embodiments, digital video camera 10 is bilaterally symmetrical and has an equal number of housing rail cavities 122 on each of side caps 112 and an equal number of housing rails 124 on each of side caps 112. In some embodiments, digital video camera 10 may for example provide two housing rail cavities 122 (such as shown in FIGS. 3A and 3B) or three housing rail cavities 122 in each side cap 112 (such as shown in FIGS. 4A and 4B). Skilled persons will appreciate, however, that in some embodiments, digital video camera 10 need not be symmetrical and may have an unequal number of rail cavities 122 on its side caps 112.

In some embodiments, rail cavities 122 have a "T"-like, wedge-like, or trapezoid-like cross-sectional appearance. Skilled persons will appreciate that the dimensions of the stem or lateral branches of the "T" can be different. For example, the stem can be thicker than the branches, or one or more of the branches may be thicker than the stem; similarly, the stem can be longer than the branches, and one or more of the branches may be longer than the stem. The cross-sectional shapes may have flat edges or corners, or the edges or corners may be rounded. Skilled persons will also appreciate that numerous other cross-sectional shapes for rail cavities 122 are possible and that the cross-sectional shapes of different housing rail cavities 122 need not be the same whether in the same side cap 112 or in different side caps 112. Similarly, housing rail cavities 122 may have different lengths and housing rails 124 may have different lengths. The bottom of trim piece 106 may be alternatively or additionally fitted with housing rails 124.

In some embodiments, one or more of housing rail cavities 122 may contain one or more bumps or detents 128. In some embodiments, each side 28 of camera housing 22 contains at least one bump or detent 128. In some embodiments, each housing rail cavity 122 contains at least one bump or detent 128. In some examples, however, only a single housing rail cavity 122 on each side 28 contains a bump or detent 128. Skilled persons will appreciate that the different sides 28 need not contain the same number of bumps or detents 128.

Figure 9:
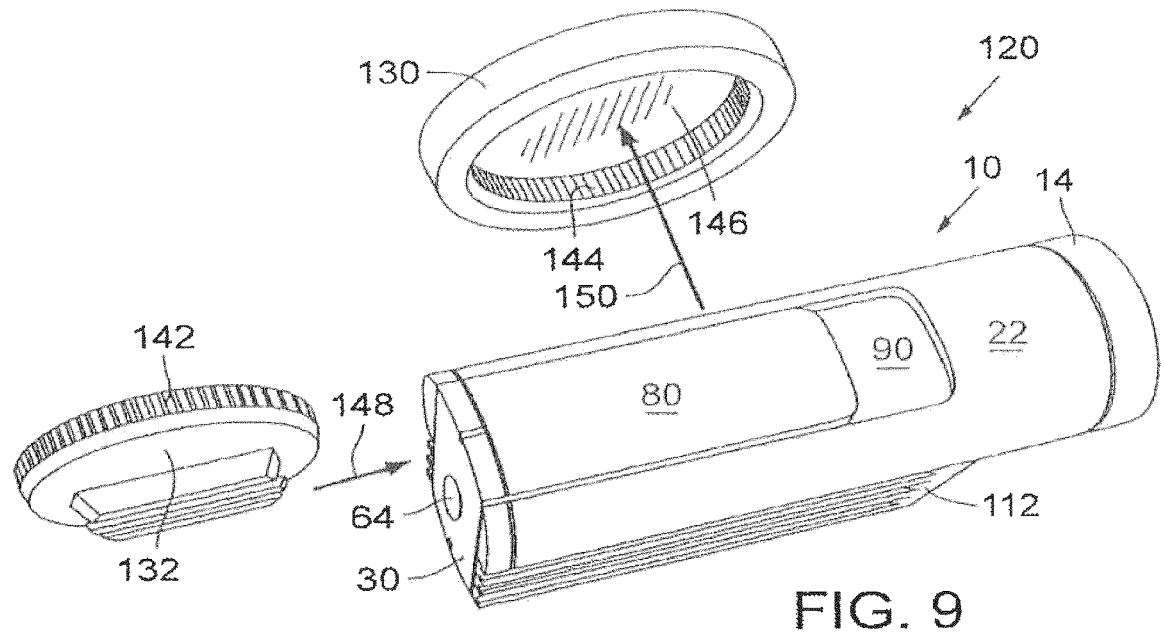
FIG. 9 is a partly exploded view of a versatile mounting system demonstrating ease of adjustment of camera mount orientation coupled with ease of camera detachment with retention of the mount orientation.
Figure 10:
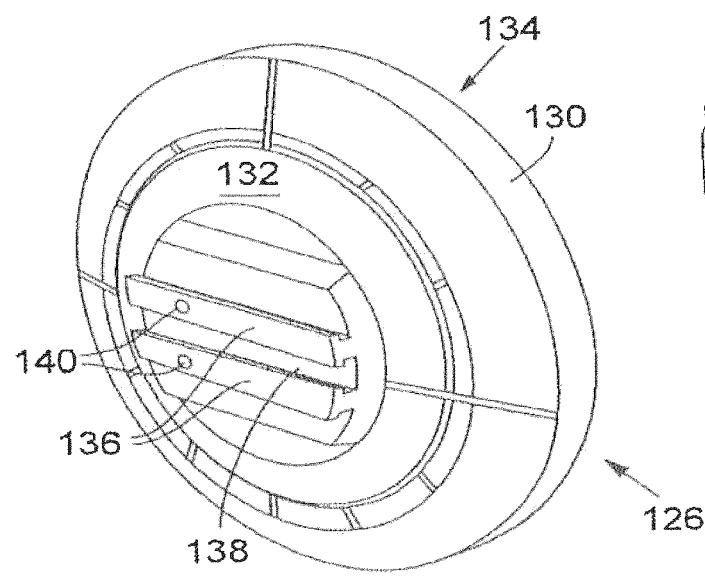
FIG. 10 is a front perspective view of a standard mount, employing a rail plug having two rails and two detents.

FIG. 9 shows a base mount 130 and a rail plug 132 that fit together to form a flat surface mount 134 shown in FIG. 10. FIGS. 11A-11D (FIG. 11) depict different views of camera housing 22 mated with flat surface mount 134. With reference to FIGS. 9-11, rail plug 132 contains one or more mount rails 136 that are adapted to mate with housing rail cavities 122 on camera housing 22. Similarly, rail plug 132 contains one or more mount rail cavities 138 that are adapted to mate with housing rails 124 on camera housing 22. Mount rails 136 may have the same or different cross-sectional shapes as those of housing rails 124, and mount rail cavities 138 may have the same or different cross-sectional shapes as those of housing rail cavities 122. In some preferred embodiments, rails 124 and 136 and cavities 122 and 138 have the same cross-sectional profiles.

In some embodiments, one or more of mount rails 136 on rail plug 132 may contain one or more detents or bumps 140. In some embodiments, each mount rail 136 contains at least one detent or bump 140. In some examples, however, only a single mount rail 136 contains a detent or bump 140. The detents or bumps 140 are adapted to mate with bumps or detents 128 such that if camera housing 22 has detents 128 then rail plug 132 has bumps 140 or if camera housing 22 has bumps 128 then rail plug 132 has detents 140. Skilled persons will appreciate that in some alternative embodiments, housing rails 124 have bumps or detents 128 and mount rail cavities 138 have detents or bumps 140.

The versatile mounting system 120 provides for ease of mounting and orientation of digital video camera 10 with ease of detachment of digital video camera 10 with retention of the mounted orientation. In some embodiments, base mount 130 may have a very small footprint and may be attached to a surface with an adhesive pad designed for outdoor use. After base mount 130 has been attached to a surface, rail plug 132 can be detached from base mount 130.

In some embodiments, rail plug 132 has a circumferential sawtoothed edge 142 that is mated to a sawtooth-receiving inside edge 144 of a base mount cavity 146 adapted to receive rail plug 132. In some embodiments, rail plug 132 has a compression fit within base mount 130. In some embodiments, hook and loop double-toothed Velcro™ may be used instead of or in addition to a compression fit technique to further secure rail plug 132 within base mount 130.

Mount rails 136 of rail plug 132 can slide into housing rail cavities 122 of camera housing 22 as mount rail cavities 138 of rail plug 132 slide onto housing rails 124 of camera housing 22 as indicated by a direction arrow 148 (FIG. 9) to secure rail plug 132 to camera housing 22. The mated detents and bumps 128 and 140 can be engaged to prevent unintended lateral movement of rail plug 132 with respect to camera housing 22. Rail plug 132 with the attached digital video camera 10 can be rotated from zero to 360 degrees about an axis perpendicular to base mount 130 to capture a desired viewing angle. Then, rail plug 132 can be inserted or re-inserted into base mount 130 as indicated by a direction arrow 150 (FIG. 9). FIG. 11 shows from several different views how digital video camera 10, rail plug 132, and base mount 130 appear when they are mated together.

In some embodiments, rail plug 132 and base mount 130 may be made from a hard, but flexible material such as rubber or a polymer with similar properties, but skilled persons will appreciate that rail plug 132 and base mount 130 may be made from a hard or soft plastic. Because base mount 130 can be flexible, it can be attached to a variety of surfaces such as, for example, the surfaces of helmets, snowboard decks, skis, fuel tanks, windows, doors, and vehicle hoods. The type and flexibility of the material of flat mount 126 may provide a "rubber" dampening effect as well as enhance rail sliding, rail engagement, and plug engagement. Mounting system 120 may also include a runaway leash (not shown).

When recording of an activity is completed, rail plug 132 with the attached digital video camera 10 may be disengaged from base mount 130 for safe storage or data uploading. Base mount 130 can be left attached to the surface and need not be re-attached and/or re-adjusted. Alternatively, camera housing 22 may be disengaged from rail plug 132, leaving rail plug 132 engaged with base mount 130 so that the original orientation of mount rails 136 of rail plug 132 is maintained to permit quick reattachment of digital video camera 10 without requiring its orientation to be re-adjusted to base mount 130 or the person, equipment, or vehicle to which base mount 130 is mounted.

Figure 12:
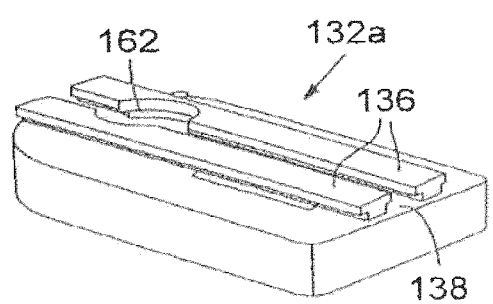
FIG. 12 is a perspective view of an alternative mount, employing two mounting rails and two detents.
Figure 11B:
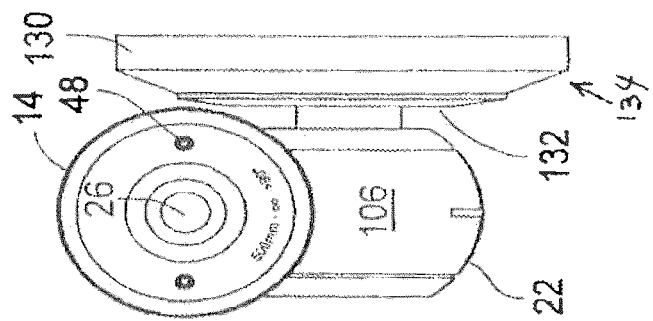
FIGS. 11A, 11B, 11C, and 11D are, respectively, back elevation, front elevation, side elevation, and top plan views of the versatile mounting system, demonstrating the matable relationship between the camera of FIGS. 3A-3E with the standard mount shown in FIG. 10.
Figure 11C:
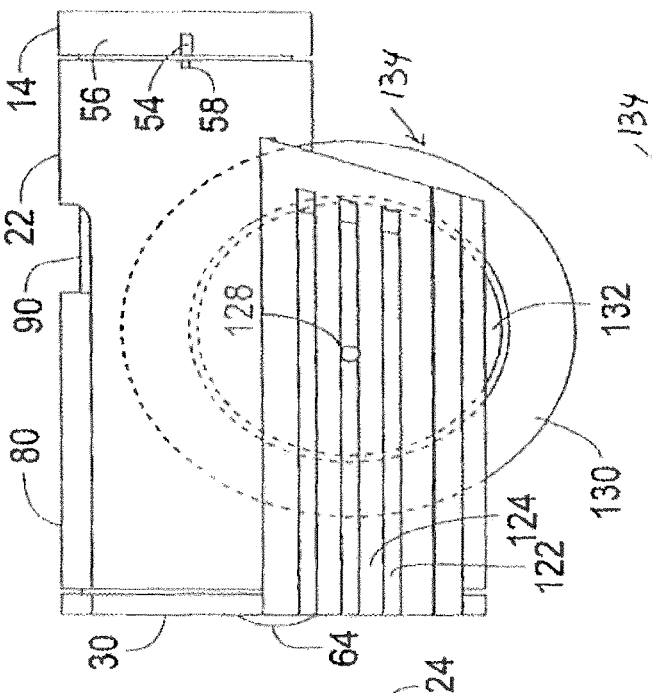
Figure 11D:
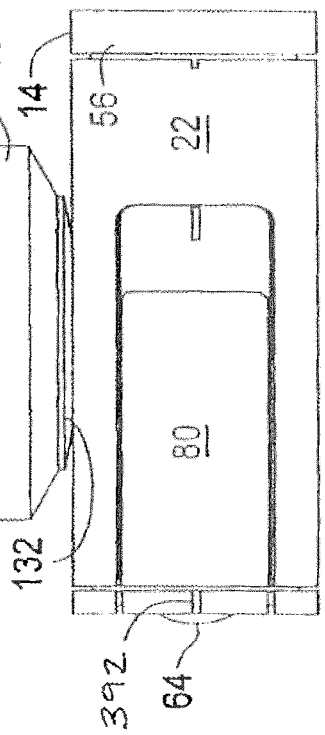
Figure 11A:
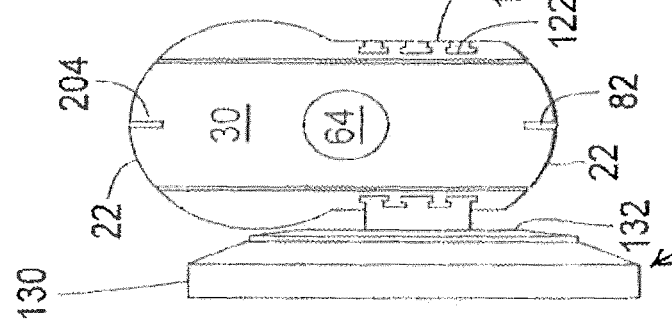

FIG. 12 shows an alternative rail plug 132a; and FIGS. 13A, 13B, 13C, 13D, and 13E (FIG. 13) show several views of rail plug 132a with an alternative base mount 130a, including locked and unlocked configurations, to form a pole mount 126a for mounting on a pole 160 such as handle bars. With reference to FIGS. 12 and 13, rail plug 132a may be used as a standalone mount with an adhesive backing, or it may be used in conjunction with or integrated into one or more varieties of base mounts 130a. Rail plug 132a may be attached to base mount 130a through the use of an adhesive mounting, through the use of Velcro™, through the use of a screw, through the use of other conventionally known means, or combinations thereof. Mount rails 136 may be formed to provide an aperture 162 to provide access for a screw and screwdriver to mount rail plug 132a onto base mount 130a.

Base mount 130a is configured to open and close around poles 160, particularly poles of standardized recreational equipment and especially such poles having small diameters of about 1-1.5 inches (2.5-3.8 cm). In some embodiments, base mount 130a has a locking pin 164 with a head 166 that can be secured within a lock chamber 168. Locking pin 164 increases compression against pole 160 to prevent base mount 130a from rotating around pole 160 after its desired positioned is established. Base mount 130a may also be provided with a pin door cover 170 to prevent debris from accessing locking pin 164 or lock chamber 168.

FIGS. 14A, 14B, 14C, 14D, and 14E (FIG. 14) show several views of a rail plug 132b with an alternative base mount 130b, including a strap 172, to form a pole mount 126b for mounting on a pole 160b such as a roll cage, a windsurfing mast, or a hang glider support. With reference to FIG. 14, in some embodiments, strap 172 is large enough to accommodate poles 160b having a diameter up to 4 inches (12 cm) or larger. In some embodiments, a dial 174 may be employed to tighten and loosen strap 172. In other embodiments, dial 174 controls the swivel of rail plug 132b with respect to base mount 130b so that the side-to-side angle of digital video camera 10 can be adjusted. As with rail plug 132a, rail plug 132b may be attachable to base mount 130b or may be integrated with it.

FIGS. 15A, 15B, and 15C (FIG. 15) show several views of a rail plug 132c attached to or integrated with alternative base mounts 130c and 130e of respective band or strap mounts 126c and 126e for mounting on a belt, strap, or band 180, such as a band 180 of a pair of goggles 182. With reference to FIG. 15A, base mount 130e has a dampener 184a and a strap entrance 186a on an interior side of the base mount 130e, i.e., facing in the direction opposite to that mount rails 136 face. Dampener 184a may be made from rubber or other suitable cushioning material to cushion a user's head away from digital video camera 10.

With reference to FIG. 15B, a dampener 184b is provided on an interior side of base mount 130c, i.e., facing in the direction opposite to that mount rails 136 face. However, a strap entrance 186b is provided on an exterior side of base mount 130c, i.e., facing in the same direction that mount rails 136 face. FIG. 15C shows base mount 130c of FIG. 15B mounted upon strap 180 of goggles 182. Skilled persons will appreciate that the rail plug 132a can be substituted for rail plug 132c.

FIG. 16 shows a rail plug 132d with an alternative base mount 130d of a helmet mount 126d for mounting on a vented helmet. Helmet mount 126d includes one or more slots 190 through which a strap can be used to secure base mount 130d to a helmet through vent slots in the helmet. Skilled persons will appreciate that rail plug 132a can be substituted for rail plug 132d.

Figure 17:
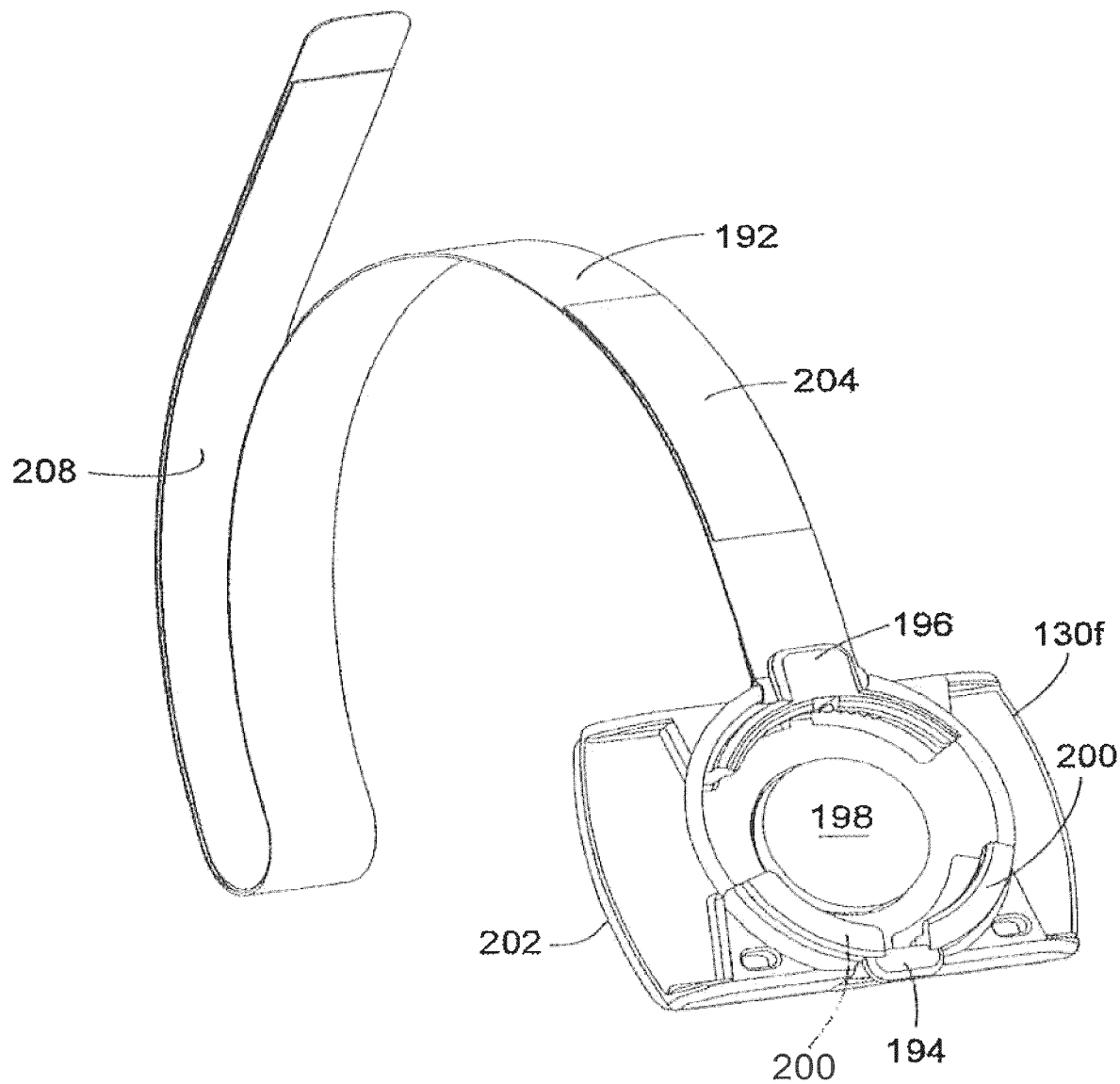
FIG. 17 is a front perspective view of another alternative goggle mount, adapted for employing a strap for attachment to a goggle strap.

FIG. 17 is a front perspective view of another alternative goggle base mount 130f, adapted for employing a strap 192 for attachment to goggle band 180 (FIG. 15C). Strap 192 can be looped through buckles 194 and 196 to secure base mount 130f to goggle band 180. Base mount 130f is adapted to receive circular rail plug 132 (FIG. 10) that permits 360-degree rotation of mount rails 136. Such embodiments permit a user adjust the angle of digital video camera 10 to be different from the vertical viewing angle of the user. For example, the user can be viewing down at the ground while digital video camera 10 (and its image sensor 18) captures images straight ahead. In some embodiments, base mount 130f may include pads 198 and 202 to dampen against vibrations and may include retaining tabs 200 to prevent rail plug 132 from being inadvertently jarred loose. Strap 192 may also or alternatively include pads 204 and 208.

Figure 18:
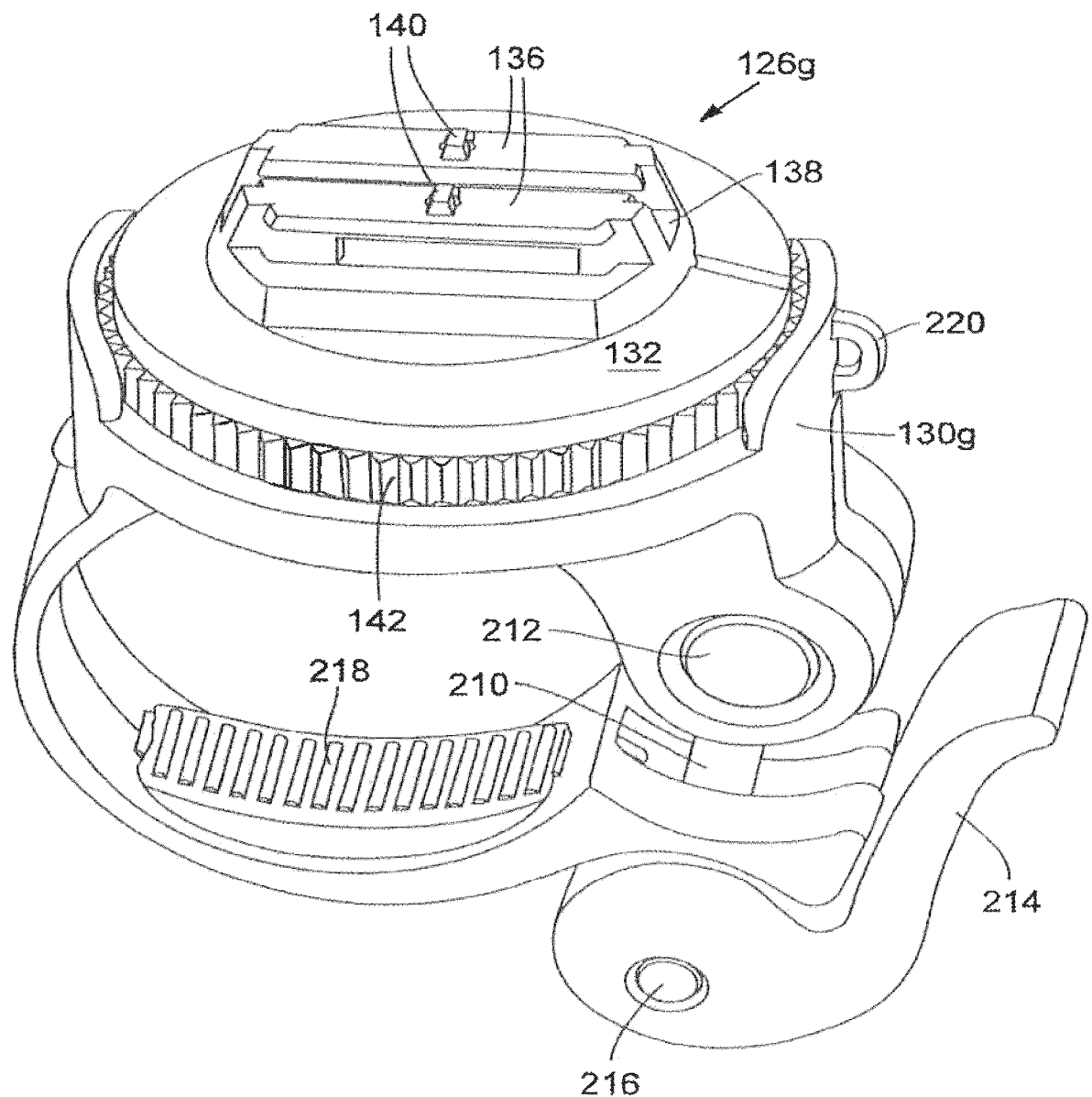
FIG. 18 is a front perspective view of an alternative pole mount system, employing the rail plug of FIG. 10.

Skilled persons will appreciate that base mounts 130a through 130d can also alternatively be configured to receive a round rail plug 132 (of FIG. 10) that permits 360-degree rotation of mounting rails 136. For example, FIG. 18 shows an alternative pole mount 126g having a base mount 130g adapted to receive circular rail plug 132 that permits 360-degree rotation of mount rails 136. Such embodiments can facilitate compensation for handle bars or other poles 160 or 160b that may be angled backward or forward.

In some embodiments, base mount 130g has a different locking mechanism from that of base mount 130a (FIG. 13). For example, in some embodiments, a locking pin 210 is attached by a hinge 212 to base mount 130g, and locking pin 210 is attached at its other end to a pin door cover 214 through a hinge 216. Locking pin 210 cooperates with hinge door cover 214 to increase compression against pole 160 to prevent base mount 130g from rotating around pole 160 after its desired position is established. Skilled persons will appreciate that base mount 130a may alternatively employ this locking mechanism. In some embodiments, base mounts 130a and 130g include a pole grip 218 to help maintain a preferred orientation of base mounts 130a and 130g with respect to pole 160. In some embodiments, base mounts 130 and 130a-130g may include a leash ring 220 adapted to receive a lease line that may be attached to an associated rail plug 132 and 132a-132d, digital video camera 10, or the operator.

Figure 19:
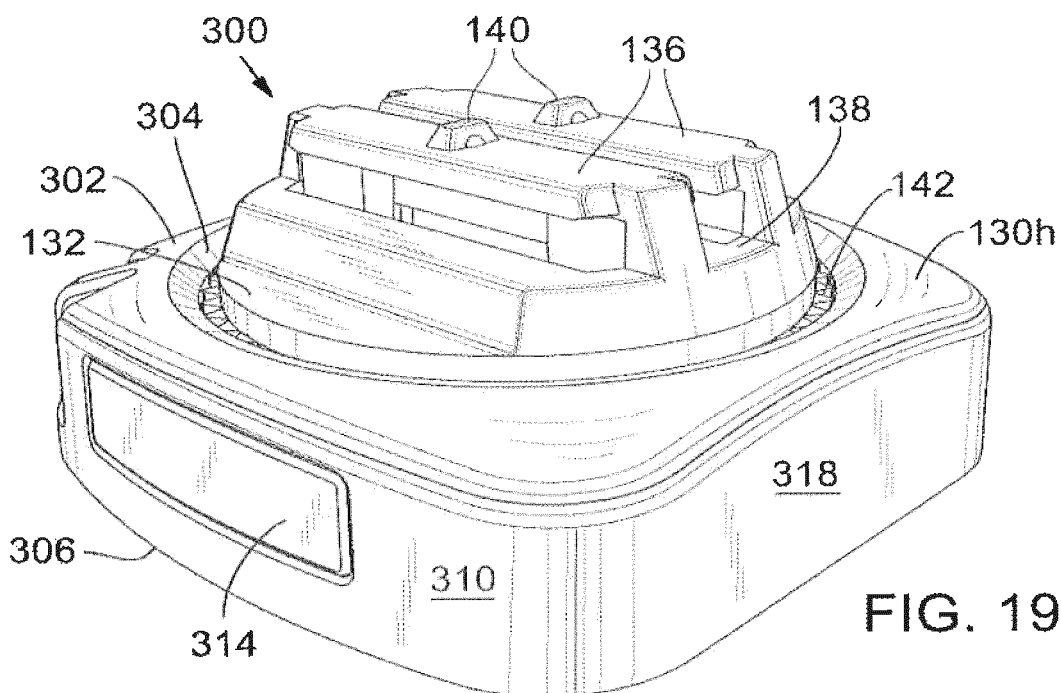
FIGS. 19 and 20 are, respectively, perspective and top plan views of a mounting system comprising a rotating circular rail plug set in a base mount configured with a locking feature.
Figure 20:
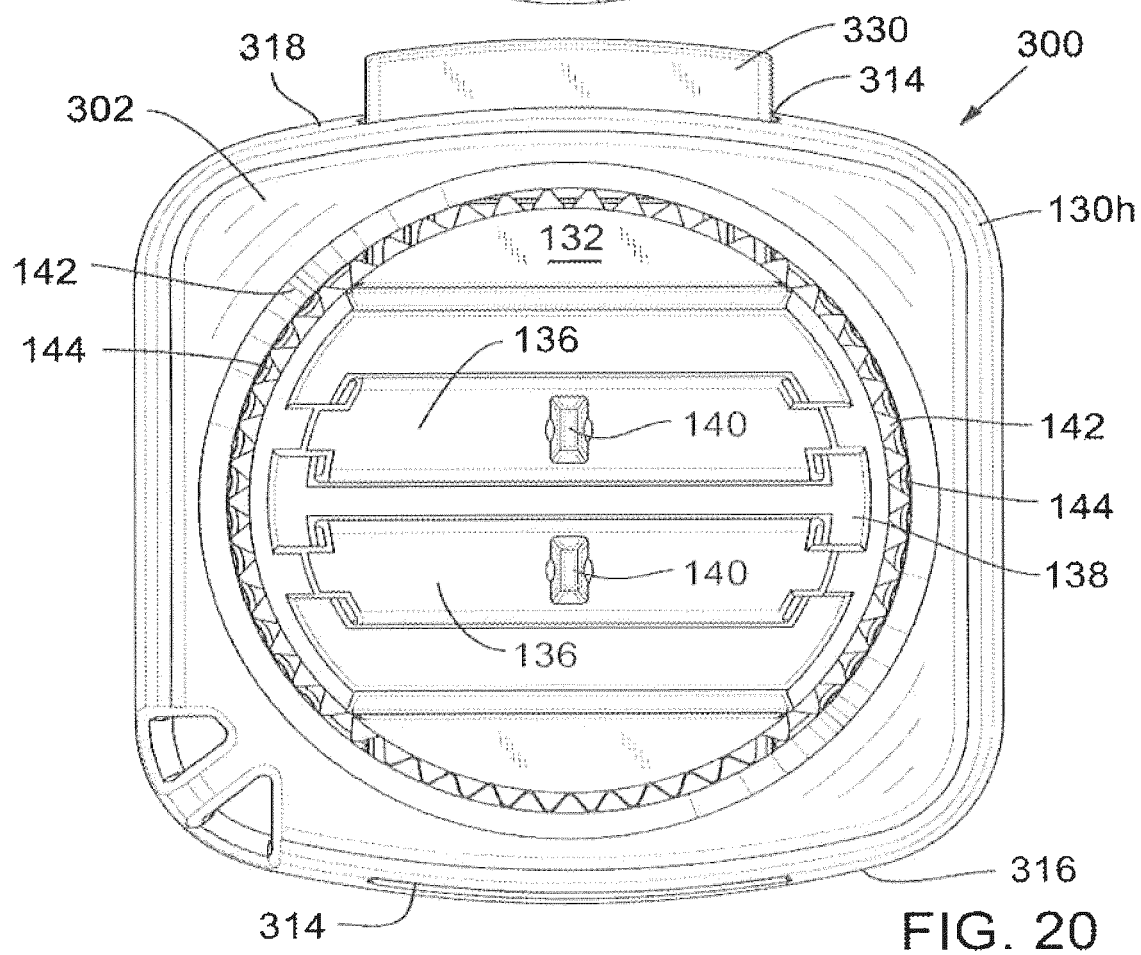
Figure 21:
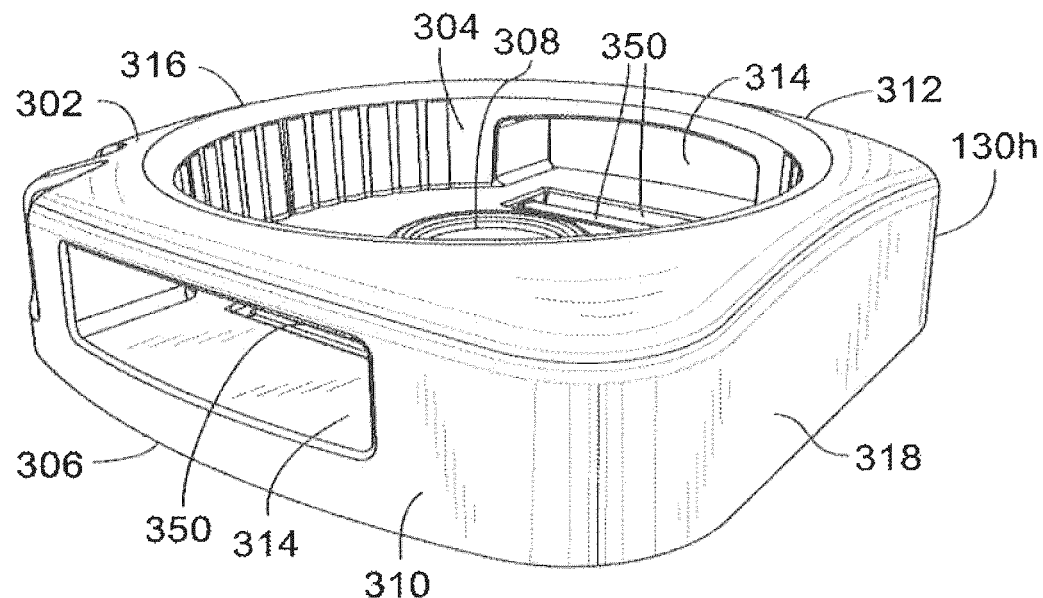
FIGS. 21 and 22 are, respectively, perspective and top plan views of the base mount of FIGS. 19 and 20.
Figure 22:
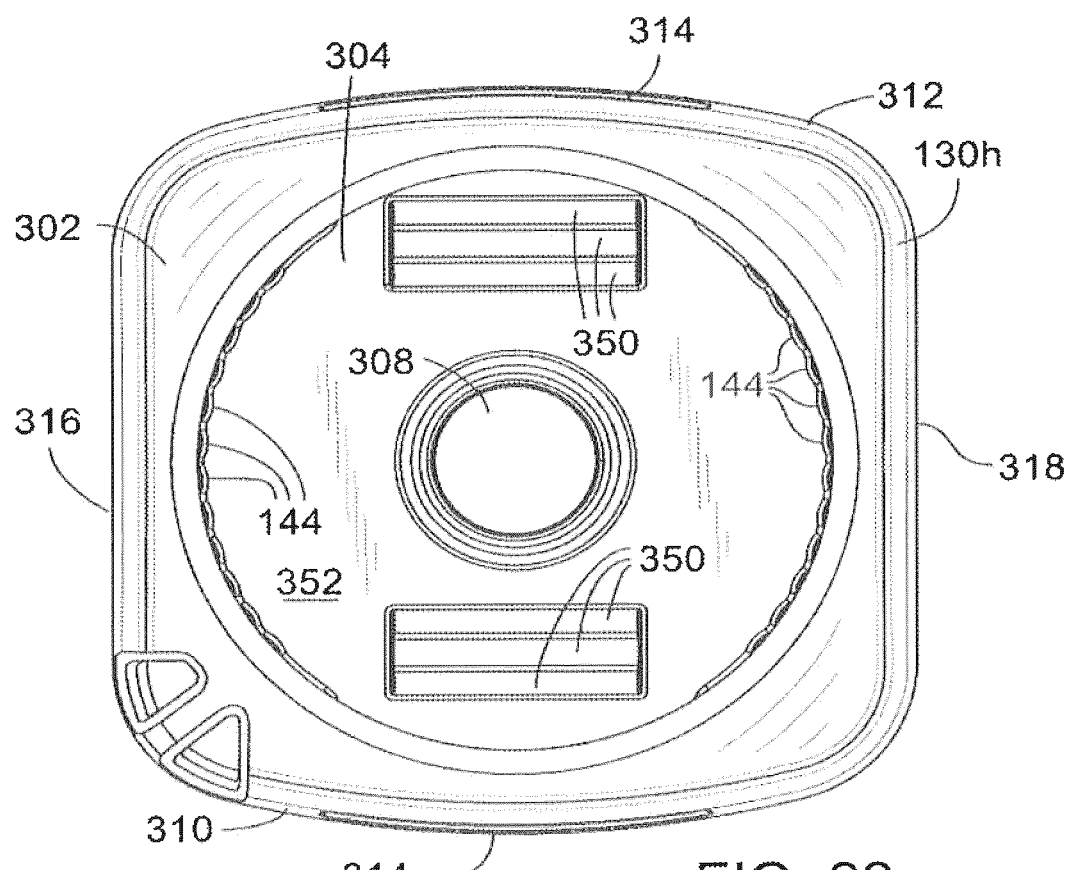

FIGS. 19 and 20 are, respectively, perspective and top plan views of a mounting system 300 that comprises rotatable circular rail plug 132 set in a base mount 130h configured with a locking feature that allows adjustment of digital video camera 10 when it is attached to a mounting surface. FIGS. 21 and 22 are, respectively, perspective and top plan views of base mount 130h. Base mount 130h is of generally rectangular shape and includes in its top wall 302 a large diameter circular opening 304 and in its bottom wall 306 a smaller diameter circular opening 308. Base mount 130h has opposite side walls 310 and 312 through which aligned, generally rectangular slots 314 of the same size are formed and opposite side walls 316 and 318 on the inner surfaces of which spatially aligned sawtooth-receiving edges 144 are formed. The inner surfaces of side walls 310, 312, 316, and 318 include arcuate segments that are sized to permit bidirectional ratcheted rotational motion of circular rail plug 132 when it is set through circular opening 304 in base mount 130h with sawtooth-receiving edges 144 in matable relationship with circumferential sawtoothed edge 142.

FIGS. 23A, 23B, 23C, 23D, and 23E are, respectively, perspective, top plan, end elevation, side elevation, and bottom plan views of a slidable locking member 330 of generally rectangular shape. Slidable locking member 330 is sized to fit within each slot 314 and slidably extend through and project outside either one of side walls 310 and 312 when inserted in both of slots 314 in base mount 130h. Locking member 330 is a unitary structure that includes a generally planar center portion 332 positioned between a locking end piece 334 and a nonlocking end piece 336. Center portion 332 constitutes a recessed area that is bounded by raised end pieces 334 and 336 and into which circular rail plug 132 is inserted when mounting system 300 is assembled. Center portion 332 includes an oblong hole 338 having opposite circular segments 340 separated by straight line segments 342. U-shaped slots 344 cut in center portion 332 on either side of oblong hole 338 provide downwardly depending the locking tabs 346. Locking tabs 346 are sized and configured to slide across and fit into corresponding grooves 350 in a floor 352 of base mount 130h. Locking end piece 334 has a serrated arcuate inner surface 354, and nonlocking end piece 336 has a smooth arcuate inner surface 356. The curvatures of arcuate inner surfaces 354 and 356 are complementary to the curvature of circular rail plug 132.

Figure 24:
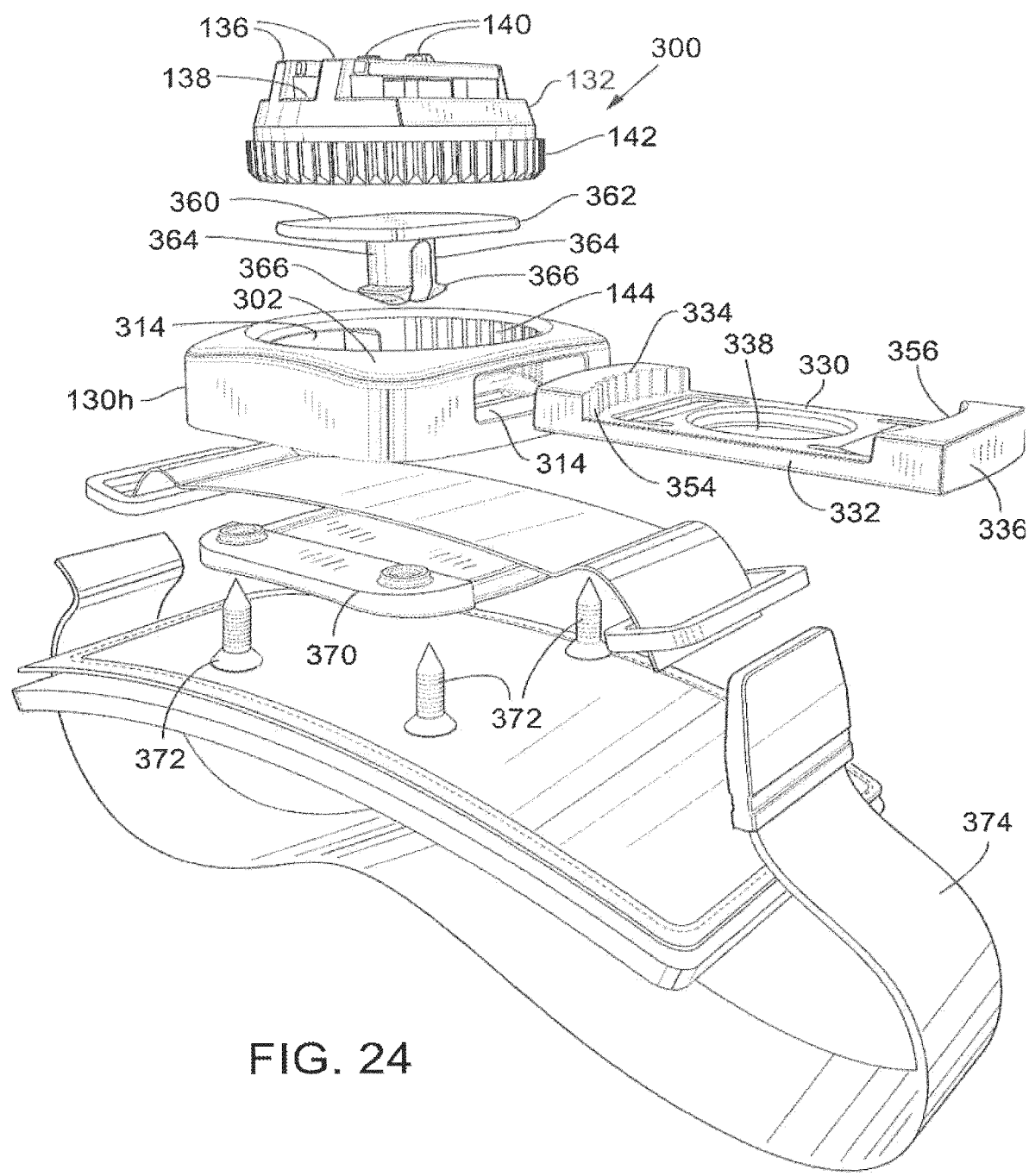
FIG. 24 is an exploded view of the mounting system of FIGS. 19 and 20, to which is attached an attaching mechanism.

FIG. 24 is an exploded view of mounting system 300 to which is attached an exemplary attaching mechanism. When mounting system 300 is assembled, locking member 330 is installed in base mount 130h with end pieces 334 and 336 fitted for sliding movement in slots 314. A plug 360 composed of a top disk 362 and two downwardly depending legs 364 secures locking member 330 to and limits its range of travel within slots 314 in base mount 130h. Top disk 362 fits in a recess in and thereby receives rail plug 132, and flanges 366 extending from the free ends of legs 364 secure plug 360 in base mount 130h when the free ends of legs 364 are pushed through circular opening 308.

Mounting system 300 operates in the following manner. A user adjusts the angular position of digital video camera 10, which is operatively connected to mounting rails 136, by rotating rail plug 132 within base mount 130h. To permit such rotation, the user pushes nonlocking end piece 336 to slide locking member 330 so that serrated inner surface 354 moves away from and does not engage sawtoothed edge 142 of rail plug 132. Legs 364 of plug 360 contact the boundary of oblong hole 338 and thereby stop the sliding motion of locking member 330 with its locking end piece 334 projecting outwardly from its associated slot 314. Locking tabs 346 fit in their corresponding grooves 350 to releasably hold locking member 330 in its unlocked position. Rotation of rail plug 132 provides audible, tactile feedback to the user because of the meshing relationship between sawtooth-receiving edges 144 and sawtoothed edge 142.

Upon completion of angular position adjustment of digital video camera 10, the user locks rail plug 132 in place by pushing locking end piece 334 to slide locking member 330 so that serrated inner surface 354 engages sawtoothed edge 142 of rail plug 132. The sliding motion of locking member 330 stops with its nonlocking end piece 336 projecting outwardly from its associated slot 314. Locking tabs 346 fit in their corresponding grooves to releasably hold locking member 330 in its locked position.

Base mount 130h can be directly mounted to a mounting surface with use of an adhesive. Base mount 130h also may be mated to a variety of mounting surfaces by adding a custom connecting plate, such as strap-connecting plate 370, with screws 372 or another technique such as adhesive bonding or welding. These connecting plates may alter the shape of base mount 130h to better connect to shaped surfaces or may include a variety of attaching mechanisms, such as, for example, a strap 374 or a hook.

With reference again to FIGS. 3B, 3E, 4B, and 5, button 64 (or an additional button 388) may control one or more status indicators such as LED 82 that indicates via light pipe 84 that digital video camera 10 is recording. Button 64 (or additional button 388) may, for example, also control operation of an LED 390 that indicates through a light pipe 392 the power status of a battery (not shown). In some embodiments, a single push controls two or more status indicators (or all of the status indicators, and may control laser sources 48 and a recording standby mode as well).

In some embodiments, the status indicators may provide a different color depending on the status of the item in question. In some embodiments, green, yellow, and red LEDs are used to indicate whether the battery is completely charged, half-charged, or nearly depleted. Similarly, in some embodiments, green, yellow, and red LEDs are used to indicate whether the SD memory card is nearly empty, half-empty, or nearly full. In other embodiments, green light indicates greater than or equal to 80% space or charge, yellow light indicates greater than or equal to 30% space or charge, and red light indicates less than 30% space or charge. Skilled persons will appreciate that the number and meaning of colors can be varied. Camera housing 22 may provide symbols indicating what items light pipes 84 and 392 designate, such as a battery symbol 394 and a memory card symbol 396 on back door 30.

To facilitate an easier and more manageable process for the video once it has been recorded, digital video camera 10 may be designed to automatically segment the video into computer and web-ready file sizes. The segment can be automatically determined by the hardware during the recording process without intervention by the user. In some embodiments, software will automatically close a video file and open a new file at predefined boundaries. In some embodiments, the boundaries will be time-based, for example, ten minutes for each segment, or size-based, for example 10 MB for each segment. Additionally, the segmentation process may be designed so that file boundaries are based on preset limits or so that the user can adjust the segment length to the user's own preferred time. In some embodiments, the video encoder (hardware or software based) will optimize the file boundary by delaying the boundary from the nominal boundary position until a period of time with relatively static video and audio, i.e., when there are minimal changes in motion. Skilled persons will appreciate, however, that in some embodiments, such segmentation may be implemented via software or hardware.

Digital video camera 10 is an all-in-one, shoot and store digital video camcorder and is designed to operate in extreme weather conditions and in a hands-free manner. Digital video camera 10 is wearable and designed for rugged environments (water, heat, cold, extreme vibrations), and the Contour 1080P™ system includes application mounts 126 to attach to any person, equipment, or vehicle. The internal components of digital video camera 10 may be silicon treated, coated, or otherwise insulated from the elements, keeping digital video camera 10 operational, no matter the mud, the dirt, the snow, and the rain.

Preferred embodiments of digital video camera 10 are equipped with wireless connection protocol and global navigation and location determination, preferably global positioning system (GPS), technology to provide remote image acquisition control and viewing. The Bluetooth® packet-based open wireless technology standard protocol is used to provide control signals or stream data to digital video camera 10 and to access image content stored on or streaming from digital video camera 10. The GPS technology enables tracking of the location of digital video camera 10 as it records image information. The following describes in detail the implementation of the Bluetooth® protocol and GPS technology in digital video camera 10.

Preferred embodiments of digital video camera 10 permit the mounting of camera housing 22 upside down while retaining the proper orientation of the video images by mechanical or electrical 180° rotation of lens 26. The mechanical rotation is shown in FIGS. 25A, 25B, 25C, 250, and 25E. FIGS. 25A, 25B, 25C, and 25D are front perspective views of digital video camera 10 showing lens 26 set in a vertical position, with camera housing 22 of digital video camera 10 rotated 90° counter-clockwise, not rotated, rotated 90° clockwise, and rotated 180° to an inverted position, respectively, relative to the vertical position. FIG. 25E is a front elevation view of digital video camera 10 in the orientation of FIG. 25B annotated with dimension lines indicating 185° counter-clockwise and 95° clockwise ranges of angular displacement of horizontal image plane 16 achievable by manual rotation of rotary controller 14. The orientation may be flipped prior to signal processing by simply altering the pixel selection or can be flipped during signal processing by simply altering the interpretation of the pixels. The orientation can be automatically controlled by sensing the orientation of camera housing 22 using a variety of sensors and altering the pixels based on these data.

Figure 27A:
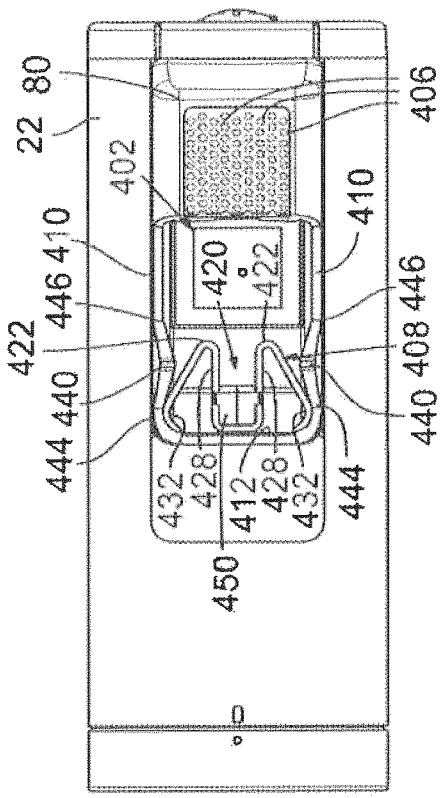
FIGS. 27A and 27B are, respectively, front perspective and top plan views of the digital video camera of FIGS. 4A and 4B with its slidable switch activator in a recording OFF slide setting position.
Figure 27B:
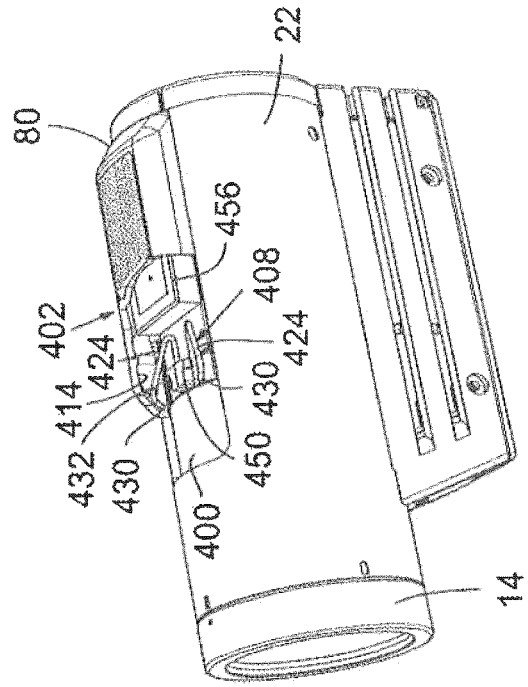
Figure 26A:
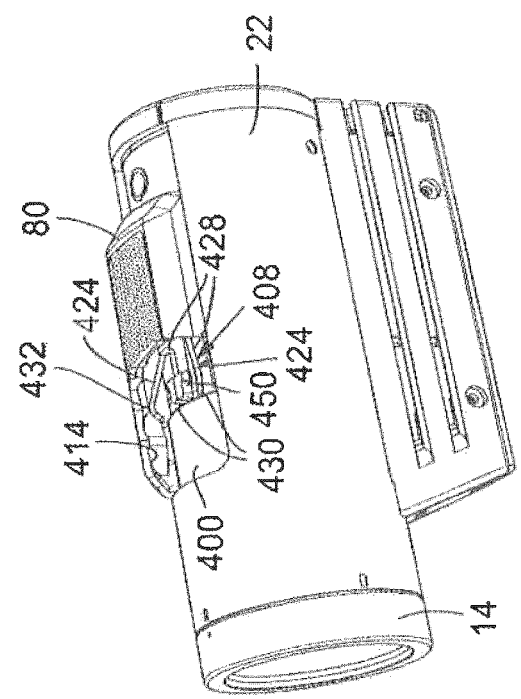
FIGS. 26A and 26B are, respectively, front perspective and top plan views of the digital video camera of FIGS. 4A and 4B with its slidable switch activator in a recording ON slide setting position.
Figure 26B:
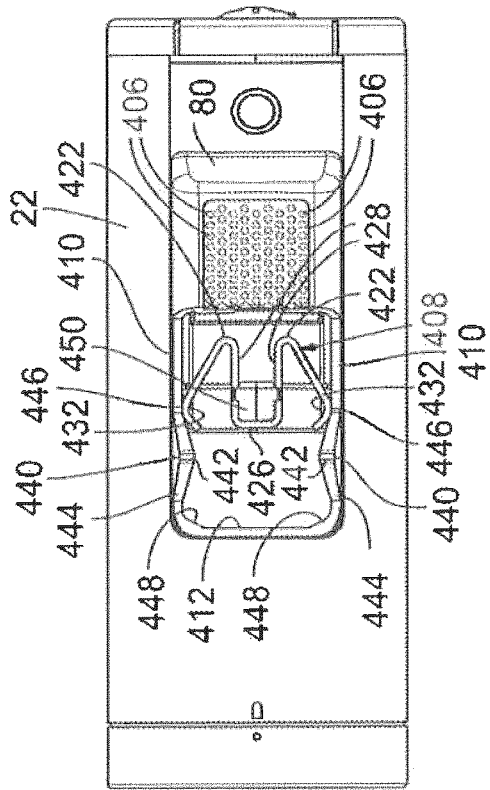

FIGS. 26A and 26B, FIGS. 27A and 27B, FIG. 28, and FIGS. 29A and 29B show the configuration of digital video camera 10 in which Bluetooth® wireless protocol and GPS technology are implemented to enable remote image acquisition control and viewing. FIGS. 26A and 27A are front perspective views of digital video camera 10 with slidable switch activator 80 in its respective recording ON and recording OFF slide setting positions; and FIGS. 26B and 27B are top plan views of the digital video camera 10 with slidable switch activator 80 in its respective recording ON and recording OFF slide setting positions. A portion of switch activator 80 is broken away in these drawing figures to reveal the placement of certain internal component parts described in greater detail below.

Figure 28:
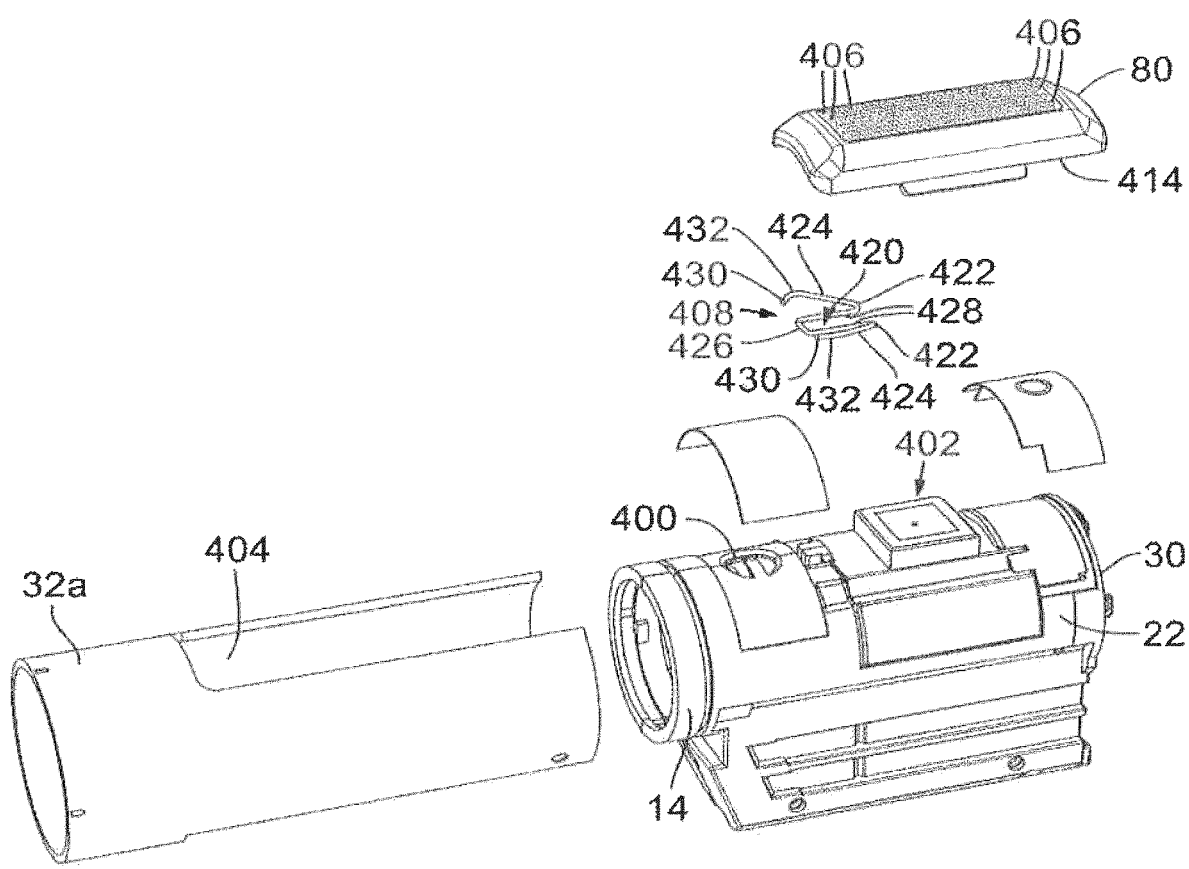
FIG. 28 is a partly exploded view of the digital video camera of FIGS. 26A, 26B, 27A, and 27B.

FIG. 28 is a partly exploded view of digital video camera 10, showing the placement and mounting arrangement of component parts implementing Bluetooth® wireless protocol and GPS receiver technology in main housing 100 shown in FIGS. 5 and 6. A Bluetooth® wireless module 400 is installed in main housing 100 at a location proximal to rotary controller 14. A GPS assembly 402 is installed in main housing 100 at a location proximal to back door 30 of camera housing 28. Optical support barrel 32a having an open ended slot 404 fits over main housing 100 in an orientation such that Bluetooth® wireless module 400 and the upper end of GPS assembly 402 fit and are thereby exposed within slot 404. Switch activator 80 provided with a two-dimensional array of circular openings 406 fits over and slides within slot 404 between the recording ON slide setting position shown in FIGS. 26A and 26B and the recording OFF slide setting position shown in FIGS. 27A and 27B. Openings 406 provide an audible sound passageway to facilitate pickup by microphone 90 of spoken words or other sound effects.

Common implementations for sliding switches that have long travel entail use of a magnet to pull and hold the switch in its final position or use of a switch mechanism continuously pressed by the user over the full travel distance and provided with a holding mechanism in place in the ON and OFF positions. Digital video camera 10 is equipped with a slide switch mechanism that solves the problems associated with long travel distance. A scissor spring 408 assists in actuating slidable switch activator 80 over the long travel range between the recording ON and OFF slide setting positions.

FIGS. 26B, 27B, and 28 show a preferred shape of scissor spring 408 and the manner in which it cooperates with the geometric features of inner side wall surfaces 410 and an inner end wall surface 412 formed in an underside cavity 414 of switch activator 80. Scissor spring 408 is a one-piece wire member including multiple bends that form a U-shaped center portion 420 having rounded distal ends 422 from each of which a leg portion 424 upwardly extends back toward center portion 420. U-shaped center portion 420 includes a base member 426 and two generally parallel side members 428 that terminate in rounded distal ends 422. Upwardly extending leg portions 424 diverge generally outwardly away from side members 428 and terminate in ends 430 that are inwardly bent toward side members 428 and do not extend beyond center portion 420. A curved section 432 in each leg portion 424 forms its inwardly directed bend and provides a bearing surface that contacts an inner side wall surface 410 of switch activator 80.

FIGS. 26A, 26B, 27A, and 27B show the geometric features in inner side wall surfaces 410 and inner end wall surface 412 of switch activator 80. Each side wall surface 410 includes an inwardly directed beveled portion 440 having an apex 442 and a proximal end 444 and a distal end 446 located respectively nearer to and farther from end wall surface 412.

Installation of scissor spring 408 in main housing 100 entails placement of U-shaped center portion 420 with its base member 426 and side members 428 against a raised block 450 on a top surface 452 of a printed circuit board (PCB) 454 of GPS assembly 402. The length of base member 426 is chosen to establish a snug fit of raised block 450 within U-shaped center portion 420 to keep scissor spring 408 stationary during sliding motion of switch activator 80. As shown in FIGS. 26A and 26B, whenever switch activator 80 is in the recording ON slide setting position, curved sections 432 of scissor spring leg portions 424 rest in shallow notches formed at distal ends 446 of beveled portions 440. As shown in FIGS. 27A and 27B, whenever a user slides switch activator 80 from the recording ON slide setting position to the recording OFF slide setting position, curved sections 432 exit the shallow notches at distal ends 446, slide along entire lengths of beveled portions 440, and come to rest at shallow notches formed at proximal ends 444 of beveled portions 440. Curved sections 432 of leg portions 424 are of complementary shape to curved sections 448 of inner end wall surface 412.

The shaping of scissor spring 408 imparts resistance to prevent the initial sliding motion of switch activator 80 in either direction, but in response to user applied pressure overcoming the resistance, switch activator 80 automatically travels to the stopping position without effort by the user. Scissor spring 408 exerts passive resistance to any motion and therefore holds switch activator 80 in the proper position until the user again moves switch activator 80. The shape of scissor spring 408 can be varied based upon, for example, the geometry of switch activator 80, the length of travel, and desired holding force.

The above-described spring solution is uniquely resistant to vibration and is well-suited for a high vibration environment. Scissor spring 408 is an improvement over magnetic sliding switch movements because the former does not introduce magnetic interference that may affect other functions in digital video camera 10. Scissor spring 408 is also an improvement over a double detent implementation because the user is confident switch activator 80 is in the proper position. This spring solution could be expanded to include a combination of springs to provide specialized motion or specific force profiles. This spring design can also control linear or circular motion.

Figure 29A:
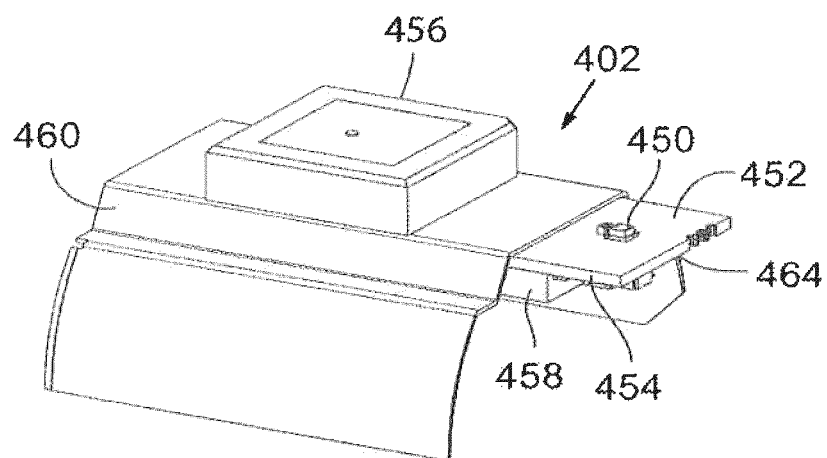
FIGS. 29A and 29B show, respectively, perspective and exploded views of a GPS assembly that includes a GPS patch antenna and GPS receiver module to provide GPS functionality in the digital video camera of FIGS. 26A, 26B, 27A, and 27B.
Figure 29B:
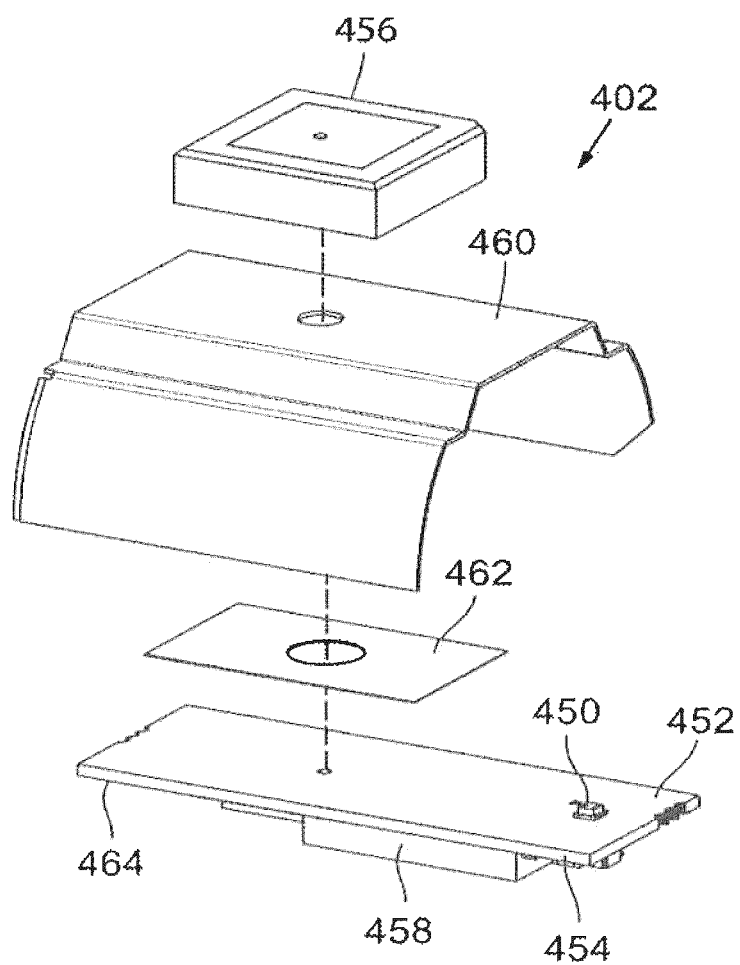

FIGS. 29A and 29B show respective perspective and exploded views of GPS assembly 402 separate from main housing 100, in which GPS assembly 402 is installed for operation in digital video camera 10. GPS assembly 402 includes a GPS passive patch antenna 456 and a GPS receiver module 458 to provide GPS functionality to digital video camera 10. A GPS ground plane 460 in the form of a stepped, generally U-shaped aluminum shroud is positioned between patch antenna 456 and GPS printed circuit board 454 and affixed to top surface 452 of the latter by GPS ground plane mounting tape 462. GPS receiver module 458 is mounted to GPS printed circuit board 454 on its bottom surface 464. A preferred GPS patch antenna 456 is a Model PA1575MZ50K4G-XX-21, which is a high gain, customizable antenna available from INPAQ Technology Co., Ltd., Taiwan. GPS patch antenna 456 is custom tuned to its peak frequency to account for detuning effects of the edges of optical support barrel 32a. A preferred GPS receiver module 458 is a Model NEO-6 module available from u-blox AG, Switzerland.

FIGS. 29A and 29B show that GPS ground plane 460 is physically shaped to complement or mirror the curved shape of optical support barrel 32a of housing 22 so that the ground plane area can be maximized as the shape of the ground plane conforms to, i.e., without altering, the shape of camera housing 22. Additionally, GPS patch antenna 456 is supported by its own internal ground plane, which is arranged such that it overlaps the inside of the existing aluminum case. This overlap allows RF currents to pass between the aluminum case and GPS ground plane 460 through capacitive coupling and hence have the effect of increasing the size of the overall ground plane area. This increased ground plane area further improves the GPS reception. Moreover, GPS patch antenna 456 is tuned with these components coupled for optimal reception by the overall system. The ground plane customization and electrical coupling to camera housing 22 or other metal components of digital video camera 10 improve performance by achieving higher antenna gain and consequent enhanced signal reception when digital video camera 10 is mounted in multiple positions.

When recording video or taking photographs in a sports application, digital video camera 10 is often mounted in a location that does not permit the user to easily see the camera. Implementing digital video camera 10 with a wireless connection protocol enables remote control of the operation of and remote access to image data stored in digital video camera 10. In preferred embodiments, the integration of Bluetooth® wireless technology in the wearable digital video camera 10 facilitates implementation of several features, including remote control, frame optimization, multi-camera synchronization, remote file access, remote viewing, data acquisition (in combination with GPS capability), and multi-data sources access (in combination with GPS capability).

Implementing Bluetooth® wireless technology in digital video camera 10 enables the user to control it remotely using a telephone, computer, or dedicated controller. This allows digital video camera 10 to remain sleek, with few buttons and no screen. Additionally, a lack of need for access to a screen or controls provides more flexibility in mounting digital video camera 10.

The remote control device (i.e., telephone, computer, dedicated viewer, or other Bluetooth®-enabled device) can access files stored on digital video camera 10 to allow the user to review the content in such files and manage them on the camera. Such access can include file transfer or file playback in the case of video or audio content.

Using a wireless signal transfer, the remote device can access data streaming from digital video camera 10. Such data can include camera status, video, audio, or other data (e.g., GPS data) collected. Standard video can exceed the bandwidth of a Bluetooth® connection. To resolve any quality of service issues, a fast photo mode is used to simulate video. In this case, photographs are taken in succession, then streamed and displayed in sequence to simulate video playback. Firmware in a main processor captures and streams the photographs, and the receiving application is designed to display photographs in quick succession. To be space efficient, the photographs may be stored in a FIFO buffer so that only limited playback is available.

Alternative implementations of a remote viewer include one or more of reduced resolution or frame rate, file sectioning, frame sampling, and Wi-Fi to media server. Reduced resolution or frame rate entails recording video in two formats, high quality and low quality, in which the lower quality file is streamed or played back after the recorded action has taken place. For streaming implementation, wireless connection bandwidth can be monitored to adapt to the available bandwidth the resolution, bit rate, and frame rate on the secondary recording. Additionally, buffering can be used in conjunction with adaptive bit rate control. File sectioning entails breaking a recording into small files and transferring each file upon completion to allow for viewing via a wireless device in near real time. File transfer may be delayed so as to limit interruptions that result from bandwidth limitations. Frame sampling entails real time video frame sampling (e.g., video compression intraframes (I-frames) only). Wi-Fi to media server entails use of Wi-Fi to establish the camera as a media server on selected networks, allowing other devices to read and play content accessed from the device.

Figure 30:
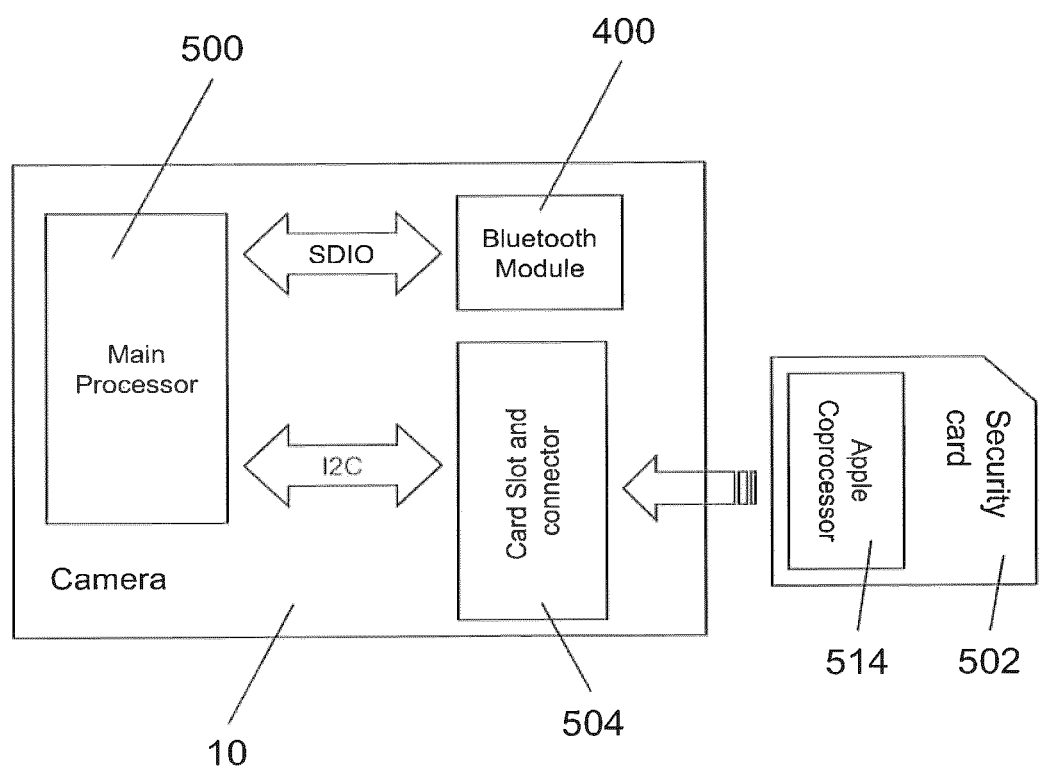
FIG. 30 is a simplified block diagram showing a preferred implementation of wireless technology in the digital video camera of FIGS. 26A, 26B, 27A, and 27B.

FIG. 30 is a simplified block diagram showing a preferred implementation of wireless technology in digital video camera 10. FIG. 30 shows digital video camera 10 with built-in Bluetooth® wireless module 400 that responds to a Contour Connect Mobile App application software executing on an operating system for mobile devices such as smartphones and tablet computers to enable such a mobile device to become a wireless handheld viewfinder. A Contour Connect Mobile App that is compatible for use with an iOS mobile operating system of Apple®, Inc. is available on the iPhone App Store and that is compatible for use on an Android mobile operating system of Google Inc. is available on the Android Market. The firmware of a main processor 500 stores an updated version of compatible software to respond to the Contour Connect Mobile App executing on a mobile device. This wireless connection capability enables a user to configure camera settings in real time and preview what digital video camera 10 sees. Specifically, a user can check the camera angle on the wireless device screen and without guesswork align the camera shot and adjust video, light level, and audio settings before beginning the activity he or she wants to record.

The functionality permitted across industry standard interfaces is often limited by the receiving or transmitting device based on its permissions. This means that one device may refuse to permit certain functionality if the other device does not have proper certificates or authentications. For example, the Apple® iPhone and similar products require certain security authentication on data signals transmitted using the Bluetooth® interface. The security requirements on such interfaces vary by product and the manufacturer. Oftentimes the same product is intended to connect with a variety of devices, and it is not desirable to integrate the security component for all possible features or external devices.

In preferred embodiments, the signal path is designed such that the presence of this security integrated circuit is not required for full functionality for such other devices. However, by including a connector in this signal path, a security module can be added by the user after manufacturing to allow connection with such controlled devices. By including such a connector in the signal path, the relevant signal security module may be provided separately for only those applications that require such security authentication. Additionally, in preferred embodiments, the Apple® security card is packaged separately as a self-contained card. The circuit is designed to retain the authentication integrity but to interface with the controlling device through a standard connector. FIG. 30 also shows placement of a Contour Connect View (security) Card 502 in a card slot and connector 504 of digital video camera 10 to enable connection with a supported Apple® iOS device. A Contour Connect View Card is available from Contour, Inc., the assignee of this patent application.

Figure 31:
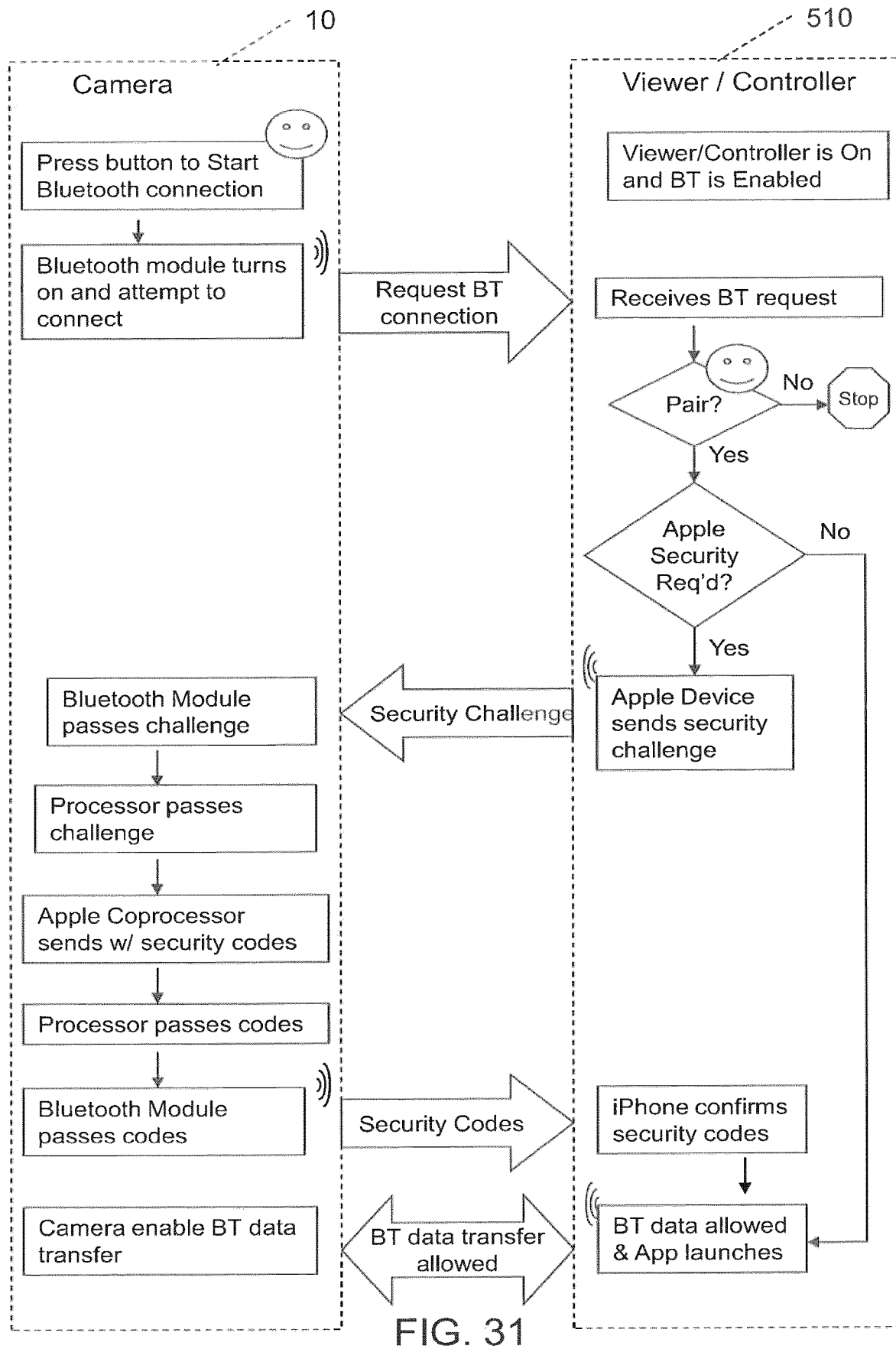
FIG. 31 is a flow diagram showing the pairing of two devices by Bluetooth® wireless connection.

FIG. 31 is a flow diagram showing the pairing of two devices by Bluetooth® wireless connection. Main processor 500 of digital video camera 10 stores a data file identifying a Bluetooth®-enabled viewer/controller device 510. (An appearance of a smiley face icon in the flow diagrams indicates action by or display of status information to a user.) A user presses a wireless connection activator button (preferably located near switch activator 80 but not shown in the drawings) on camera housing 22 to turn on Bluetooth® module 400, which transmits a Bluetooth® ("BT") Connection Request signal to Bluetooth® connection-enabled viewer/controller 510. Viewer/controller 510 receives the Bluetooth® Connection Request signal, determines whether there is a Bluetooth® ID connection match pair, and upon recognition of a match pair, determines whether viewer/controller 510 is iOS or Android implemented. If it is Android implemented and therefore Apple® security is not required, viewer/controller 510 allows and launches the Contour Connect Mobile App to perform Bluetooth® data transfer to and from digital video camera 10. If it is iOS implemented and Apple® security is required, viewer/controller 510 sends a Security Challenge signal for passage through Bluetooth® module 400 and main processor 500 to an Apple® coprocessor 514 mounted on Apple® security card 502. Apple® coprocessor 514 sends security codes for passage through main processor 500 and Bluetooth® module 400 to viewer/controller 510, which confirms the security codes and allows and launches the Contour Connect Mobile App to perform Bluetooth® data transfer to and from digital video camera 10.

Figure 32:
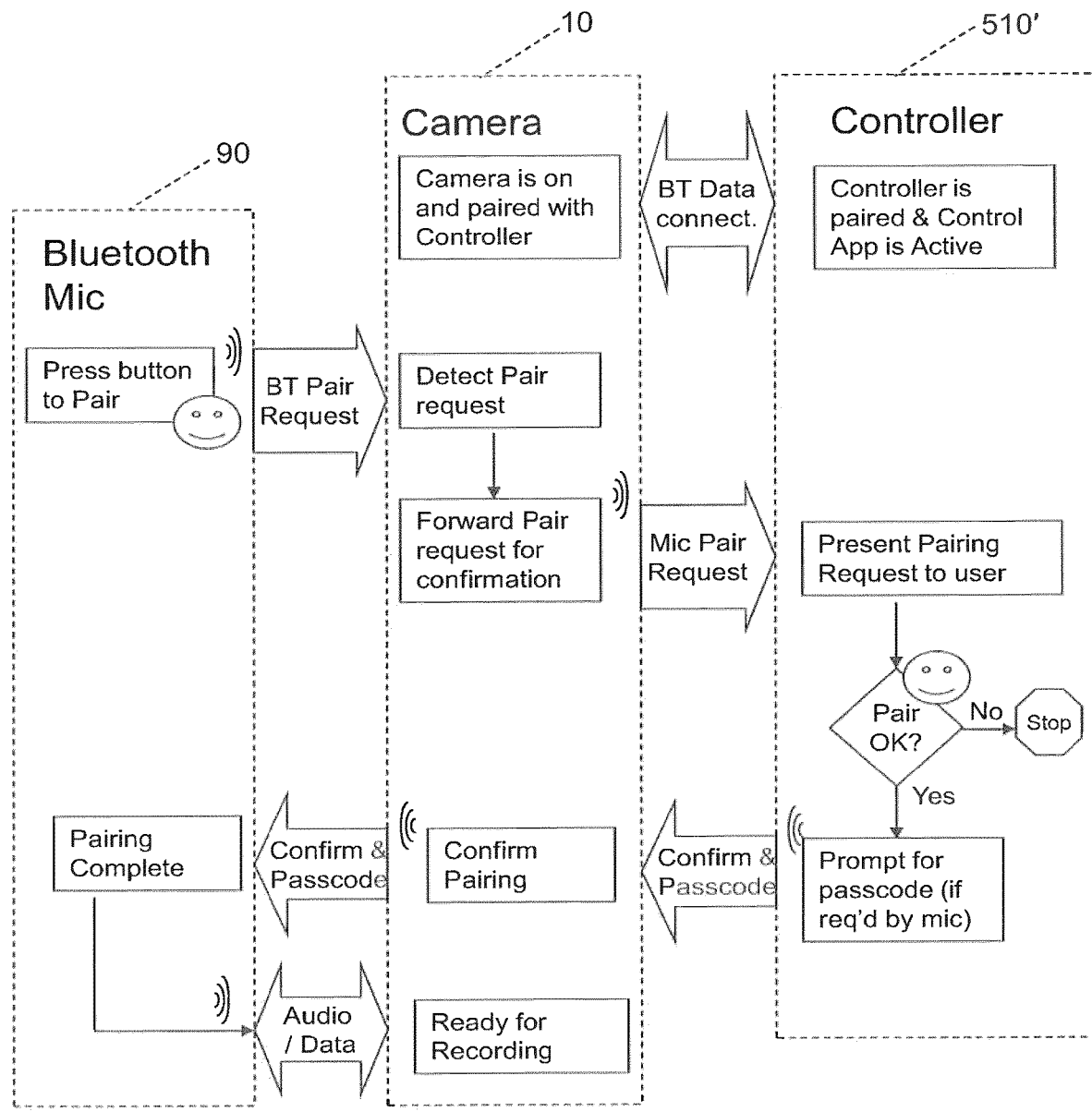
FIG. 32 is a flow diagram showing an example of pairing a Bluetooth®-enabled microphone and the digital video camera of FIGS. 26A, 26B, 27A, and 27B.

The use of a data file to identify the Bluetooth® ID of a device allows two devices to pair when neither device has a display screen. FIG. 32 is a flow diagram showing an example of pairing Bluetooth® microphone 90 and digital video camera 10, neither of which has a display screen. Digital video camera 10 and a controller 510' are initially paired by Bluetooth® wireless data connection, and the Contour Connect Mobile App is active, as described above with reference to FIG. 31. Viewer/controller 510 and controller 510' are of similar construction, except that the latter has no display screen. A user slides switch activator 80 to its ON position to supply power to microphone 90 and transmit a Pair Request signal to digital video camera 10, which detects and forwards to controller 510' a Microphone Pair Request signal for confirmation. The user responds to the pairing request by manipulating an actuator associated with controller 510'. If user actuation indicates refusal of the pairing request, controller 510' concludes the pairing process. If user actuation indicates acceptance of the pairing request, controller 510' transmits to digital video camera 10 a Confirmation signal, together with a passcode if one is required by microphone 90. Upon receipt of the Confirmation signal, digital video camera 10 transmits a Confirmation signal and any passcode to microphone 90 and thereby completes the pairing by initiating audio data capture and recording by the audio encoder in digital video camera 10.

Figure 33:
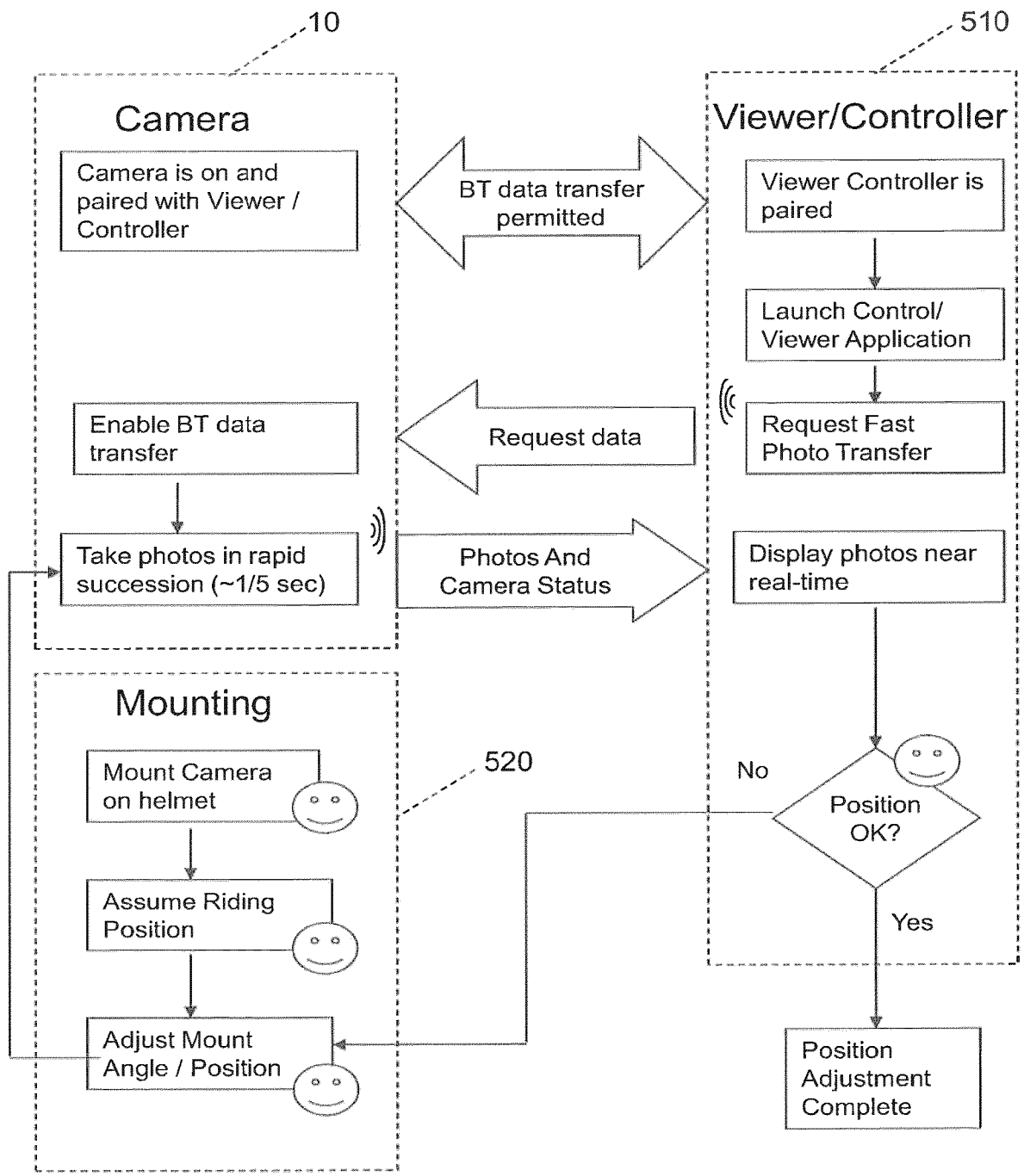
FIG. 33 is a flow diagram showing a preferred camera mounting position adjustment procedure carried out by a helmet-wearing user to align a helmet-mounted digital video camera of FIGS. 26A, 26B, 27A, and 27B.

FIG. 33 is a flow diagram showing a preferred camera position adjustment procedure carried out by a helmet-wearing user, such as a bicycle or snowboard rider or skier, to align digital video camera 10 mounted on the user's helmet. Digital video camera 10 and viewer/controller 510 are initially paired by Bluetooth® wireless data connection, and the Contour Connect Mobile App is active, as described above with reference to FIG. 31. A launch control/viewer application instruction causes transmission of a fast photo transfer Data Request signal to Bluetooth® data transfer-enabled digital video camera 10, which responds by enabling the taking of photographs in rapid succession (e.g., five photographs each second) of the scene to which camera lens 26 is pointed. A mounting activity sequence 520 indicated in FIG. 33 represents user activity of mounting digital video camera 10 on the helmet, assuming a riding position, and adjusting the position and angle of digital video camera 10 by selecting its mounting surface location on the helmet and rotating rail plug 132 within base mount 130*h* of mounting system 300. The angle/position mounting adjustment performed by the user causes the taking of photographs of the scene in rapid succession and transmitting them for near real-time display to the user observing the display screen of viewer/controller 510. Successive iterations of angle/position mounting adjustment, picture taking in rapid succession, and user observation of the displayed scene continue until the user is satisfied with the position of the scene displayed, whereupon the mounting position adjustment of digital video camera 10 on the helmet is complete.

Frame optimization can be accomplished with a remote control device or within digital video camera 10, if it is equipped with a screen and controls. Frame optimization may entail one or both of lighting and color optimization and frame alignment, either manually or automatically.

Figure 34:
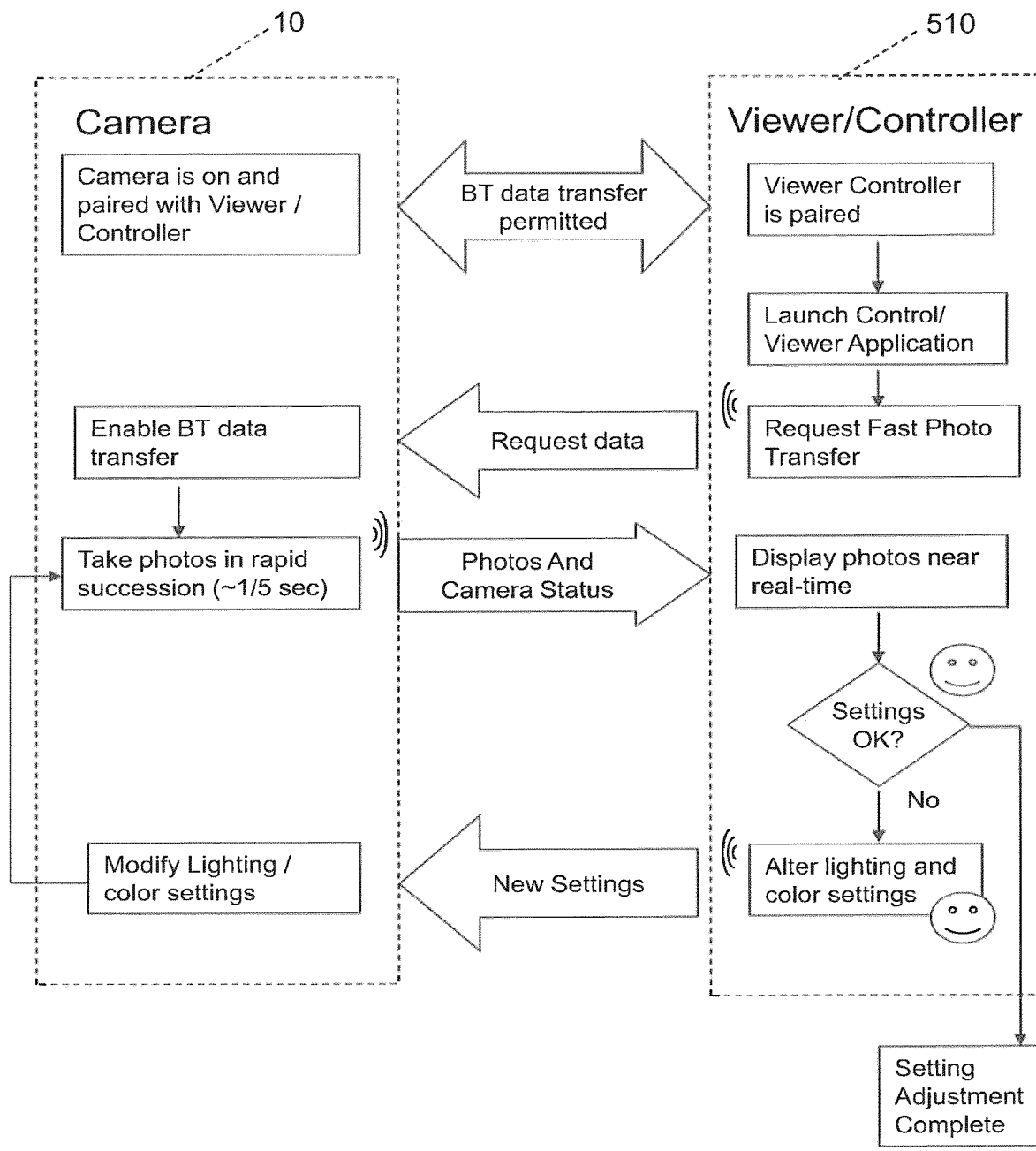
FIG. 34 is a flow diagram showing a preferred manual lighting level and color settings adjustment procedure carried out by a user upon completion of the camera mounting position adjustment procedure of FIG. 33.

FIG. 34 is a flow diagram showing a preferred manual lighting level and color settings adjustment procedure followed by the user after completing the mounting position adjustment described above with reference to FIG. 33. The manual lighting level and color setting procedure shown in FIG. 34 differs from the mounting position adjustment procedure of FIG. 33 in that 1) mounting activity sequence 520 does not apply, 2) a settings OK decision block replaces the Position OK decision block in viewer/controller 510, and 3) the manual angle/position mounting adjustment causing the taking of photographs of the scene in rapid succession is replaced by transmission of a new settings instruction produced in response to user-manipulation of an alter lighting level and color settings actuator associated with viewer/controller 510. The manual lighting level and color adjustment procedure entails the user observing the successive photographs on the display screen and manipulating the alter lighting level and color settings actuator associated with viewer/controller 510 until the user is satisfied with the lighting level and color displayed, whereupon the manual setting adjustment is complete.

Figure 35:
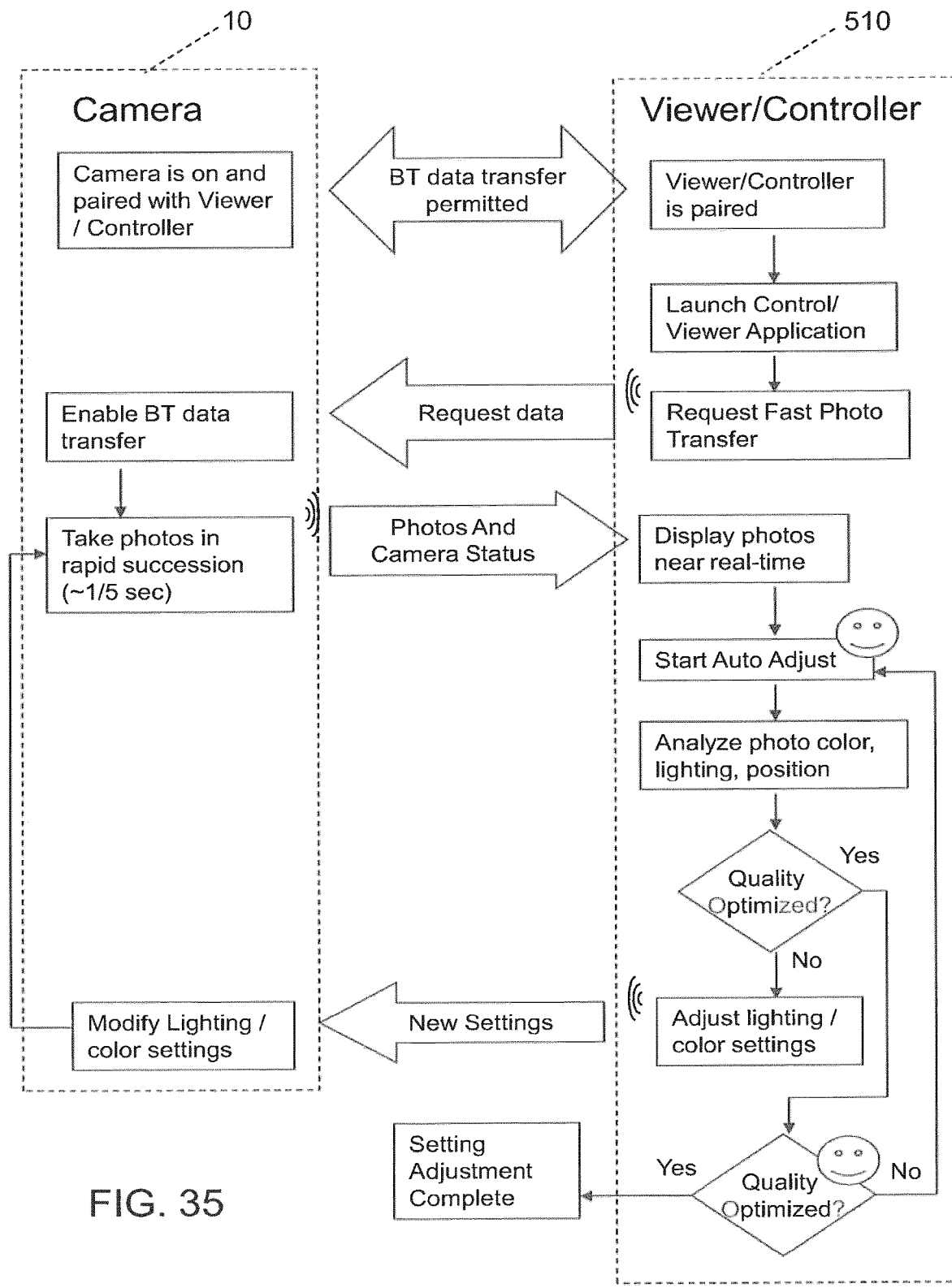
FIG. 35 is a flow diagram showing a preferred automatic lighting level and color settings adjustment procedure carried out by a user after completing the camera mounting position adjustment of FIG. 33.

Automatic lighting and color optimization uses video or photographic analysis in controlling the device. FIG. 35 is a flow diagram showing a preferred automatic lighting level and color settings adjustment procedure followed by the user after completing the mounting position adjustment described above with reference to FIG. 33. The automatic lighting level and color settings procedure shown in FIG. 35 differs from the manual lighting level and color settings procedure shown in FIG. 34 in that an Auto Adjust iterative loop replaces the Settings OK decision block of FIG. 33. Specifically, a Start Auto Adjust process block initiates an iterative Auto Adjust loop of programmed analysis of photograph color, lighting level, and position followed by a Quality Optimization decision query based on a set of programmed quality standards. The Auto Adjust loop iteratively performs the analysis and causes transmission of a new settings instruction to digital video camera 10 to take additional photographs for display and analysis by viewer/controller 510. The automatic lighting level and color adjustment procedure entails the automatic internal analysis of the photographs on the display screen and preprogrammed automatic adjustment of the lighting level and color settings until the Quality Optimized decision block indicates that image quality meets preprogrammed optimum quality standards and the final Quality Optimized decision block indicates that the user is satisfied by user manipulation of an actuator indicating the automatic setting adjustment is complete. Viewer/controller 510 can implement tuning algorithms to analyze frames, adjust settings, and reanalyze the frames to optimize lighting level and color settings. Small and fine alignment adjustments can be made automatically by altering the pixels used to define the frame. These adjustments can be made by redefining the center pixel or by redefining the bounding box. These adjustments can be horizontal, vertical, and rotational, including rotating a full 180° to allow for digital video camera 10 to be positioned upside down, as shown in FIG. 25D. For more precise optimization, digital video camera 10 may be pointed at a predefined chart to allow the automatic adjustments to achieve more precise and consistent settings.

Use of the many-to-many nature of Bluetooth® wireless technology enables a user to control multiple cameras. Multi-camera control allows for the controller to coordinate the lighting level and color settings on all cameras, provide guides for alignment of camera positions, and synchronize the videos on multiple cameras with synchronous start/stop or synchronous "alignment" on-screen display (OSD) frames or audio sound that can be embedded in the video to facilitate editing and post-processing. Use of wireless connection allows one camera to provide a synchronization signal to another camera so that videos can be synchronized in post-processing. The OSD frames may be stored in advance in the memory of digital video camera 10 and be simply triggered by a frame sync pulse to limit transmission bandwidth requirements and any associated errors or delays. This synchronization may include information such as, for example, video file name and camera identity of the primary camera. To improve accuracy of synchronization timing, the wireless transfer rate can be calibrated by pinging a secondary device and listening for response. To further improve accuracy, this ping/response cycle is repeated multiple times.

Figure 36:
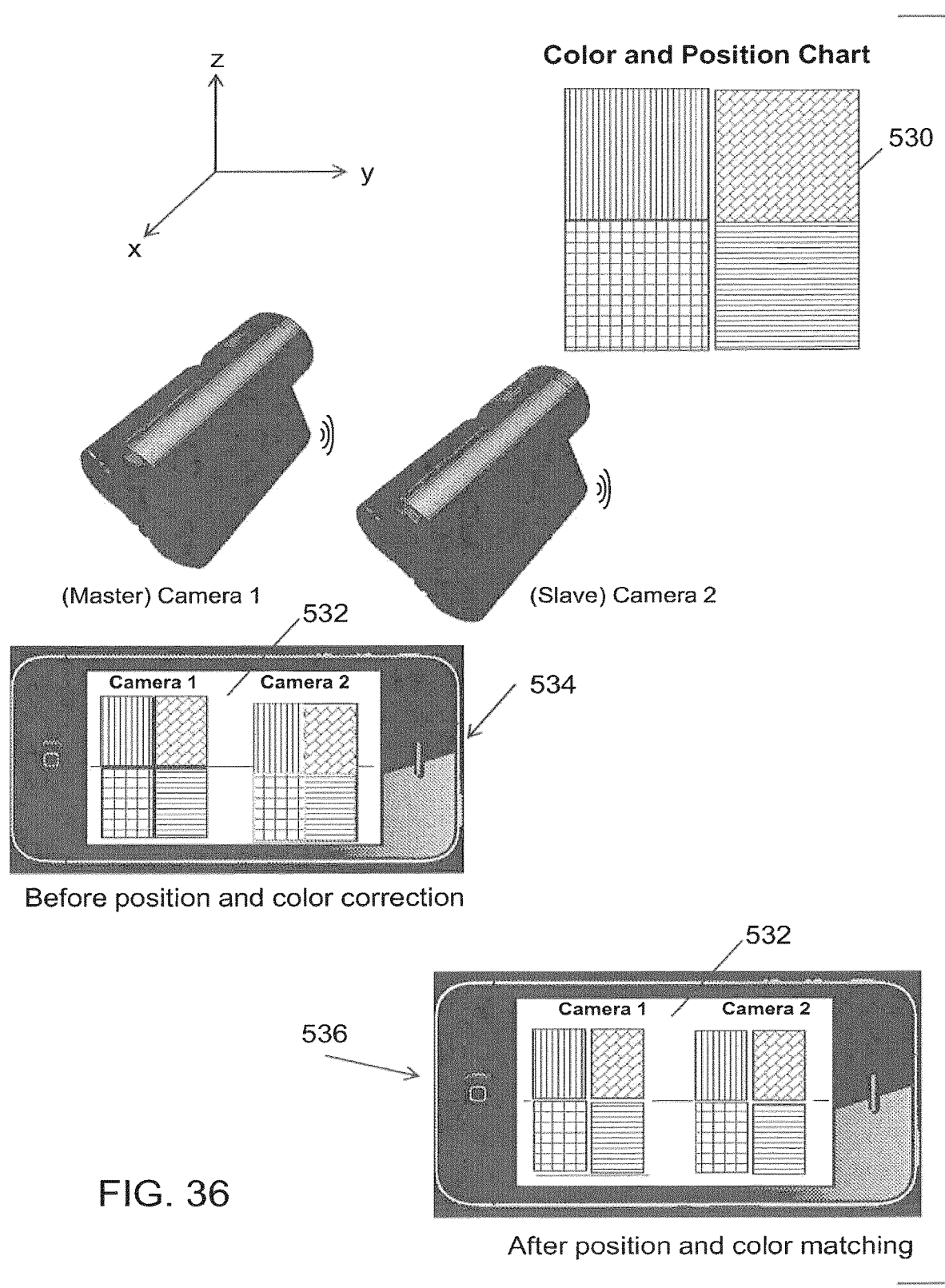
FIG. 36 shows two of the digital video cameras of FIGS. 26A, 26B, 27A, and 27B aimed at a common color chart.

A separate remote device can be used to pair two cameras in which neither camera has a screen. FIG. 36 shows a (Master) Camera 1 and a (Slave) Camera 2 of the same type as digital video camera 10 aimed at a common chart 530. The relative camera mounting can be adjusted to align the images in the Z-axis. The lighting level and color settings can be adjusted so that they are matched. Aligning the images and adjusting lighting level and color settings eliminate a need for post-processing when combining videos from multiple cameras at multiple angles or three-dimensional views. FIG. 36 shows an iPhone paired to Cameras 1 and 2 implemented with remote Start/Stop capability, which is described below. Master Camera 1 sends an OSD frame sync pulse to Slave Camera 2. Master Camera 1 analyzes photographs from Slave Camera 2 and adjusts settings to match the alignment and settings of Master Camera 1.

FIG. 36 presents two illustrations of a display screen 532 of viewer/controller 510 of an iPhone type showing for user observation side-by-side images produced by Cameras 1 and 2 viewing chart 530. Upper illustration 534 and lower illustration 536 show the comparative relationship between the position and color matching, respectively, before and after correction. Illustration 534 shows Z-axis misalignment of the two camera images and color imbalance, and illustration 536 shows post-correction image position alignment and color matching.

By controlling multiple cameras, the user is able to coordinate shots from different angles and ensure the color and lighting settings are similar to allow for seamless switching in playback. The preferred embodiments could be expanded so that in the event there were multiple devices daisy-chained together, they could use a single authentication. For example, if there were two cameras that were connected via Bluetooth® to a device that required such authentication, the signal from one camera could route through the other to use its security and the Intermediary device would be the only device that requires such security provision. This security component may also be able to become a standalone component that is simply inserted into the security path as a pass-through that adds the authentication or approval required only for the receiving device and performs any translation required for the response to be interpreted properly.

Figure 37:
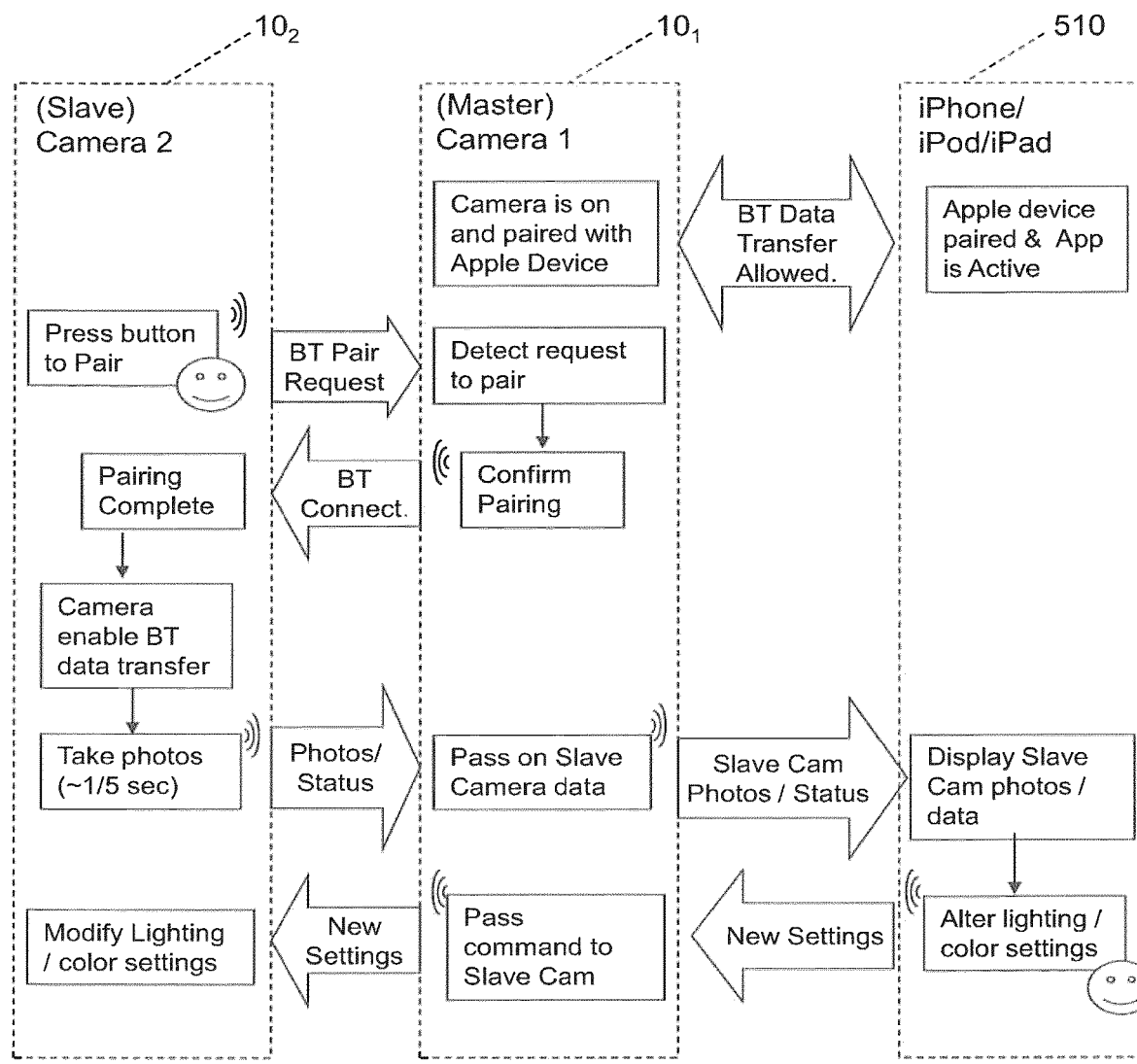
FIG. 37 is a flow diagram showing the digital video camera of FIGS. 26A, 26B, 27A, and 27B and a mobile controller device paired by Bluetooth® wireless connection and cooperating to accomplish without security the passthrough of data from a second Bluetooth®-enabled digital video camera.

FIG. 37 shows an exemplary user application to allow the user to change lighting level and color settings and immediately see the resulting changed video. FIG. 37 is a flow diagram showing Camera 1 and an iOS mobile phone or tablet computer device 510 paired by Bluetooth® wireless connection and cooperating to accomplish without security the pass-through of Camera 2 data. A user pushes the wireless connection activator button on Camera 2 to transmit a Pair Connection Request signal to Bluetooth®-enabled Camera 2, which detects the request, confirms the pairing, and transmits a signal to Camera 2 to complete the pairing.

Camera 2 responds by taking photos in rapid succession and transmitting them together with status information to Camera 1 for pass-through transmission to device 510 for display as Camera 2 image and data on display screen 532. A user manipulates an actuator associated with device 510 to change lighting level and color settings by causing transmission to Camera 1 a New Settings command signal for pass-through transmission to Camera 2, which responds by changing its lighting and color settings.

Data acquisition and data synchronization in the use of wireless communication, preferably in cooperation with GPS capability, can be accomplished by one of several techniques. When capturing video during an activity, data may be used to better describe the activity as well as used for editing and optimizing either during recording or in post-processing. Typically, these data would be embedded in the video as user data or in the file as a data track (in accordance with MPEG specifications). In a first alternative, the data may be written to a text track in the file. These data are ignored by players unless text display is turned on. Post-processing algorithms extract these data for analysis. Generally, the text track survives editing. In a second alternative, the data may be written to a separate file, and the file name for the data may be written as metadata on the video file so that post-processing applications can properly associate the data with the video. Optimally, the data are synchronized with the video, but they need not be frame synchronized. In the event the data are stored in a separate file, a timestamp could be used to synchronize the video. This marker may be embedded in the data file to tag the file at a single time (e.g., beginning, middle, end, or upon designation by the user), tag the file with every video frame, or tag periodically.

FIG. 38 shows a hybrid flow diagram and pictorial illustration of iPhone viewer/controller 510 paired by Bluetooth® wireless data and control command connection to Cameras 1 and 2 to implement a remote Start/Stop capability for multiple cameras. (Cameras 1 and 2 are also identified by the respective reference numerals $10_1$ and $10_2$ to indicate they are of the same type as digital video camera 10.) The flow diagram shows iPhone viewer/controller 510 paired to Cameras 1 and 2 and Contour Connect Mobile App in its active operating mode. The pictorial view of iPhone viewer/controller 510 shows on its display screen 532 a Start Record actuator.

The user wanting to start a recording session taps the Start Record actuator to transmit to Bluetooth®-enabled Cameras 1 and 2 a Start Recording command signal. The flow diagram shows Cameras 1 and 2 recording video data in response to the Start Recording command signal. Bluetooth® wireless module 400 in each of Cameras 1 and 2 is configured to respond to the Start Recording command signal, irrespective of the OFF state of switch activators 80 of Cameras 1 and 2.

The user wanting to complete a recording session taps a Stop Record actuator (not illustrated in FIG. 38) on display screen 532 to transmit to Cameras 1 and 2 a Stop Recording command signal. The flow diagram shows Cameras 1 and 2 stopping video recording in response to the Stop Recording command signal.

FIG. 38 also shows upper and lower timing diagrams illustrating the timing sequences of video frame acquisition by Cameras 1 and 2 when they are, respectively, manually started asynchronously in response to user-positioning of switch activators 80 and started nearly synchronously in response to user-tapping of the Start Record actuator on display screen 532 of iPhone controller/viewer 510. The lower timing diagram shows the benefit of wireless connection in accomplishing near synchronous acquisition of streams of video data from multiple cameras.

Figure 39:
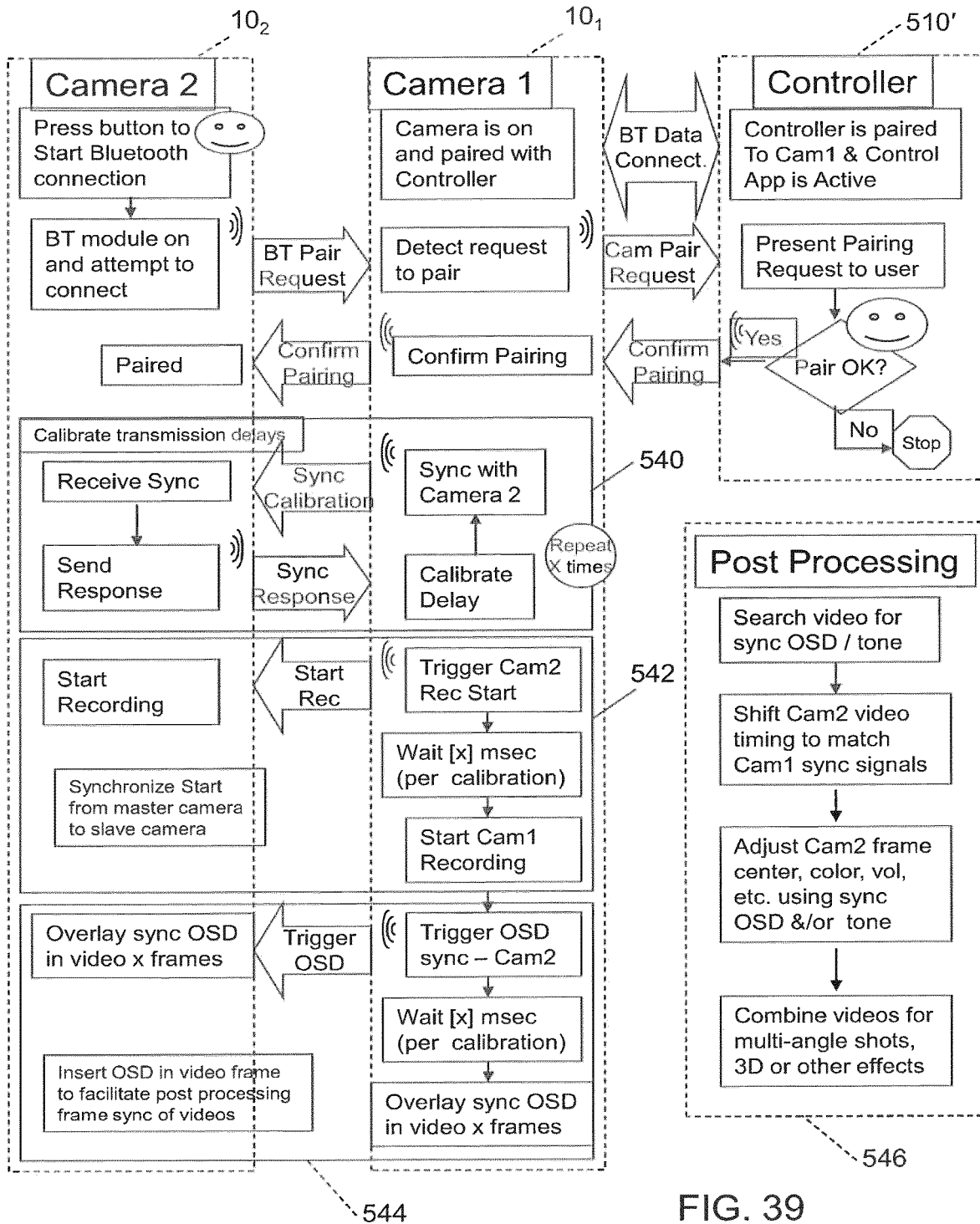
FIG. 39 is a flow diagram showing an example of pairing two digital video cameras of FIGS. 26A, 268, 27A, and 27B by Bluetooth® wireless connection through a mobile controller device.

FIG. 39 is a flow diagram showing an example of pairing Camera 1 and Camera 2 by Bluetooth® wireless data and control command connection through either viewer/controller 510 or controller 510', the latter of which is illustrated in FIG. 39. FIG. 39 shows Camera 1 paired by Bluetooth® wireless connection to controller 510' and Contour Connect Mobile App in its active operating mode. A user presses the wireless connection activator button on Camera 2 to turn on its Bluetooth® module 400, which transmits a Bluetooth® Pair (connection) Request signal to Camera 1. Camera 1, which is already paired with controller 510', detects the Pair Request signal and transmits a Camera Pair Request signal to controller 510'. Controller 510' presents a pairing request to the user, who manipulates an actuator to refuse the requested pairing connection, and thereby stop the pairing process, or manipulates an actuator to accept the requested pairing connection, and thereby transmit and pass through Camera 1 to Camera 2 a Confirm Pairing signal to complete the pairing connection.

A synchronization calibration sequence 540 performed between Cameras 1 and 2 calibrates transmission delays between them. Camera 1 transmits to Camera 2 a Sync Calibration signal, to which Camera 2 responds by transmitting a Sync Response signal. Camera 1 determines a calibration delay representing the amount of delay from transmission of the Sync Calibration signal to receipt of the Sync Response signal. This process is repeated a number of times until successive measured calibrated delays are within an operational tolerance.

A synchronized video recording process 542 starts upon completion of synchronization calibration sequence 540. Camera 1, operating as the master camera and in response to a user-controlled trigger signal, transmits a Start Recording signal to Camera 2, which responds by starting to record video data. Camera 1 starts to record video data after expiration of the calibrated delay determined by the synchronization calibration sequence 540 to achieve a synchronized start of recording video data by Cameras 1 and 2.

An on-screen display ("OSD") sync pulse insertion process 544 facilitates video frame synchronization in video and audio post-processing. Camera 1 transmits a Trigger OSD Sync signal to Camera 2 in response to the start of video data recording by Camera 1. Camera 2 responds to the Trigger OSD Sync signal by inserting an OSD Sync pulse overlay in the stream of video frames Camera 2 acquires. After expiration of the calibrated delay determined by synchronization calibration sequence 540, Camera 1 inserts an OSD Sync pulse overlay in the stream of video frames Camera 1 acquires. The time base for computing calibration delay and OSD Sync pulse insertion is preferably provided by a GPS date/time clock available to GPS receiver 458.

A video and audio post-processing procedure 546 entails performing a search of the streams of video frames for the OSD Sync pulses and shifting the timing of the stream of video frames of Camera 2 to match the OSD Sync pulses of Camera 1. The frame center, color, audio volume, and other parameters of the Camera 2 video and audio data are adjusted using the OSD Sync pulse so that the streams of video and audio data can be combined for multi-angle shots, three-dimensional images, or other effects.

Figure 40:
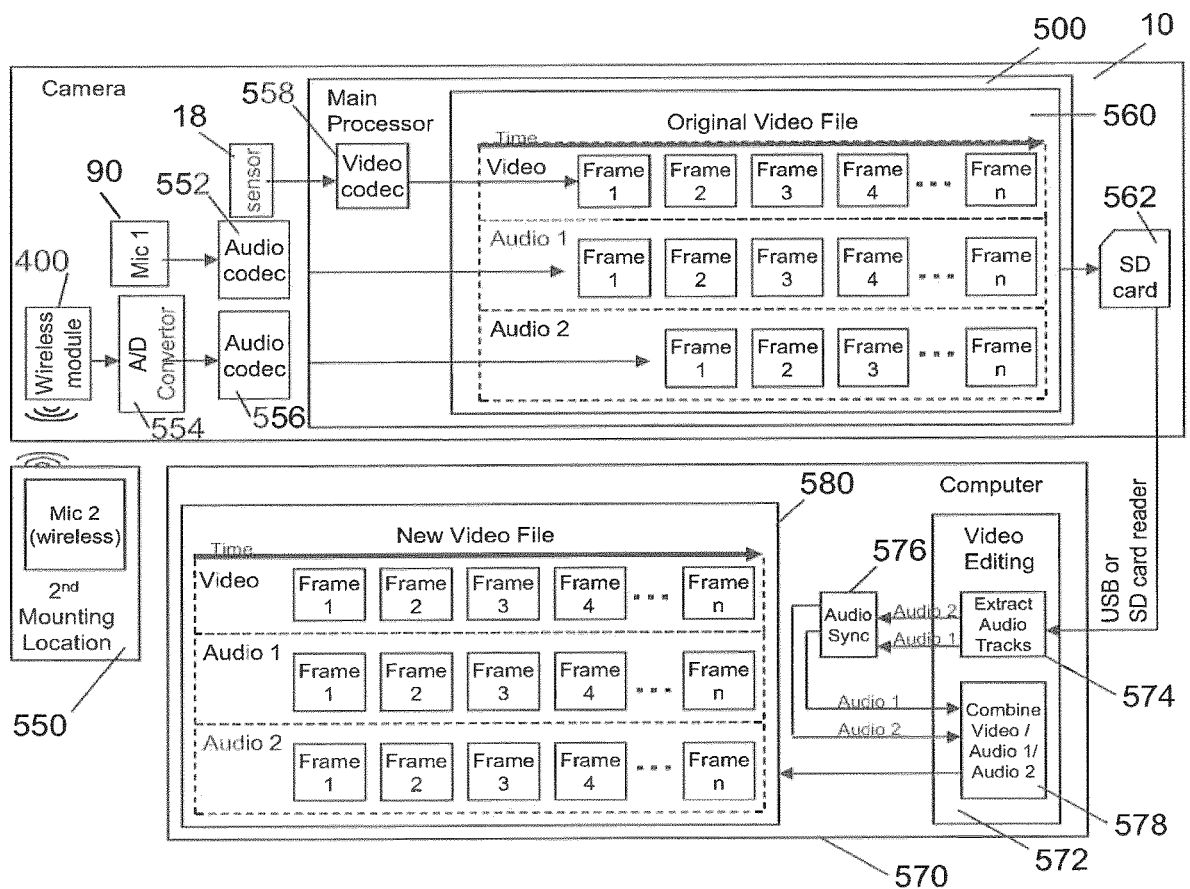
FIG. 40 is a block diagram showing the post-processing procedure of synchronizing audio data produced by a wireless microphone and hard-wired microphone incorporated in the digital video camera of FIGS. 26A, 26B, 27A, and 27B.

FIG. 40 is a block diagram showing the post-processing procedure of synchronizing audio data produced by a wireless microphone 550 and wired microphone 90 incorporated in digital video camera 10. Audi data produced by microphone 90 are compressed by an audio codec 552. An audio signal produced by wireless microphone 550 is received by Bluetooth® wireless module 400, converted to digital form by an analog-to-digital convertor 554, and compressed by an audio codec 556. Video data produced by image sensor 18 is compressed by a video codec 558, which resides in main processor 500 of digital video camera 10. An Audio 1 Track of hard-wired audio data, an Audio 2 Track of wireless audio data, and a Video Track of video data delivered from the respective outputs of audio codec 552, audio codec 556, and video codec 558 are combined and contained as parallel tracks in an original video file 560 and stored in an SD memory card 562.

Wireless microphone 550 introduces a delay in the Audio 2 Track. FIG. 40 illustrates this delay by showing a one-frame temporal offset between corresponding frames of the Audio 1 and 2 Tracks. The above-described OSD Sync pulse functions as an audio time stamp that can be used to correct for the delay and thereby synchronize the Audio 1 and 2 Tracks for automatic post-processing audio analysis. Post-processing is performed in a peripheral computer 570, which includes a video editor 572 having an audio tracks extraction module 574 that receives from SD card 562 the stored Video, Audio 1, and Audio 2 Tracks data from original video file 560. Audio tracks extraction module 574 separates the Audio 1 and 2 Tracks, and an audio synchronizer module 576 using the time stamp sync pulse synchronizes them. The synchronized Audio 1 and 2 Tracks, together with the Video Track, are combined in a video/audio combiner module 578 and delivered in proper temporal frame alignment to a new video file 580.

Data measurements performed depend on the type of data acquired. The most appropriate data varies based upon sport or type of motion recorded; therefore, ideally data sensors are tailored to the relevant sport. Additionally, the best location for measuring data is often not the ideal location for mounting a camera.

Figure 41:
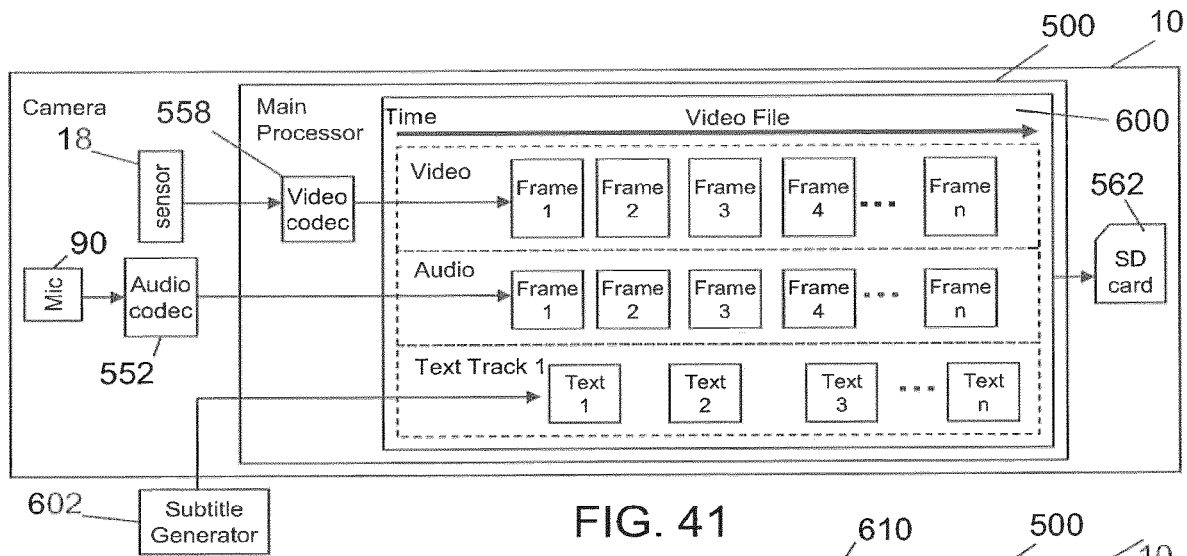
FIG. 41 is a simplified block diagram showing the processing of a single track of data from one data source.

FIG. 41 is a simplified block diagram showing the processing of a single track of data from one data source. FIG. 41 shows digital video camera 10 including in its main processor 500 a video file 600 containing a Video Track, an Audio Track, and a Text Track. The Video and Audio Tracks correspond to, respectively, the Video and Audio 1 Tracks contained in original video file 560 of FIG. 40. The Text Track represents data that are produced by a subtitle generator 602 hardwired to main processor 500 and is presented for display on the video frames.

By using Bluetooth® with its many-to-many connections, multiple data sources can be recorded by the camera. These data sources can be customized to the specific application, for example for automobile racing, data relating to the automobile engine may be captured from on-board diagnostics and transmitted to digital video camera 10, where the data can be embedded in the video stream for later playback. Examples of multiple data sources include streaming data to one or more cameras from one or more data sources (e.g., GPS data from telephone or GPS collection device, and audio data from remote microphone) and storing such data as individual files or embedded in the video file as metadata, audio tracks, or text.

In post-processing, data associated with video content can be used in editing to correct for shade/lighting changes, to correct for video processing errors, and to enhance the story with information about the path taken, location of the video, speed, and other information. Location and time data embedded in video from sources such as GPS can be used to synchronize videos in post-processing generating a three-dimensional video. Speed, vibration, altitude, temperature, date, and location can be combined to determine the likely sport or activity as part of a post-processing suite. The recommendations can be tuned based on data gathered from a large body of videos in which the activity in the video has been identified. Data associated with video content may be used to associate and group videos from one or more users. The groupings may be based on any characteristic such as time, location, speed, and other factors. Videos that intersect in time or location may be linked so that the viewer can transition to a different camera or video when two videos cross in location or time. Additionally, the data can be used to correlate multiple cameras or videos to create multiple view angles for the same location or event. These data may also be used to correlate videos of the same location taken over time to document the changes in that location over extended durations (hours, days, weeks, years).

Multiple "language" tracks on video file can be used to capture different audio sources (including wireless microphone) from the video camera. This allows the user to select from the optimal audio source in post-processing or allows automatic correction for signal errors and synchronization issues. By storing multiple sources, users are post-processing algorithms and may select the most reliable track in the event there is a dropout resulting from signal quality issues caused by use of a wireless device. Additionally, audio may be captured from multiple sources and from different locations to provide different audio information so that the preferred audio may be selected in post-processing. In the event multiple audio tracks are not available, data tracks may be used and the data can be converted into an audio source in post-processing. In the event the wireless audio source cannot be channeled through the audio codec, the raw data can be stored and post-processing can modify these data to convert them to audio. Any delay introduced by the wireless connection can be corrected by synchronizing the wireless audio source to the primary audio source (internal microphone) using the audio waveforms.

The foregoing approach differs from the prior art technique of automatically switching between an internal microphone and an external microphone, where the external microphone is used when it exists and software automatically reverts to the internal microphone when the external microphone signal is unavailable. Automatic switching would, however, mix audio from different locations and not provide a seamless audio experience.

Figure 42:
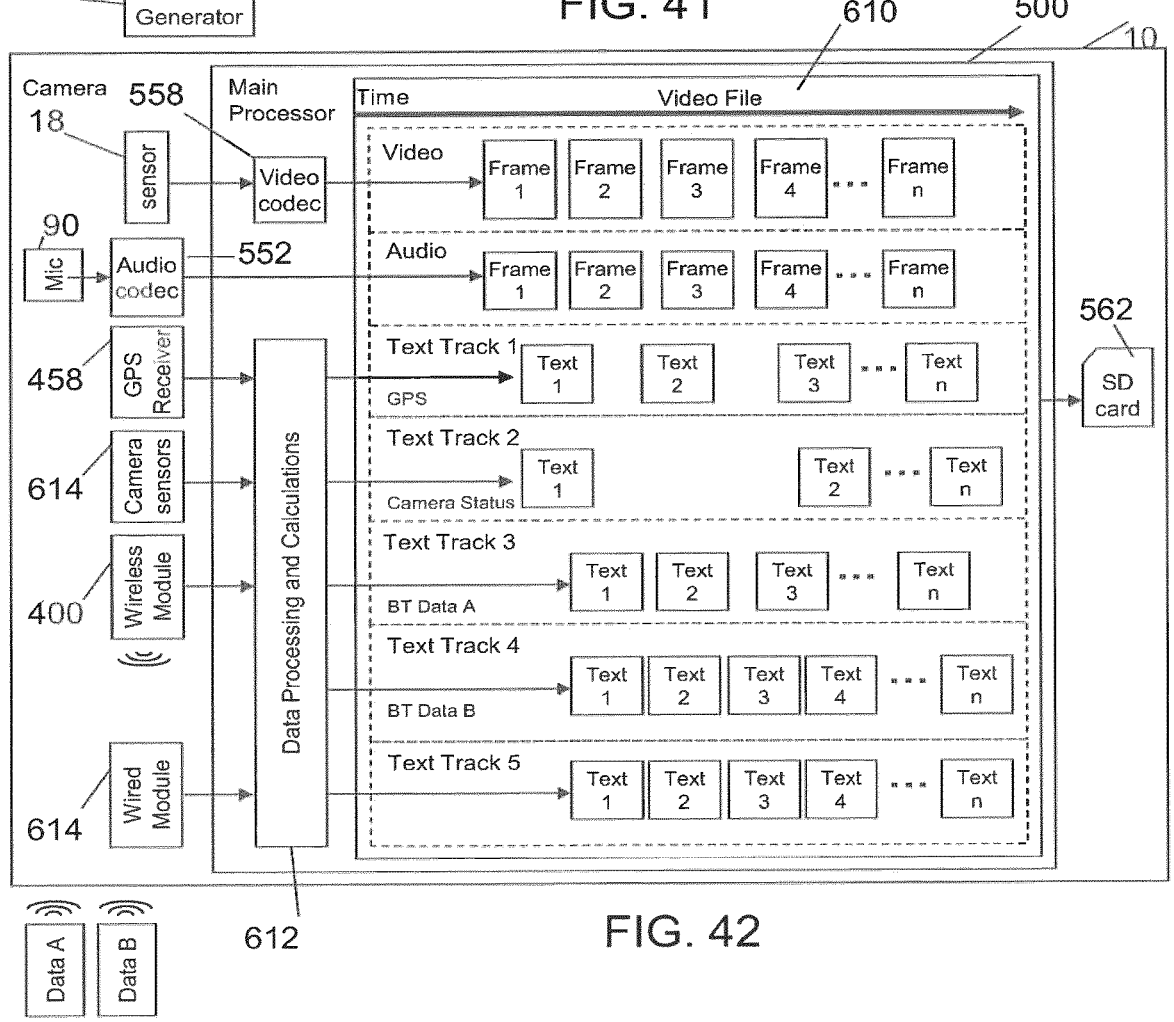
FIG. 42 is a simplified block diagram showing the processing of multiple tracks of data from multiple data sources.

FIG. 42 is a simplified block diagram showing the processing of multiple tracks of data from multiple data sources. FIG. 42 shows digital video camera 10 including in its main processor 500 a video file 610 containing Video and Audio Tracks corresponding to those contained in video file 600 of FIG. 41 and five text tracks described below.

A data processing and calculations module 612 of main processor 500 receives data from GPS receiver 458, camera sensors 614, Bluetooth® wireless module 400 receiving data transmissions from Bluetooth® wireless connection-enabled sources, and a wired data module 614 and delivers these data as Text Track 1, Text Track 2, Text Track 3, Text Track 4, and Text Track 5, respectively.

Text Track 1 contains GPS data such as longitude, latitude, elevation, date/time, and other data available from GPS receiver 458. The date/time information enables associating acquired video and other data, including data on Text Tracks 2-5, to a certain time point in the video data stream. Peripheral computer 570 takes the time-stamped information and displays it by time point. The transmission delay calibration described with reference to FIG. 39 can be implemented using the GPS-provided date/time clock as a time standard.

Text Track 2 contains operating parameter data such as video resolution, compression rate, and frame rate information available from camera sensors 614 associated with digital video camera 10.

Text Tracks 3 and 4 contain data acquired from Bluetooth® wireless connection-enabled Data A and Data B transmission sources such as, for example, race car engine sensor data and race car driver heart rate monitor data. These data are typically periodically transmitted to Bluetooth® module 400. Another example of Data A and Data B sources is data sources transmitting data at different transmission rates.

Text Track 5 contains data produced from a text data module (e.g., subtitle generator 602 of FIG. 41) hardwired to data processing and calculations module 612.

It will be obvious to those having skill in the art that many changes may be made to the details of the above-described embodiments without departing from the underlying principles of the invention. For example, skilled persons will appreciate that subject matter of any sentence or paragraph can be combined with subject matter of some or all of the other sentences or paragraphs, except where such combinations are mutually exclusive. The scope of the present invention should, therefore, be determined only by the following claims.

The invention claimed is:

1. A first video camera, comprising:
   a lens;
   an image sensor configured to generate first image data from light propagating through the lens;
   at least one non-audio data sensor configured to produce first non-audio sensor data associated with the first video camera;
   a wireless connection protocol device; and
   a processor, comprising:
      a video encoder, and
      memory,
   wherein the processor is configured to:
      receive the first image data from the image sensor,
      receive the first non-audio sensor data from the at least one non-audio data sensor,
      generate at least one encoded video data stream using the video encoder, wherein a data type of the first non-audio sensor data is different from a data type of the at least one encoded video data stream,
      send, using the wireless connection protocol device, the at least one encoded video data stream by wireless transmission to a first remote computing device, wherein the first remote computing device is connected to a first data storage medium, and wherein the first remote computing device is configured to store the at least one encoded video data stream on the first data storage medium as a first file,
      combine the first non-audio sensor data with the at least one encoded video data stream to form a combined video stream,
      communicate at least part of the combined video stream to the memory, wherein the at least one encoded video data stream is stored as a first track and the first non-audio sensor data is stored as a second track that is distinct from the first track, and
      generate time-synchronizing data,
   wherein the time-synchronizing data is used to synchronize the first track with the second track,
   wherein the first video camera is configured as a media server that enables access to the combined video stream.

2. The first video camera of claim 1, further comprising:
   a second data storage medium,
   wherein the processor is configured to store the at least one encoded video data stream on the second data storage medium as a second file.

3. The first video camera of claim 2, further comprising:
   a post-processor,
   wherein the post-processor receives the combined video stream and associates one or more event categories with the combined video stream based on content of the combined video stream.

4. The first video camera of claim 3, wherein the one or more event categories associated with the combined video stream are determined based on data gathered from a body of video streams with which event categories have been previously associated.

5. The first video camera of claim 2, wherein a post-processor receives the combined video stream and associates one or more event categories with the combined video stream based on content of the combined video stream, wherein the post-processor is a second remote computing device.

6. The first video camera of claim 1, further comprising:
   a display,
   wherein the processor is configured to cause the display to show the first image data.

7. The first video camera of claim 6, wherein the at least one non-audio data sensor is a GPS receiver.

8. The first video camera of claim 7, further comprising:
   a microphone; and
   an audio encoder,
   wherein the microphone is configured to produce audio data,
   wherein the audio encoder is configured to produce an encoded audio data stream from the audio data, and
   wherein the processor is configured to embed the encoded audio data stream with the at least one encoded video data stream.

9. The first video camera of claim 8, further comprising:
   a switch activator,
   wherein the switch activator activates the first video camera.

10. The first video camera of claim 7,
    wherein at least one second video camera is configured to produce second image data,
    wherein the processor is configured to:
       receive the second image data from the at least one second video camera, and
       communicate at least part of the second image data to the memory.

11. The first video camera of claim 6, wherein the at least one non-audio data sensor is an automotive sensor comprising an engine sensor.

12. The first video camera of claim 1, wherein the processor is configured to:
    send, using the wireless connection protocol device, the combined video stream by wireless transmission to the first remote computing device.

13. A method for capturing video, the method comprising:
    receiving first image data from an image sensor of a first video camera, the first video camera comprising a lens and the image sensor;
    generating at least one encoded video data stream using a video encoder of a processor, sending, using a wireless connection protocol device of the first video camera, the at least one encoded video data stream by wireless transmission to a remote computing device, wherein the remote computing device is connected to a first data storage medium, and wherein the remote computing device is configured to store the at least one encoded video data stream on the first data storage medium as a first file, receiving first non-audio sensor data from at least one non-audio data sensor, wherein a data type of the first non-audio sensor data is different from a data type of the at least one encoded video data stream, combining the first non-audio sensor data with the at least one encoded video data stream to form a combined video stream, communicating at least part of the combined video stream to memory of the processor, wherein the at least one encoded video data stream is stored as a first track and the first non-audio sensor data is stored as a second track that is distinct from the first track, and generating time-synchronizing data, wherein the time-synchronizing data is used to synchronize the first track with the second track, wherein the first video camera is configured as a media server that enables access to the combined video stream.

14. The method of claim 13, further comprising:
storing the at least one encoded video data stream as a second file on a second data storage medium connected to the processor.

15. The method of claim 14, further comprising displaying the first image data on a display.

16. The method of claim 15, wherein the first non-audio sensor data is GPS data received from a GPS receiver.

17. The method of claim 16, further comprising:
receiving audio data from a microphone;
producing an encoded audio data stream from the audio data using an audio encoder; and
embedding the encoded audio data stream with the at least one encoded video data stream using the processor.

18. The method of claim 17, further comprising activating recording by the first video camera using a switch activator.

19. The method of claim 16, wherein the first non-audio sensor data is engine data received from an engine sensor.

20. The method of claim 16, further comprising:
receiving second image data from at least one second video camera, the at least one second video camera comprising a at least one lens and at least one image sensor; and
communicating at least part of the second image data to the memory of the processor.

21. The method of claim 14, further comprising producing event category data associated with the first image data using the at least one non-audio data sensor.

22. The method of claim 14, further comprising producing event category data based on data gathered from a body of image data with which event categories have been previously associated.

23. The method of claim 22, further comprising sending, using a wireless connection protocol device, the combined video stream by wireless transmission to the remote computing device.

24. A first video camera, comprising:
a lens;
an image sensor configured to generate first image data from light propagating through the lens;
at least one non-audio data sensor configured to produce first non-audio sensor data associated with the first video camera;
a wireless connection protocol device; and
a processor comprising a video encoder and memory,
wherein the processor is configured to:
receive the first image data from the image sensor,
receive the first non-audio sensor data from the at least one non-audio data sensor,
generate at least one encoded video data stream using the video encoder, wherein a data type of the first non-audio sensor data is different from a data type of the at least one encoded video data stream,
send, using the wireless connection protocol device, the at least one encoded video data stream by wireless transmission to a remote computing device, wherein the remote computing device is connected to a data storage medium, and wherein the remote computing device is configured to store the at least one encoded video data stream on the data storage medium as a file,
communicate at least part of the at least one encoded video data stream to the memory, wherein the at least one encoded video data stream is stored as a first track,
communicate at least part of the first non-audio sensor data to the memory, wherein the first non-audio sensor data is stored as a second track that is distinct from the first track,
combine the first non-audio sensor data with the at least one encoded video data stream to form a combined video stream, and
generate time-synchronizing data,
wherein the time-synchronizing data is used to synchronize the first track with the second track,
wherein the first video camera is configured as a media server that enables access to the combined video stream.

* * * * *